(12) United States Patent
Baillie et al.

(10) Patent No.: US 10,281,472 B2
(45) Date of Patent: May 7, 2019

(54) CANCER DIAGNOSIS AND THERAPY

(71) Applicant: GILLIES MCINDOE RESEARCH INSTITUTE, Wellington (NZ)

(72) Inventors: Ranui Francesca Baillie, Wellington (NZ); Paul Frank Davis, Wellington (NZ); Tinte Itinteang, Wellington (NZ); Swee Thong Tan, Wellington (NZ)

(73) Assignee: GILLIES MCINDOE RESEARCH INSTITUTE, Wellington (NZ)

( * ) Notice: Subject to any disclaimer, the term of this patent is extended or adjusted under 35 U.S.C. 154(b) by 0 days.

(21) Appl. No.: 15/503,025

(22) PCT Filed: Aug. 12, 2015

(86) PCT No.: PCT/NZ2015/050108
§ 371 (c)(1),
(2) Date: Feb. 10, 2017

(87) PCT Pub. No.: WO2016/024870
PCT Pub. Date: Feb. 18, 2016

(65) Prior Publication Data
US 2017/0234884 A1 Aug. 17, 2017

Related U.S. Application Data

(60) Provisional application No. 62/036,583, filed on Aug. 12, 2014.

(51) Int. Cl.
*A61K 31/59* (2006.01)
*A61K 33/06* (2006.01)
*A61K 45/00* (2006.01)
*A61P 35/00* (2006.01)
*G01N 33/574* (2006.01)

(52) U.S. Cl.
CPC ....... *G01N 33/57496* (2013.01); *A61K 31/59* (2013.01); *A61K 33/06* (2013.01); *A61K 45/00* (2013.01); *A61P 35/00* (2018.01); *G01N 33/57407* (2013.01); *G01N 33/57492* (2013.01)

(58) Field of Classification Search
CPC .......... G01N 33/574; G01N 33/57496; G01N 33/57492
See application file for complete search history.

(56) References Cited

U.S. PATENT DOCUMENTS

| | | | |
|---|---|---|---|
| 6,004,528 A | 12/1999 | Bergstein | |
| 6,162,432 A | 12/2000 | Wallner et al. | |
| 6,605,589 B1 * | 8/2003 | Uckun | A61K 38/55 514/18.9 |
| 6,733,743 B2 | 5/2004 | Jordan | |
| 6,946,475 B1 * | 9/2005 | Gray | C07D 207/08 514/317 |
| 7,361,336 B1 | 4/2008 | Bergstein | |
| 2005/0002934 A1 | 1/2005 | Reed | |
| 2006/0083682 A1 | 4/2006 | Bergstein | |
| 2007/0036800 A1 | 2/2007 | Bergstein | |
| 2007/0036801 A1 | 2/2007 | Bergstein | |
| 2007/0036802 A1 | 2/2007 | Bergstein | |
| 2007/0036803 A1 | 2/2007 | Bergstein | |
| 2007/0036804 A1 | 2/2007 | Bergstein | |
| 2007/0041984 A1 | 2/2007 | Bergstein | |
| 2011/0262358 A1 * | 10/2011 | Torigoe | C12N 15/113 424/9.1 |
| 2011/0269780 A1 * | 11/2011 | Emmanuel | C07D 471/04 514/263.2 |
| 2015/0125445 A1 * | 5/2015 | Herr | C07K 16/28 424/133.1 |
| 2016/0146819 A1 * | 5/2016 | Ince | G01N 33/743 514/167 |

FOREIGN PATENT DOCUMENTS

| | | |
|---|---|---|
| WO | WO-1993/0686 A1 | 1/1993 |
| WO | WO-2002/098370 A2 | 12/2002 |
| WO | WO-2012/030234 A1 | 3/2012 |

OTHER PUBLICATIONS

Takehashi et al., Prostate. 2012;72:1559-1572 (Year: 2012).*
Moscarelli et al., Clin. Nephrol. 2010 73:439-445 (Abstract only) (Year: 2010).*
Carina et al., Thyroid. Jul. 2013;23(7):829-837 (Year: 2013).*
Al-Hajj et al., Prospective identification of tumorigenic breast cancer cells, *Proc Nat. Acad. Sci USA*, 100:3983-8 (2003).
Bonnet et al., Human acute myeloid leukemia is organized as a hierarchy that originates from a primitive hematopoietic cell, *Nat. Med.*, 3:730-737 (1997).
Cox et al., Prospective identification of tumorigenic breast cancer cells, *Blood*, 104(19):2919-25 (2004).
Frankel et al., Diphtheria toxin fused to human interleukin-3 is toxic to blasts from patients with myeloid leukemias, *Leukemia*, 14:576 (2000).
Itinteang et al., Expression of components of the renin-angiotensin system in proliferating infantile haemangioma may account for the propranolol-induced accelerated involution, *J. Plast. Reconstruct. Aesth. Surg.*,64:759-65 (2011).
Itinteang et al., Infantile haemangioma expresses embryonic stem cell markers, *J. Clin. Pathol.*, 65:394-8 (2012).

(Continued)

*Primary Examiner* — Daniel C Gamett
(74) *Attorney, Agent, or Firm* — Marshall, Gerstein & Borun LLP

(57) ABSTRACT

The present invention provides a novel approach to cancer diagnosis and therapy of cancer by providing compositions and methods for the identification and specific targeting of the cancer stem cell populations present in a tumor to eradicate, or slow or prevent tumor (5) growth and spread, including the potential for tumor metastasis, by modulation of the Renin-Angiotensin System including, but not limited to, Renin Receptor, Angiotensin II Receptor (2) and a secreted form of the Renin Receptor.

8 Claims, 30 Drawing Sheets

(56) References Cited

OTHER PUBLICATIONS

Matsui et al., Characterization of clonogenic multiple myeloma cells, *Blood* 103(6):2332 (2004).
Mattheolabakis et al., Topically Applied Phospho-Sulindac Hydrogel is Efficacious and Safe in the Treatment of Experimental Arthritis in Rats, *Pharmaceutical Research*, 30(6):1471-82 (2013).
Physician's Desk Reference, Montvale, NJ, Thompson PDR, 60th ed. (2006).
Tan et al, Low-Dose Propranolol for Multiple Hepatic and Cutaneous Hemangiomas With Deranged Liver Function, *Pediatrics*, 127(3):772-6 (2011).
Urieto et al., Expression and purification of the recombinant diphtheria fusion toxin DT388IL3 for phase I clinical trials, *Protein Expression and Purification*, 33: 123-33 (2004).
Wang et al., Identification of renal cathepsin B as a human prorenin-processing enzyme, *J. Biol. Chem.*, 266(19):12633-38 (1991).
Wang et al., Targeting cancer stem cells: emerging role of Nanog transcription factor, *OncoTarg. Ther.*, 6:1207-20 (2013).
Zhu et al., Phosphosulindac (OXT-328) selectively targets breast cancer stem cells in vitro and in human breast cancer xenografts, *Stem Cells*, 30(10):2065-5 (2012).
International Preliminary Report on Patentability, Australian Patent Office, PCT/NZ2015/050108, dated Feb. 14, 2017.
International Search Report and Written Opinion of the International Search Authority, Australian Patent Office, PCT/NZ2015/050108, dated Sep. 30, 2015.

\* cited by examiner

CANCER DIAGNOSIS AND THERAPY

TECHNICAL FIELD

The present invention provides a novel approach to cancer diagnosis and cancer therapy. In particular, the identification and specific targeting of cancer stem cell populations present in a tumour to eradicate or slow or prevent tumour growth and spread, including the potential for tumour metastasis, is contemplated within the scope of the present invention. The present invention is particularly useful in the identification and treatment of tumours.

BACKGROUND OF THE INVENTION

Next to cardiovascular disease, cancer is one of the most significant health conditions worldwide that accounts for approximately one in four deaths. In the United States alone, health costs are estimated to run into the hundreds of billions of dollars per annum, with around a hundred billion dollars in direct expenditures currently. This expenditure is estimated to be up to US$207 billion by 2020. The incidence of cancer is widely expected to increase as the population ages worldwide, further augmenting the impact of this spectrum of diseases. The current treatment regimens for cancer, established in the 1970s and 1980s, have not changed dramatically. These treatments, which include surgery, radiotherapy and chemotherapy, and other modalities including newer targeted therapies, have shown limited overall survival benefit when utilised in more advanced stage cancers since, among other things, these therapies primarily target the tumour bulk rather than cancer stem cells, which are thought to drive tumourigenesis.

Conventional cancer diagnosis and therapies to date have attempted to selectively detect and eradicate neoplastic cells that are largely fast-growing (i.e., cells that form the tumour bulk). Standard cancer treatment regimens have often been largely designed to the deliver the highest dose of radiation and/or administer chemotherapeutic agent without undue toxicity, i.e., often referred to as the "maximum tolerated dose" (MTD) or "no observed adverse effect level" (NO-AEL). Chemotherapy is often added to radiotherapy to improve cancer control, at the expense of increased toxicities. Many conventional cancer chemotherapies (e.g., alkylating agents such as cyclophosphamide; antimetabolites such as 5-Fluorouracil; plant alkaloids such as vincristine) and conventional radiation therapies exert their toxic effects on cancer cells largely by interfering with cellular mechanisms involved in cell growth and DNA replication. Chemotherapy protocols also often involve administration of a combination of chemotherapeutic agents in an attempt to increase the efficacy of the treatment. Despite the availability of a large variety of chemotherapeutic agents, these therapies have many limitations. For example, chemotherapeutic agents are notoriously toxic due to non-specific effects on fast-growing cells whether normal or malignant. For example, chemotherapeutic agents cause significant, and often serious toxicities, including bone marrow depression, immunosuppression, gastrointestinal distress, etc.

Other types of traditional cancer therapies include surgery, hormonal therapy, immunotherapy, epigenetic therapy, anti-angiogenesis therapy, targeted therapy (e.g., therapy directed to a cancer target with agents such as Gleevec® and other tyrosine kinase inhibitors, Velcade®, Sutent® etc.), and radiation therapy to eradicate neoplastic cells in a patient. All of these approaches, often in combination, can pose significant drawbacks for the patient including a lack of efficacy, toxicity and loss of quality of life. Accordingly, new and more effective therapies and/or regimens for improving the long-term prospect including survival and reduced side effects of treatment of cancer patients are needed.

Cancer stem cells comprise a unique subpopulation (typically ~0.1-10%) of a tumour that, relative to the remaining 90% or so of the tumour (i.e., the tumour bulk), are more tumourigenic, relatively more slow-growing or quiescent, and often more chemotherapy and/or radiotherapy resistant than the tumour cells. Given that conventional therapies and regimens have, in large part, been designed to attack rapidly proliferating cells (i.e., those cancer cells that comprise the tumour bulk), cancer stem cells which are often slow-growing are relatively more resistant than faster growing tumour cells to conventional therapies and regimens. Furthermore, cancer stem cells may possess other features that endow them with chemo-resistance such as multi-drug resistance, and develop and/or enhance anti-apoptotic pathways. These features would constitute a key reason for the failure of standard cancer treatments to ensure long-term benefit in most patients especially those with more advanced-stage cancers (i.e., the failure to adequately target and eradicate cancer stem cells). In some instances, a cancer stem cell(s) is the founding cell of a tumour (i.e., it is a progenitor giving rise to the cancer cells that comprise the tumour bulk).

Two models of cancer stem cell proliferation have been proposed. The stochastic model postulates that oncogenic mutations occur randomly in normal cells and that every cell within a tumour has a low but equal likelihood of re-initiating a tumour. In contrast, the cancer stem cell model posits that tumours arise from a small, phenotypically distinct subset of cancer cells that give rise to the heterogeneous cell lineages observed in a tumour.

Cancer stem cells have several properties that distinguish them from the remainder of the cancer cell population. Most importantly, they undergo asymmetrical cell division, a unique type of cell division in which one offspring cell remain identical to the parent cell, while the other differentiates. In normal adult tissues, self-renewal is displayed exclusively by adult stem cells. Like embryonic stem cells, cancer stem cells sit on top of the tumour cell hierarchy and can respond to stimuli to generate cells further along the differentiation spectrum, albeit in an aberrant manner. Cancer stem cells are also resistant to chemotherapy and radiotherapy, which could explain why conventional treatments are ineffective in curing cancer and relapse occurs in the generally more aggressive forms. Moreover, some cancer stem cells are relatively quiescent shielding them from drugs that target highly proliferating cells. Finally, cancer stem cells can result in metastasis in cancers.

Cancer stem cells have been identified in a large variety of cancer types. For example, leukaemia cells bearing the specific phenotype $CD34^+CD38^-$ (comprising <1% of a given leukaemia), unlike the remaining 99+% of the leukaemia bulk, were able to recapitulate the leukaemia from when it is derived when transferred into immunodeficient mice (Bonnet et al. (1997) *Nat Med* 3:730-737). That is, these cancer stem cells are found as <1 in 10,000 leukaemia cells, yet this low frequency population is able to initiate and serially transfer a human leukaemia with the same histologic phenotype as in the original tumour into severe combined immunodeficiency/non-obese diabetic (NOD/SCID) mice.

Similar studies involving cancer stem cells isolated from, for example, human breast cancer ($CD44^+CD24^{low\ lin}$; Al-Hajj et al. (2003) *Proc Nat. Acad. Sci USA* 100:3983-3988), human acute lymphoblastic leukaemia ($CD34^+CD10^-$, $CC34^+CD19^-$; Cox et al. (2004) *Blood* 104(19):2919-2925), and multiple myeloma (CD138⁻; Matsui et al. (2004) *Blood* 103(6):2332) have all been shown to have increased tumourigenic potential in recapitulation studies in mice.

Since conventional cancer therapies target rapidly proliferating cells (i.e., cells that form the tumour bulk) these treatments are believed to be relatively ineffective at targeting and impairing cancer stem cells. In fact, cancer stem cells, including leukaemia stem cells, have been shown to be relatively resistant to conventional chemotherapeutic agents (e.g., Ara-C, Daunorubicin) as well as newer targeted therapies (e.g., Gleevec®, Velcade®). For example, leukaemic stem cells are relatively slow-growing or quiescent, express multi-drug resistance genes, and utilise other anti-apoptotic mechanisms, features which contribute to their chemo-resistance. Further, by virtue of their chemo-resistance, cancer stem cells may contribute to treatment failure, and may also persist following treatment or recur at a later date following apparent initial clinical remission.

Targeting cancer stem cells is expected to provide for improved long-term outcomes for cancer patients. Accordingly, a need exists to provide new therapeutic agents and/or treatments designed to target cancer stem cells to achieve more successful therapeutic outcomes. The present invention seeks to address this problem.

SUMMARY OF THE INVENTION

The inventions described and claimed herein have many attributes and embodiments including, but not limited to, those set forth or described or referenced in this Summary of the Invention. It is not intended to be all-inclusive and the inventions described and claimed herein are not limited to or by the features or embodiments identified in this Summary of the Invention, which is included for purposes of illustration only and not restriction.

Applicants have identified discrete populations of cancer stem cells that have been shown to be associated with an extensive range of different tumour types, affecting the major organ systems examined. Accordingly, identification of these cancer stem cells and the cancer stem cell populations provides a novel approach to the management of cancer, as well as in prognostic, diagnostic and follow-up applications. In addition, the Applicants have surprisingly demonstrated that these cancer stem cells express markers associated with key regulatory systems including, for example, the Renin-Angiotensin System (RAS) including the Pro/Renin Receptor System (PRRS) and the associated bypass pathways. This novel insight provides a novel target and unique therapeutic opportunity in the management of cancer by employing established and/or novel drugs that specifically target these regulatory pathways in an attempt to eradicate, or arrest growth, proliferation and/or differentiation of cancer stem cell populations. This has the potential to reduce both the tumourigenic and metastatic potential of nascent and established tumours.

Accordingly, in one aspect of the present invention there is provided a method for preventing, treating, or managing cancer in a patient in need thereof, the method comprising administering a therapeutic agent to the patient in an amount sufficient to selectively eradicate, or inhibit the growth, proliferation and/or differentiation of cancer stem cells in a tumour within the cancer, wherein the cancer stem cells are characterised by (i) the expression of one or more embryonic stem cell biomarkers, and (ii) the expression of one or more biomarkers associated with the Renin-Angiotensin System.

In another aspect of the present invention there is provided a method for preventing, treating, or managing cancer in a patient in need thereof, the method comprising administering a therapeutic agent to the patient in an amount sufficient to selectively eradicate, or inhibit the growth, proliferation and/or differentiation of cancer stem cells within the cancer, wherein the cancer stem cells are characterised by (i) the expression of one or more embryonic stem cell biomarkers, and (ii) the expression of one or more biomarkers associated with the Renin-Angiotensin System, and wherein the cancer is a solid cancer or blood cancer.

In yet another aspect of the present invention there is provided a method for preventing, treating, or managing cancer in a patient in need thereof, the method comprising administering a therapeutic agent to the patient in an amount sufficient to selectively eradicate, or inhibit the growth, proliferation and/or differentiation of cancer stem cells within the cancer, wherein the cancer stem cells are characterised by (i) the expression of one or more embryonic stem cell biomarkers, and (ii) the expression of one or more biomarkers associated with the Renin-Angiotensin System, and wherein the tumour is selected from the group consisting of squamous cell carcinoma of the oral cavity, squamous cell carcinoma of the skin, melanoma, lung cancer, breast cancer, kidney cancer, brain cancer, bowel cancer, thyroid cancer, prostate cancer, lymphoma, leukaemia and sarcomas.

In yet a further aspect of the present invention there is provided a method for preventing, treating, or managing cancer in a patient in need thereof, the method comprising administering a therapeutic agent to the patient in an amount sufficient to selectively eradicate, or inhibit the growth, proliferation and/or differentiation of cancer stem cells within the cancer, wherein the cancer stem cells are characterised by (i) the expression of one or more embryonic stem cell biomarkers, and (ii) the expression of one or more biomarkers associated with the Renin-Angiotensin System, and wherein the tumour is a squamous cell carcinoma.

In another aspect of the present invention there is provided a method for preventing, treating, or managing cancer in a patient in need thereof, the method comprising administering a therapeutic agent to the patient in an amount sufficient to selectively eradicate, or inhibit the growth, proliferation and/or differentiation of cancer stem cells within the cancer, wherein the cancer stem cells are characterised by (i) the expression of one or more stem cell biomarker selected from the group consisting of Cripto, ABCG2, Alkaline Phosphatase/ALPL, CD9, FGF-4, GDF-3, Integrin alpha 6/CD49f, Integrin beta 1/CD29, NANOG, OCT-3/4, Podocalyxin, SOX2, SSEA-3, SSEA-4, STAT3, SSEA-1, FoxD3, DPPA5/ESG1, Rex-1/ZFP42, DPPA4, LIN-28A, UTF1, Lefty-A, Lefty-1, TBX3, ESGP, TRA-1-60(R), TRA-1-81, 5T4, TBX2, ZIC3, CD30/TNFRSF8, KLF5, c-Myc, GCNF/NR6A1, SUZ12, Smad2, CDX2, TROP-2, CD117/c-kit, LIN-41, Integrin alpha 6 beta 4, THAP11, Smad2/3, TBX5, TEX19, Oct-4A, TEX19.1, DPPA2, Activin RIB/ALK-4, Activin RIIB, FGF-5, GBX2, Stella/Dppa3, DNMT3B, F-box protein 15/FBXO15, LIN-28B, Integrin alpha 6 beta 1, KLF4, ERR beta/NR3B2, EpCAM/TROP1, TERT, CHD1, Cbx2, c-Maf, L1TD1, and (ii) the expression of one or more biomarkers associated with the Renin-Angiotensin System.

In yet another aspect of the present invention there is provided a method for preventing, treating, or managing cancer in a patient in need thereof, the method comprising administering a therapeutic agent to the patient in an amount sufficient to selectively eradicate, or inhibit the growth, proliferation and/or differentiation of cancer stem cells within the cancer, wherein the cancer stem cells are characterised by (i) the expression of one or more embryonic stem cell biomarker selected from the group consisting of OCT4, SOX2, NANOG and PSTAT3, and (ii) the expression of one or more biomarkers associated with the Renin-Angiotensin System selected from the group consisting of Renin Receptor (RR), Angiotensin II Receptor 2 and a secreted form of the Renin Receptor (sRR).

In yet a further aspect of the present invention there is provided a method for preventing, treating, or managing cancer in a patient in need thereof, the method comprising administering a therapeutic agent(s) to the patient in an amount sufficient to selectively eradicate or, inhibit the growth, proliferation and/or differentiation of cancer stem cells within the cancer, wherein the cancer stem cells are characterised by (i) the expression of one or more stem cell biomarker selected from the group consisting of Oct-4, SOX2, NANOG and PSTAT3, and (ii) the expression of one or more biomarkers associated with the Renin-Angiotensin System selected from the group consisting of Renin Receptor, Angiotensin II Receptor 2 and a secreted form of the Renin Receptor, and wherein the therapeutic agent is selected from the group consisting of Direct Renin Inhibitors (DRIs), Angiotensin-Converting Enzyme Inhibitors (ACEIs), Angiotensin Receptor Blockers (ARBs), Beta-Blockers, Cyclo-oxygenase 2 Inhibitors, Chymase Inhibitors, Inhibitors of Cathepsin B, Cathepsin D and Cathepsin G, Calcium, Vitamin D, and Calcium Channel Blockers.

In yet another aspect of the present invention there is provided a method for determining presence or absence of cancer in a subject, the method comprising:

(i) detecting and/or measuring the levels of cancer stem cells present in a biological sample obtained from the subject using biomarker expression analysis;

(ii) comparing the levels of the cancer stem cells obtained from the biological sample against the cancer stem cell level from a control population;

wherein, an increased level in the cancer stem cells obtained from the biological sample relative to the control population is diagnostic that the subject has, or is predisposed to developing, cancer.

In another aspect of the present invention there is provided a method for determining presence or absence of cancer in a subject, the method comprising:

(i) detecting and/or measuring the level of cancer stem cells in a biological sample obtained from the subject using biomarker expression analysis;

(ii) comparing the level of the cancer stem cells obtained from the biological sample against the cancer stem cell level from a control population, wherein, an increased level in the cancer stem cells obtained from the biological sample relative to the control population is diagnostic that the subject has, or is predisposed to developing, cancer, and (iii) administering a prophylactic or therapeutic regime(s) to the subject who has, or is predisposed to developing, cancer.

In another aspect of the present invention there is provided a pharmaceutical composition for use in a method for treatment of cancer, wherein the pharmaceutical composition comprises a therapeutic agent sufficient to selectively eradicate or, inhibit the growth, proliferation and/or differentiation of cancer stem cells within a cancer, and wherein the method comprises administering the therapeutic agent to a patient with cancer.

In another aspect of the present invention there is provided a kit or article of manufacture for use in the treatment of cancer, the kit comprising a therapeutic agent sufficient to selectively eradicate, or inhibit the growth, proliferation and/or differentiation of cancer stem cells within a cancer, together with instructions for how to administer a therapeutic dose to the subject.

BRIEF DESCRIPTION OF THE FIGURES

FIG. 5A shows immunohistochemical co-staining using antibodies specific to OCT4 and RR. FIG. 5B shows quantification of the relative fluorescence signal for OCT4 (dots) and RR (long dashed line).

FIG. 7A shows immunohistochemical staining using antibodies specific to OCT4 and RR. FIG. 7B shows quantification of the relative fluorescence signal for OCT4 (dots) and RR (long dashed line).

FIG. 9A shows immunohistochemical staining using antibodies specific to OCT4 and RR. FIG. 9B shows quantification of the relative fluorescence signal for OCT4 (dots) and RR (long dashed line).

FIG. 11A shows immunohistochemical staining using antibodies specific to OCT4 and RR. FIG. 11B shows quantification of the relative fluorescence signal for OCT4 (dots) and RR (long dashed line).

FIG. 13A shows immunohistochemical staining using antibodies specific to OCT4 and RR. FIG. 13B shows quantification of the relative fluorescence signal for OCT4 (dots) and RR (long dashed line).

FIG. 15A shows immunohistochemical staining using antibodies specific to OCT4 and RR. FIG. 15B shows quantification of the relative fluorescence signal for OCT4 (dots) and RR (long dashed line).

FIG. 17A shows immunohistochemical staining using antibodies specific to OCT4 and RR. FIG. 17B shows quantification of the relative fluorescence signal for OCT4 (dots) and RR (long dashed line).

FIG. 19A shows immunohistochemical staining using antibodies specific to OCT4 and RR. FIG. 19B shows quantification of the relative fluorescence signal for OCT4 (dots) and RR (long dashed line).

FIG. 21A shows immunohistochemical staining using antibodies specific to OCT4 and RR. FIG. 21B shows quantification of the relative fluorescence signal for OCT4 (dots) and RR (long dashed line).

FIGS. 23A and 23B shows the co-localisation of OCT4 and RR by the cancer stem cell population associated with thyroid cancer. FIG. 23A shows immunohistochemical staining using antibodies specific to OCT4 and RR. FIG. 23B shows quantification of the relative fluorescence signal for OCT4 (dots) and RR (long dashed line).

FIG. 25A shows immunohistochemical staining using antibodies specific to OCT4 and RR. FIG. 25B shows quantification of the relative fluorescence signal for OCT4 (dots) and RR (long dashed line).

FIG. 27A shows immunohistochemical staining using antibodies specific to OCT4 and RR. FIG. 27B shows quantification of the relative fluorescence signal for OCT4 (dots) and RR (long dashed line).

FIG. 29A shows immunohistochemical staining using antibodies specific to OCT4 and RR. FIG. 29B shows quantification of the relative fluorescence signal for OCT4 (dots) and RR (long dashed line).

SELECTED DEFINITIONS

Figure 1:
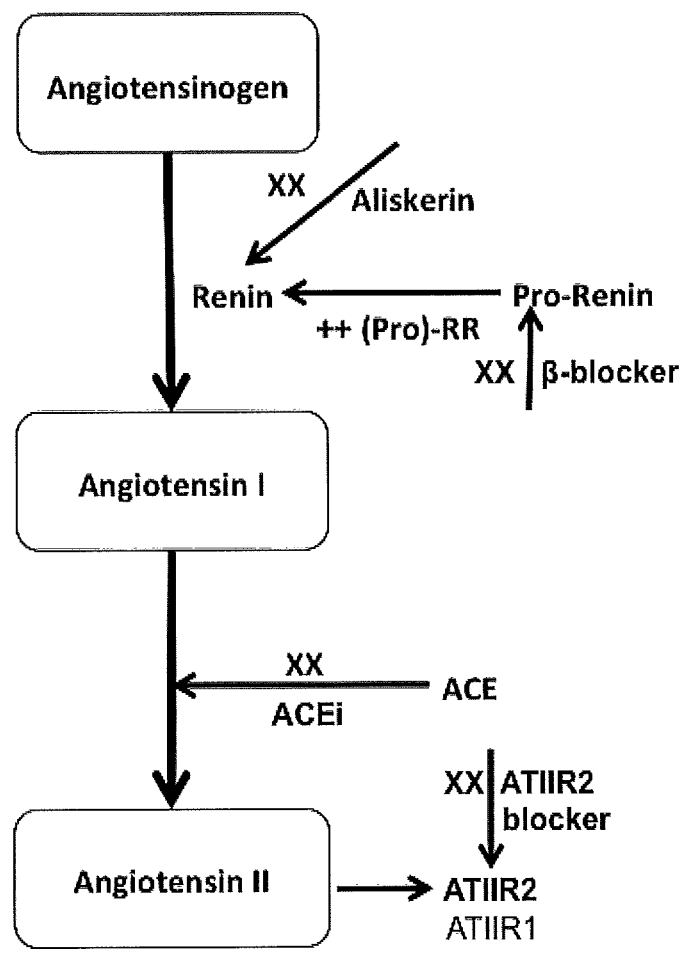
FIG. 1 shows the main pathways associated with the RAS. ACE: Angiotensin Converting Enzyme; ACEIs: Angiotensin Converting Enzyme inhibitors; Cox2i: Cox2 inhibitors; β-blockers: Beta-Blockers; ATIIR2: Angiotensin II Receptor 2; ATIIR1: Angiotensin II Receptor 1; (Pro)-RR: Pro(Renin) Receptors [also called Renin Receptor (RR)]; Vit D: Vitamin D; XX: major blockades; ++: major promoting steps.

Unless defined otherwise, all technical and scientific terms used herein have the same meaning as commonly understood to one of ordinary skill in the art to which the inventions belong. Although any assays, methods, devices and materials similar or equivalent to those described herein can be used in the practice or testing of the invention, various assays, methods, devices and materials are now described.

It is intended that reference to a range of numbers disclosed herein (for example 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

As used in this specification, the words "comprises", "comprising", and similar words, are not to be interpreted in an exclusive or exhaustive sense. In other words, they are intended to mean "including, but not limited to".

As used herein, the term "antibodies" refer to molecules that contain an antigen binding site, e.g., immunoglobulins.

Immunoglobulin molecules can be of any type (e.g., IgG, IgE, IgM, IgD, IgA and IgY), class (e.g., IgG1, IgG2, IgG3, IgG4, IgA1 and IgA2) or subclass. Antibodies include, but are not limited to, monoclonal antibodies, polyclonal antibodies, multispecific antibodies, human antibodies, humanised antibodies, murine antibodies, camelised antibodies, chimeric antibodies, single domain antibodies, single chain Fvs (scFv), single chain antibodies, Fab fragments, F(ab') fragments, disulfide-linked Fvs (sdFv), and anti-idiotopic (anti-Id) antibodies (including, e.g., anti-Id antibodies to antibodies of the invention), and epitope-binding fragments of any of the above.

As used herein, the term "cancer" refers to a neoplasm or tumour resulting from abnormal uncontrolled growth of cells. The term "cancer" encompasses a disease involving both pre-malignant and malignant cancer cells. In some examples, cancer refers to a localised overgrowth of cells that has not spread to other parts of a subject, i.e., a benign tumour. In other examples, cancer refers to a malignant tumour, which has invaded and destroyed neighboring body structures and/or spread to distant sites.

As used herein, the term "cancer cells" refer to cells that acquire a characteristic set of functional capabilities during their development, including the ability to evade apoptosis, are self-sufficienct in growth signals and are insensitivite to anti-growth signals, tissue invasion/metastasis, significant growth potential, and/or sustained angiogenesis. The term "cancer cell" is meant to encompass both pre-malignant and malignant cancer cells.

As used herein, the term "cancer stem cell(s)" refers to a cell that can be a progenitor of a highly proliferative cancer cell. A cancer stem cell has the ability for assymmetrical division and to re-grow a tumour as demonstrated by its ability to form tumours in immunocompromised mice, and typically to form tumours upon subsequent serial transplantation in immunocompromised mice. Cancer stem cells are also typically slow-growing relative to the bulk of a tumour; that is, cancer stem cells are generally quiescent. In certain examples, but not all, the cancer stem cell may represent approximately 0.1 to 10% of a tumour.

As used herein, the term "cancer stem cell population" is intended to mean one or more cancer stem cells, in other words a single cancer stem cell or multiple cancer stem cells, the single cancer stem cell or multiple cancer stem cells being capable of driving tumourigenesis of a given cancer.

As used herein, the term "squamous cell carcinomas" refers to the epithelial tumours found in many different organs, including the skin, upper aerodigestive tract (including oral cavity) and paranasal sinuses, oesophagus, lungs, and cervix, and other organs which show squamous cell differentiation. Included are head and neck squamous cell carcinomas, lung squamous cell carcinomas, skin squamous cell carcinomas, otic squamous cell carcinomas, vulval squamous cell carcinomas, cervical squamous cell carcinomas, oesophageal squamous cell carcinomas, upper aerogigestive tract and paranasal sinus squamous cell carcinomas and the like.

As used herein, the term "Renin-Angiotensin System (RAS)" or "Renin-Angiotensin-Aldosterone System (RAAS)" is a hormone system that regulates blood pressure and fluid balance. The wider pathway associated with RAS also includes the Pro/Renin Receptor System (PRRS) and the associated bypass pathways. By way of example, refer to FIGS. 1 and 2. There are a number of known drugs which target the RAS including PRRS, as described in more detail below.

As used herein, the term "effective amount" refers to the amount of a therapy that is sufficient to result in the prevention of the development, recurrence, or onset of cancer and one or more symptoms thereof, to enhance or improve the prophylactic effect(s) of another therapy, reduce the severity, the duration of cancer, ameliorate one or more symptoms of cancer, prevent the advancement of cancer, cause regression of cancer, and/or enhance or improve the therapeutic effect(s) of another therapy. In an example of the invention, the amount of a therapy is effective to achieve one, two or three or more results following the administration of one, two, three or more therapies: (1) a stabilisation, reduction or eradication of the cancer stem cell population; (2) a stabilisation, reduction or eradication in the cancer cell population; (3) a stabilisation or reduction in the growth of a tumour or neoplasm; (4) an impairment in the formation of a tumour; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalisation rate, (10) a decrease in hospitalisation lengths, (11) the size of the tumour is maintained and does not increase or increases by less than 10%, preferably less than 5%, preferably less than 4%, preferably less than 2%, (12) an increase in the number of patients in remission, (13) an increase in the length or duration of remission, (14) a decrease in the recurrence rate of cancer, (15) an increase in the time to recurrence of cancer, and (16) an amelioration of cancer-related symptoms and/or quality of life.

As used herein, the terms "manage", "managing", and "management" in the context of the administration of a therapy to a subject refer to the beneficial effects that a subject derives from a therapy (e.g., a prophylactic or therapeutic agent) or a combination of therapies, while not resulting in a cure of cancer. In certain examples, a subject is administered one or more therapies (e.g., one or more prophylactic or therapeutic agents) to "manage" cancer so as to prevent the progression or worsening of the condition.

As used herein, the terms "prevent", "preventing" and "prevention" in the context of the administration of a therapy to a subject refers to the prevention or inhibition of the recurrence, onset, and/or development of a cancer or a symptom thereof in a subject resulting from the administration of a therapy (e.g., a prophylactic or therapeutic agent), or a combination of therapies (e.g., a combination of prophylactic or therapeutic agents). In some examples, such terms refer to one, two, three or more results following the administration of one or more therapies: (1) a stabilisation, reduction or eradication of the cancer stem cell population, (2) a stabilisation, reduction or eradication of the cancer cell population, (3) an increase in the response rate, (4) an increase in the duration of remission, (5) a decrease in the recurrence rate of cancer, (6) an increase in the time to recurrence of cancer, (7) an increase in the disease-free, relapse-free, progression-free, and/or overall survival of the patient, and (8) an amelioration of cancer-related symptoms and/or quality of life. In specific examples, such terms refer to a stabilisation, reduction or eradication of the cancer stem cell population.

As used herein, the term "marker" or "biomarker" in the context of a tissue (e.g. a normal cell or tumour cell) means any antigen, molecule or other chemical or biological entity that is specifically found in or on a tissue that it is desired to be identified or identified in or on a particular tissue affected by a disease or disorder, for example cancer. The term "tumourigenic biomarker" is also relevant to this definition in the context of cancer. In specific examples, the marker is a cell surface antigen that is differentially or preferentially expressed by specific cell types. In specific examples, the marker is a nuclear antigen that is differentially or preferentially expressed by specific cell types. In specific examples the marker is an intracellular antigen that is differentially or preferrentially expressed by specific cell types.

As used herein, the term "prophylactic agent" refers to any molecule, compound, and/or substance that is used for the purpose of preventing cancer. Examples of prophylactic agents include, but are not limited to, proteins, immunoglobulins (e.g., multi-specific Igs, single chain Igs, Ig fragments, polyclonal antibodies and their fragments, monoclonal antibodies and their fragments), antibody conjugates or antibody fragment conjugates, peptides (e.g., peptide receptors, selectins), binding proteins, chemospecific agents, chemotoxic agents (e.g., anti-cancer agents), proliferation based therapy, and small molecule drugs.

As used herein, the term "therapeutic agent" refers to any molecule, compound, and/or substance that is used for the purpose of treating and/or managing a disease or disorder. Examples of therapeutic agents include, but are not limited to, proteins, immunoglobulins (e.g., multi-specific Igs, single chain Igs, Ig fragments, polyclonal antibodies and their fragments, monoclonal antibodies and their fragments), peptides (e.g., peptide receptors, selectins), binding proteins, biologies, chemospecific agents, chemotoxic agents (e.g., anti-cancer agents), proliferation-based therapy agents, hormonal agents, radioimmunotherapies, targeted agents, epigenetic therapies, differentiation therapies, biological agents, radiation agents, chemotherapy, anti-angiogenic agents, and small molecule drugs.

As used herein, the terms "therapies" and "therapy" can refer to any method(s), composition(s), and/or agent(s) that can be used in the prevention, treatment and/or management of a cancer or one or more symptoms thereof. In certain examples, the terms "therapy" and "therapies" refer to chemotherapy, radiation therapy, surgery, hormonal therapy, anti-angiogenic therapy, biological therapy, proliferation based therapy, prodrug-activating enzyme therapy, small molecule therapy, toxin therapy, antibody therapy, immunotherapy, radioimmunotherapy, targeted therapy, epigenetic therapy, demethylation therapy, histone deactylase inhibitor therapy, differentiation therapy and/or other therapies useful in the prevention, management and/or treatment of a cancer or one or more symptoms thereof.

As used herein, the terms "treat", "treatment" and "treating" in the context of the administration of a therapy to a subject refer to the reduction or inhibition of the progression and/or duration of cancer, the reduction or amelioration of the severity of cancer, and/or the amelioration of one or more symptoms thereof resulting from the administration of one or more therapies. In specific examples, such terms refer to one, two or three or more results following the administration of one, two, three or more therapies: (1) a stabilization, reduction or eradication of the cancer stem cell population; (2) a stabilisation, reduction or elimination in the cancer cell population; (3) a stabilisation or reduction in the growth of a tumour or neoplasm; (4) an impairment in the formation of a tumour; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalisation rate, (10) a decrease in hospitalisation lengths, (11) the size of the tumour is maintained and does not increase or increases by less than 10%, preferably less than 5%, preferably less than 4%, preferably less than 2%, and (12) an increase in the number of patients in remission. In certain examples, such terms refer to a stabilisation or reduction in the cancer stem cell population. In some examples, such terms refer to a stabilisation or reduction in the growth of cancer cells. In some examples, such terms refer to a stabilisation or reduction in the cancer stem cell population and a reduction in the cancer cell population. In some examples, such terms refer to a stabilisation or reduction in the growth and/or formation of a tumour. In some examples, such terms refer to the eradication, removal, or control of primary, regional, or metastatic cancer (e.g., the minimisation or delay of the spread of cancer). In some examples, such terms refer to a reduction in mortality and/or an increase in survival rate of a patient population. In further examples, such terms refer to an increase in the response rate, the durability of response, or number of patients who respond or are in remission. In some examples, such terms refer to a decrease in hospitalisation rate of a patient population and/or a decrease in hospitalisation length for a patient population.

The term "sample" or "biological sample" as used herein means any sample taken or derived from a subject. Such a sample may be obtained from a subject, or may be obtained from biological materials intended to be provided to the subject. For example, a sample may be obtained from blood being assessed, for example, to investigate the cancer status of a subject. Included are samples taken or derived from any subjects such as from normal healthy subjects and/or healthy subjects for whom it is useful to understand their cancer status. Preferred samples are biological fluid samples. The term "biological fluid sample" as used herein refers to a sample of bodily fluid obtained for the purpose of, for example, diagnosis, prognosis, classification or evaluation of a subject of interest, such as a patient. In certain embodiments, such a sample may be obtained for the purpose of determining the cancer status of a patient. The sample may be any sample known in the art in which cancer stem cells may be detected. Included are any body fluids such as a whole blood sample, plasma, serum, ovarian follicular fluid sample, seminal fluid sample, cerebrospinal fluid, saliva, sputum, urine, pleural effusions, interstitial fluid, synovial fluid, lymph, tears, for example, although whole blood sample, plasma and serum are particularly suited for use in this invention. In addition, one of skill in the art would realise that certain body fluid samples would be more readily analysed following a fractionation or purification procedure, for example, separation of whole blood into serum or plasma components.

The term "purified" as used herein does not require absolute purity. Purified refers in one embodiment to at least 90%, or 95%, or 98%, or 99% homogeneity of, to provide an example, of a polypeptide or antibody in a sample.

The term "subject" as used herein is preferably a mammal and includes human, and non-human mammals such as cats, dogs, horses, cows, sheep, deer, mice, rats, primates (including gorillas, rhesus monkeys and chimpanzees), possums and other domestic farm or zoo animals. Thus, the assays, methods and kits described herein have application to both human and non-human animals, in particular, and without limitation, humans, primates, farm animals including cattle, sheep, goats, pigs, deer, alpacas, llamas, buffalo, companion and/or pure bred animals including cats, dogs and horses. Preferred subjects are humans, and most preferably "patients" who as used herein refer to living humans who may receive or are receiving medical care or assessment for a disease or condition. Further, while a subject is preferably a living organism, the invention described herein may be used in post-mortem analysis as well.

The term "ELISA" as used herein means an enzyme linked immunosorbent assay, a type of competitive binding assay comprising antibodies and a detectable label used to quantitate the amount of an analyte in a sample.

The term "capture antibody" as used herein means an antibody which is typically immobilized on a solid support such as a plate, bead or tube, and which antibody binds to and captures analyte(s) of interest, for example membrane bound markers associated with a cancer stem cell population.

The term "detection antibody" as used herein means an antibody comprising a detectable label that binds to analyte(s) of interest. The label may be detected using routine detection means for a quantitative, semi-quantitative or qualitative measure of the analyte(s) of interest, for example membrane bound markers associated with a cancer stem cell population.

As used herein, the term "relating to the presence or amount" of an analyte reflects that assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Typically, an analyte is measured in a sample.

A level "higher" or "lower" than a control, or a "change" or "deviation" from a control (level) in one embodiment is statistically significant. A higher level, lower level, deviation from, or change from a control level or mean or historical control level can be considered to exist if the level differs from the control level by about 5% or more, by about 10% or more, by about 20% or more, or by about 50% or more compared to the control level. Statistically significant may alternatively be calculated as P≤0.05. Higher levels, lower levels, deviation, and changes can also be determined by recourse to assay reference limits or reference intervals. These can be calculated from intuitive assessment or non-parametric methods. Overall, these methods may calculate the 0.025, and 0.975 fractiles as 0.025*(n+1) and 0.975 (n+1). Such methods are well known in the art. Presence of a marker absent in a control may be seen as a higher level, deviation or change. Absence of a marker present in a control may be seen as a lower level, deviation or change.

DETAILED DESCRIPTION

There is an emerging concept that cancer stem cells drive the persistence or recurrence of a tumour. Conventional cancer therapies, while successful in eradicating the bulk of tumours, are typically less effective on insidious cancer stem cells. Further, selective drug resistance exhibited by these cells contributes to significant morbidity and mortality in cancer sufferers. Accordingly, there is a need for therapeutic regimes that specifically and selectively target cancer stem cells.

The present invention is predicated on the surprising and unexpected discovery that discrete cancer stem cell populations are associated with certain tumours including (e.g., squamous cell carcinoma of the oral cavity, squamous cell carcinoma of the skin, melanoma, lung cancer, breast cancer, kidney cancer, brain cancer, bowel cancer, thyroid cancer, prostate cancer, lymphoma, leukaemia and sarcomas. The cancer stem cell populations associated with these tumours are characterised by unique biomarker expression profiles that allows for the specific identification and diagnosis of certain cancers.

Importantly, it has also been revealed by the Applicants that these cancer stem cell populations express key components of the Renin-Agiotensin System (RAS), including the Renin Receptor (RR) Angiotensin II Receptor 2 (ATIIR2), as well as a secreted form of the Renin Receptor (sRR). In reference to FIGS. 3, 6, 8, 10, 12, 14, 16, 18, 20, 22, 24, 26 and 28, the Applicants demonstrate co-expression of RR and ATIIR2 by the cancer stem cell populations associated with various tumours. These cancer stem cell populations are characterised by, for example, the expression of OCT4, SOX2, PSTAT3 and NANOG. Accordingly, the expression of the components of RAS by these cancer stem cell populations provides a novel and unique therapeutic approach by targeting the cancer stem cells associated with various tumours from the extensive array of drugs that target RAS such as, Angiotensin-Converting Enzyme Inhibitors (ACEis), Angiotensin Receptor Blockers (ARBs), Direct Renin Inhibitors (DRIs), Beta-Blockers, Cyclo-oxygenase 2 Inhibitors, Chymase Inhibitors, Inhibitors of Cathepsin B, Cathepsin D and Cathepsin G, Calcium Supplements, Vitamin D and Calcium Channel Blockers.

In addition, the present invention also contemplates indirect inhibitors of the RAS (e.g., Calcium Channel Blockers).

Accordingly, in one aspect of the present invention there is provided a method for preventing, treating, or managing cancer in a patient in need thereof, the method comprising administering a therapeutic agent to the patient in an amount sufficient to selectively eliminate or inhibit the growth, proliferation and/or differentiation of cancer stem cells in a tumour associated with the cancer, wherein the cancer stem cells are characterised by (i) the expression of one or more embryonic stem cell biomarkers, and (ii) the expression of one or more biomarkers associated with the Renin-Angiotensin System.

In another aspect of the present invention there is provided a method for preventing, treating, or managing cancer in a patient in need thereof, the method comprising administering a therapeutic agent to the patient in an amount sufficient to selectively inhibit the growth, proliferation and/or differentiation of cancer stem cells within the cancer, wherein the cancer stem cells are characterised by (i) the expression of one or more embryonic stem cell biomarkers, and (ii) the expression of one or more biomarkers associated with the Renin-Angiotensin System, and wherein the cancer is a solid tumour or blood cancer.

In one example, the one or more embryonic stem cell markers is selected from the group consisting of Cripto, ABCG2, Alkaline Phosphatase/ALPL, CD9, FGF-4, GDF-3, Integrin alpha 6/CD49f, Integrin beta 1/CD29, Nanog, Oct-3/4, Podocalyxin, SOX2, SSEA-3, SSEA-4, STAT3, SSEA-1, FoxD3, DPPA5/ESG1, Rex-1/ZFP42, DPPA4, LIN-28A, UTF1, Lefty-A, Lefty-1, TBX3, ESGP, TRA-1-60(R), TRA-1-81, 5T4, TBX2, ZIC3, CD30/TNFRSF8, KLF5, c-Myc, GCNF/NR6A1, SUZ12, Smad2, CDX2, TROP-2, CD117/c-kit, LIN-41, Integrin alpha 6 beta 4, THAP11, Smad2/3, TBX5, TEX19, Oct-4A, TEX19.1, DPPA2, Activin RIB/ALK-4, Activin RIIB, FGF-5, GBX2, Stella/Dppa3, DNMT3B, F-box protein 15/FBXO15, LIN-28B, Integrin alpha 6 beta 1, KLF4, ERR beta/NR3B2, EpCAM/TROP1, TERT, CHD1, Cbx2, c-Maf and L1TD1. In another example, the one or more embryonic stem cell biomarkers consists in OCT4, SOX2, NANOG and PSTAT3. In yet another example, the one or more biomarkers associated with the RAS is selected from the group consisting of RR, ATIIR2, and sRR.

In yet another aspect of the present invention there is provided a method for preventing, treating, or managing cancer in a patient in need thereof, the method comprising administering a therapeutic agent to the patient in an amount sufficient to selectively eradicate, or inhibit the growth, proliferation and/or differentiation of cancer stem cells within the cancer, wherein the cancer stem cells are characterised by (i) the expression of one or more embryonic stem cell biomarkers, and (ii) the expression of one or more biomarkers associated with the Renin-Angiotensin System, and wherein the tumour is selected from the group consisting of squamous cell carcinoma of the oral cavity, squamous cell carcinoma of the skin, melanoma, lung cancer, breast cancer, kidney cancer, brain cancer, bowel cancer, thyroid cancer, prostate cancer, lymphoma, leukaemia and sarcomas.

In yet a further aspect of the present invention there is provided a method for preventing, treating, or managing cancer in a patient in need thereof, the method comprising administering a therapeutic agent to the patient in an amount sufficient to selectively eradicate, or inhibit the growth, proliferation and/or differentiation of cancer stem cells in a tumour associated with the cancer, wherein the cancer stem cells are characterised by (i) the expression of one or more embryonic stem cell biomarkers, and (ii) the expression of one or more biomarkers associated with the Renin-Angiotensin System, and wherein the tumour is a squamous cell carcinoma.

In another aspect of the present invention there is provided a method for preventing, treating, or managing cancer in a patient in need thereof, the method comprising administering a therapeutic agent to the patient in an amount sufficient to selectively eliminate, or inhibit the growth, proliferation and/or differentiation of cancer stem cells in a tumour associated with the cancer, wherein the cancer stem cells are characterised by (i) the expression of one or more stem cell biomarker selected from the group consisting of Cripto, ABCG2, Alkaline Phosphatase/ALPL, CD9, FGF-4, GDF-3, Integrin alpha 6/CD49f, Integrin beta 1/CD29, NANOG, OCT3/4, Podocalyxin, SOX2, SSEA-3, SSEA-4, STAT3, SSEA-1, FoxD3, DPPA5/ESG1, Rex-1/ZFP42, DPPA4, LIN-28A, UTF1, Lefty-A, Lefty-1, TBX3, ESGP, TRA-1-60(R), TRA-1-81, 5T4, TBX2, ZIC3, CD30/TNFRSF8, KLF5, c-Myc, GCNF/NR6A1, SUZ12, Smad2, CDX2, TROP-2, CD117/c-kit, LIN-41, Integrin alpha 6 beta 4, THAP11, Smad2/3, TBX5, TEX19, Oct-4A, TEX19.1, DPPA2, Activin RIB/ALK-4, Activin RIIB, FGF-5, GBX2, Stella/Dppa3, DNMT3B, F-box protein 15/FBXO15, LIN-28B, Integrin alpha 6 beta 1, KLF4, ERR beta/NR3B2, EpCAM/TROP1, TERT, CHD1, Cbx2, c-Maf and L1TD1, and (ii) the expression of one or more biomarkers associated with the Renin-Angiotensin System.

In yet another aspect of the present invention there is provided a method for preventing, treating, or managing cancer in a patient in need thereof, the method comprising administering a therapeutic agent to the patient in an amount sufficient to selectively eliminate, or inhibit the growth, proliferation and/or differentiation of cancer stem cells in a tumour associated with the cancer, wherein the cancer stem cells are characterised by (i) the expression of one or more stem cell marker selected from the group consisting of OCT4, SOX2, NANOG and PSTAT3, and (ii) the expression of one or more biomarkers associated with the Renin-Angiotensin System selected from the group consisting of Renin Receptor, Angiotensin II Receptor 2, and a secreted for of the Renin Receptor.

In yet a further aspect of the present invention there is provided a method for preventing, treating, or managing cancer in a patient in need thereof, the method comprising administering a therapeutic agent to the patient in an amount sufficient to selectively eradicate, or inhibit the growth, proliferation and/or differentiation of cancer stem cells in a tumour associated with the cancer, wherein the cancer stem cells are characterised by (i) the expression of one or more stem cell biomarker selected from the group consisting of OCT4, SOX2, NANOG and PSTAT3, and (ii) the expression of Renin Receptor, Angiotensin II Receptor 2 and/or a secreted form of Renin Receptor, and wherein the therapeutic agent is selected from the group consisting of Direct Renin Inhibitors (DRIs), ACEis, ARBs, Beta-Blockers, Cyclo-oxygenase 2 Inhibitors, Chymase Inhibitors, Inhibitors of Cathepsin B, Cathepsin D and Cathepsin G, Calcium, Vitamin D, and Calcium Channel Blockers.

In one example, the cancer stem cells are characterised by the expression of SOX2, OCT4, PSTAT3 and NANOG. These cells are said to have a marker expression profile: SOX2$^+$Oct-4$^+$PSTAT3$^+$NANOG$^+$.

In a related example, the cancer stem cells are cancer stem cells of squamous cell carcinoma of oral tongue and are characterised by the marker expression profile CD44$^+$SOX2$^+$OCT4$^+$NANOG$^+$. In a further example, the cancer stem cells of squamous cell carcinoma of oral tongue are characterised by the marker expression profile CD44$^+$SOX2$^+$OCT4$^+$NANOG$^+$CD34$^-$. In yet a further example, the cancer stem cells are cancer stem cells of squamous cell carcinoma of oral tongue and are characterised by the marker expression profile CD44$^+$SOX2$^+$OCT4$^+$NANOG$^+$CD34$^-$p63$^-$EMA$^-$.

The cancer stem cells may co-express with embryonic stem cell markers, lymphatic cell markers, epithelial cancer cell markers or any combination thereof. Accordingly, in one example, the cancer stem cells co-express with embryonic stem cell markers and epithelial cancer cell markers. In another example, the cancer stem cells co-express with lymphatic cell markers and epithelial cancer cell markers. In a further example, the cancer stem cells co-express with embryonic stem cell markers, lymphatic cell markers, and epithelial cancer cell markers.

Figure 25A:
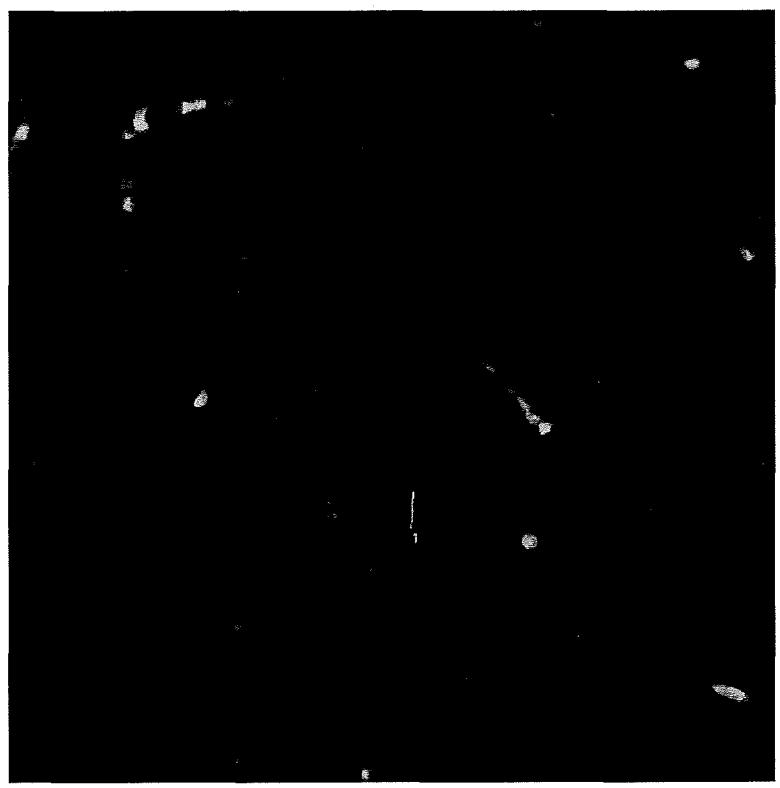
FIGS. 25A and 25B shows the co-localisation of OCT4 and RR by the cancer stem cell population associated with chronic lymphocytic leukaemia.
Figure 25B:
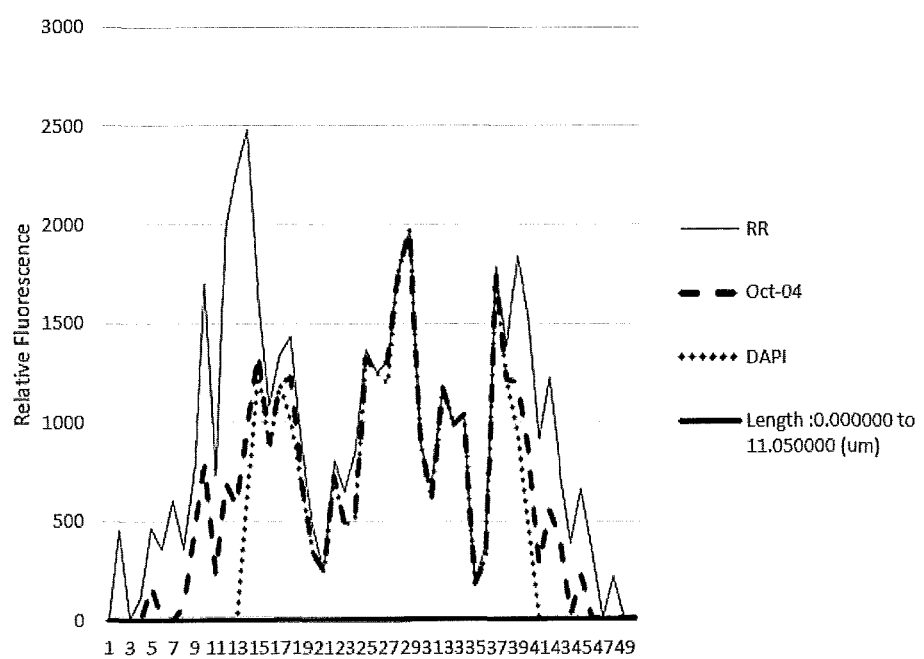
Figure 26:
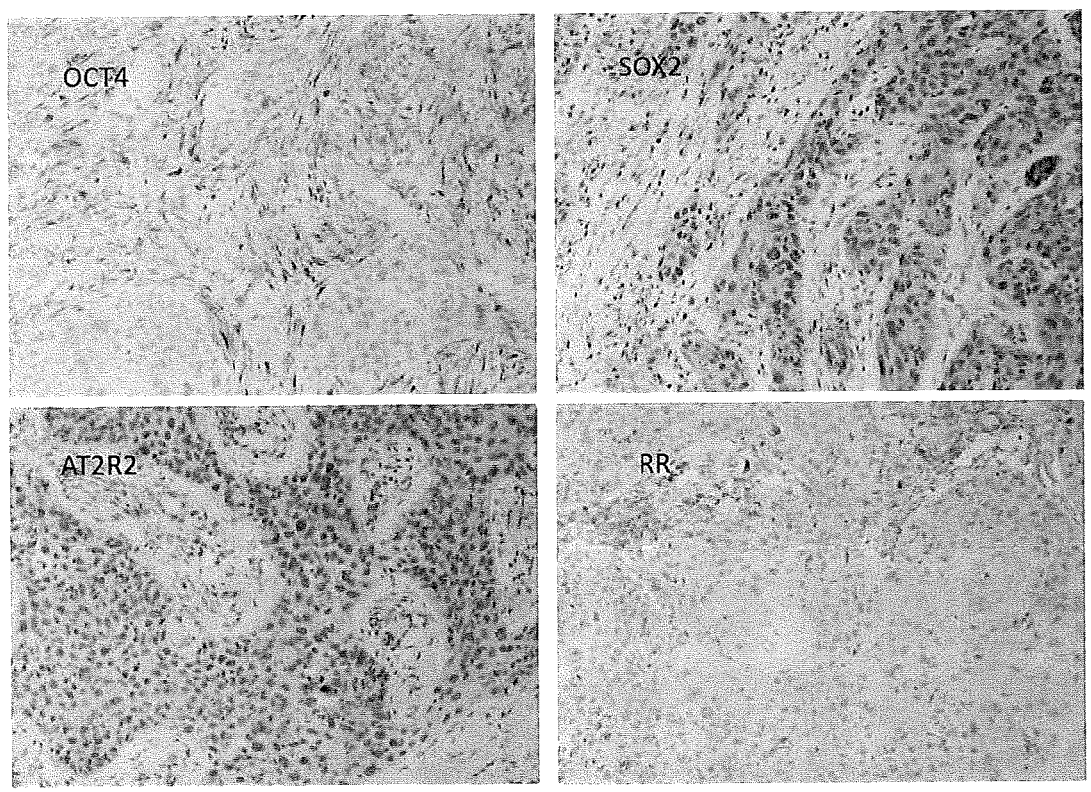
FIG. 26 shows the expression of OCT4, SOX2, ATIIR2 and RR by the cancer stem cell population associated with skin squamous cell carcinoma as evidenced by the immunohistochemical staining profiles.
Figure 27A:
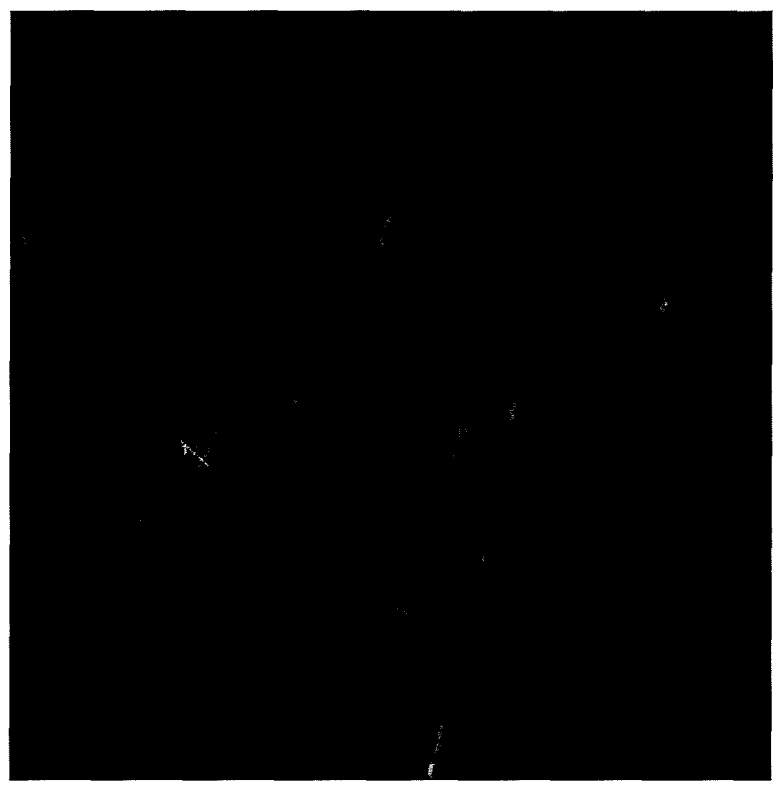
FIGS. 27A and 27B shows the co-localisation of OCT4 and RR by the cancer stem cell population associated with skin squamous cell carcinoma.
Figure 27B:
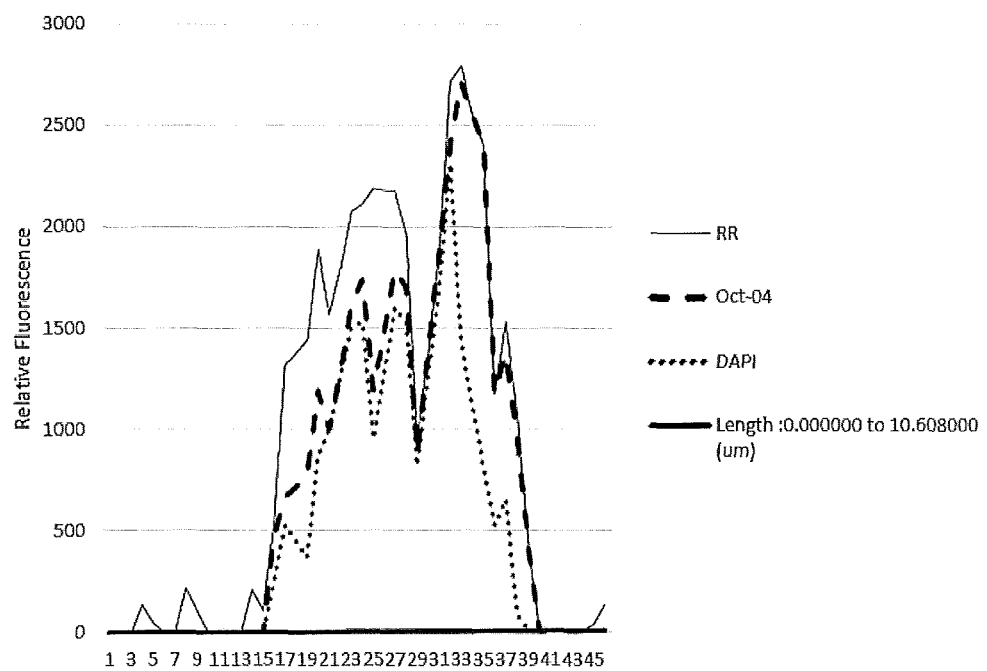
Figure 28:
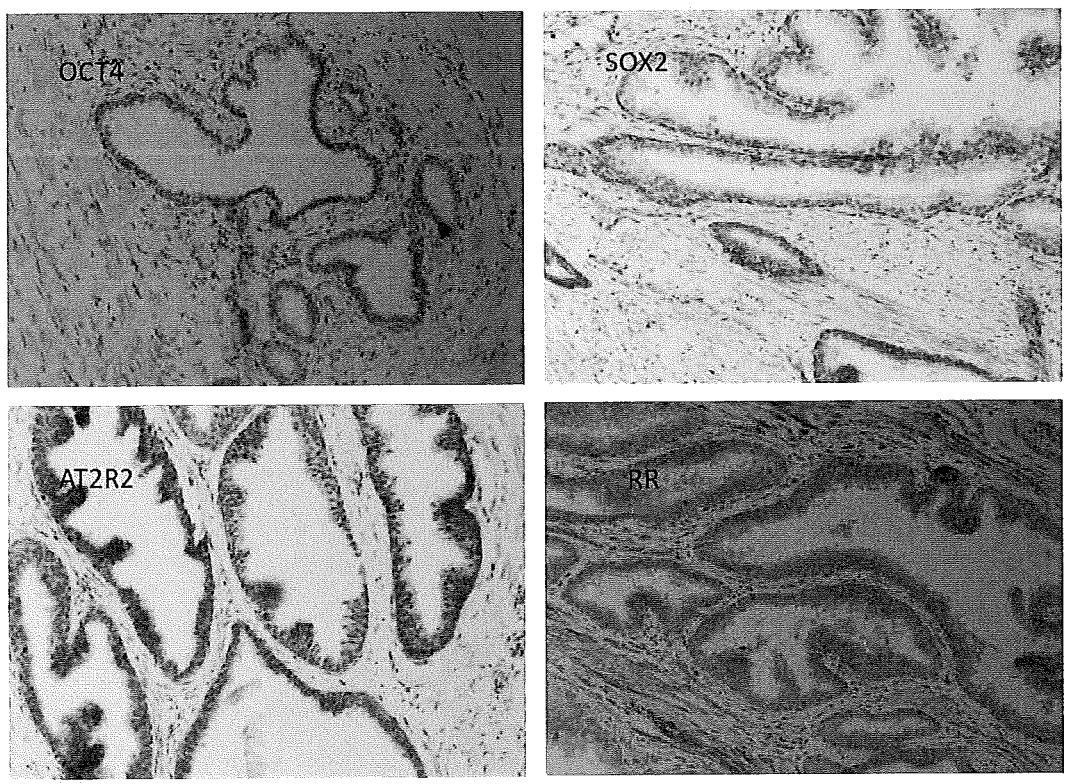
FIG. 28 shows the expression of OCT4, SOX2, ATIIR2 and RR by the cancer stem cell population associated with prostate cancer as evidenced by the immunohistochemical staining profiles.
Figure 29A:
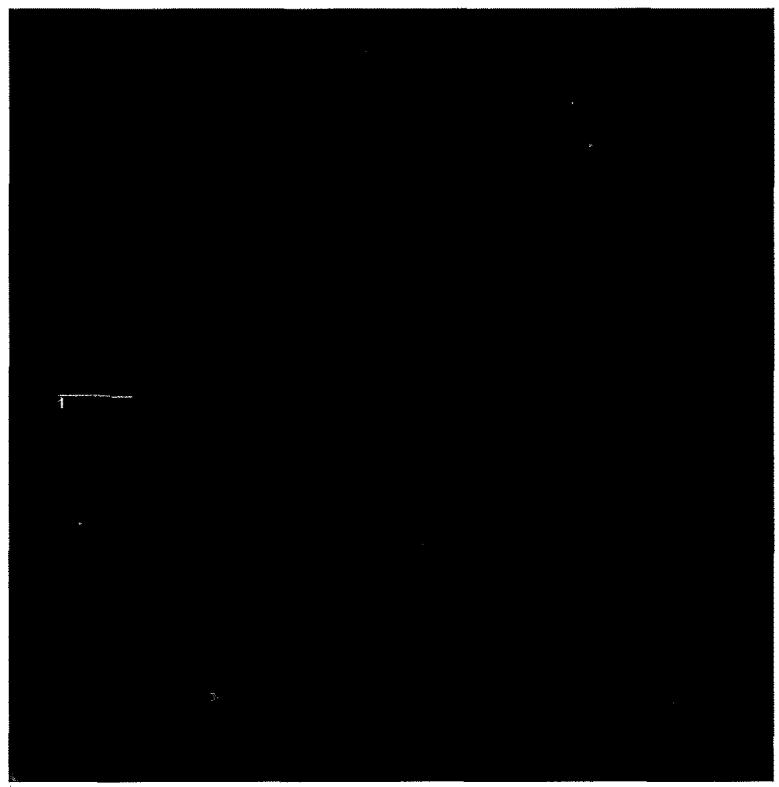
FIGS. 29A and 29B shows the co-localisation of OCT4 and RR by the cancer stem cell population associated with prostate cancer.
Figure 29B:
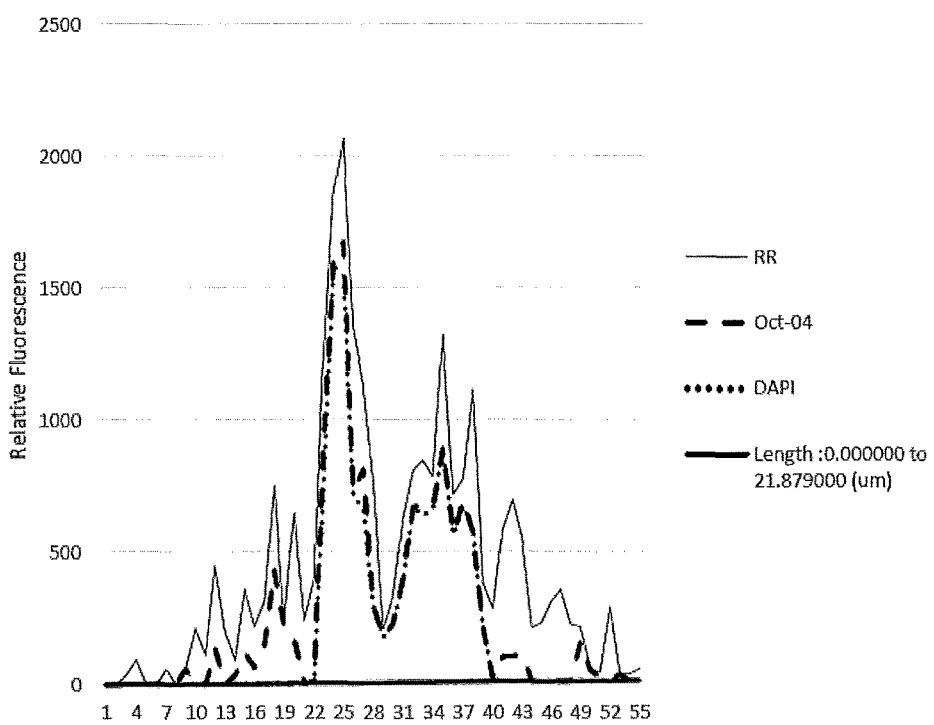
Figure 30:
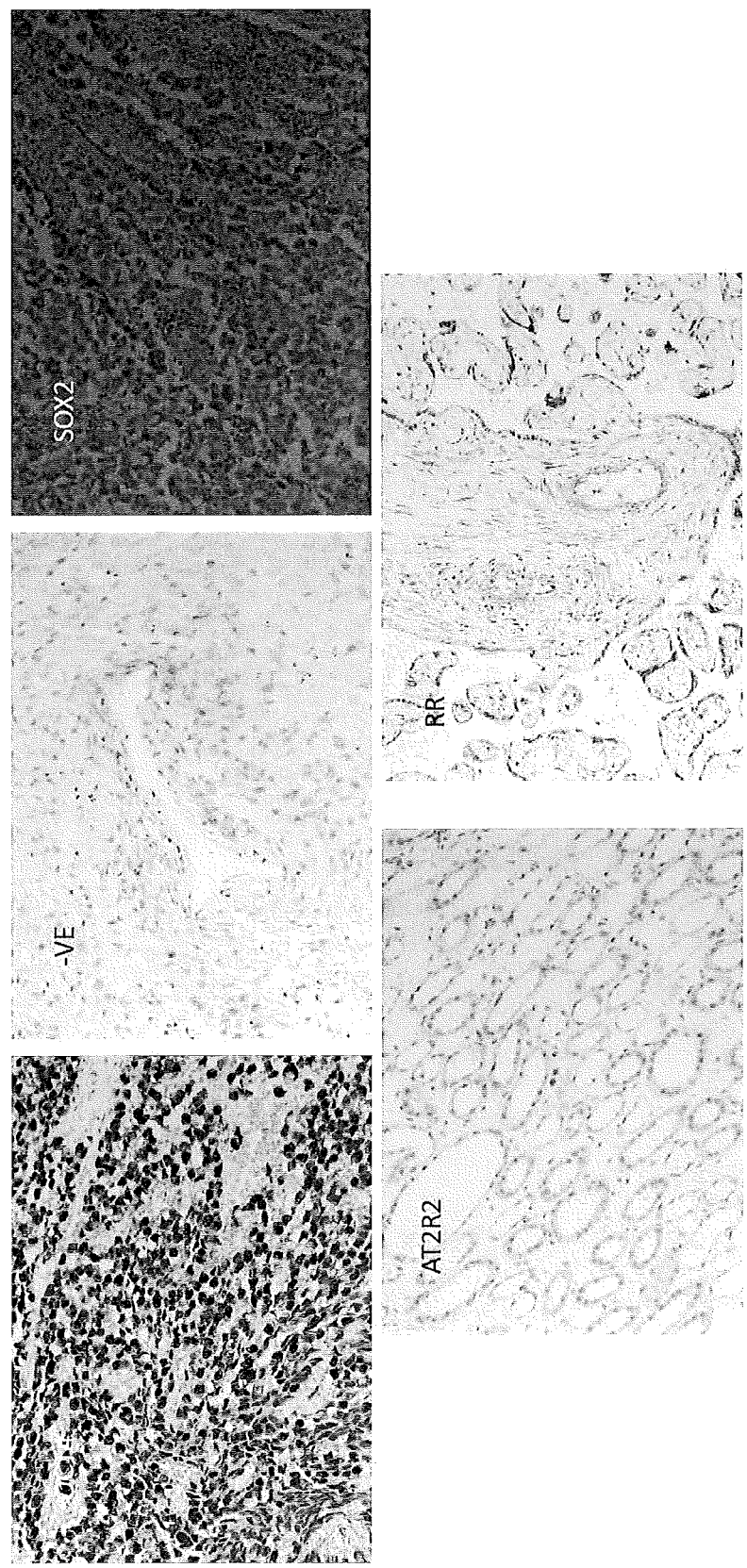
FIG. 30 shows the expression of OCT4 and SOX2 in a human seminoma tissue sample, ATIIR2 in human kidney and RR in human placental tissues as respective positive controls. The negative control shows absence of staining without the primary antibody in a brain cancer (glioblastoma multiforme) tissue section.

While the present invention is particularly relevant to solid tumours, it also extends to blood cancers. For example, the Applicants demonstrate that Chronic Lymphocytic Leukaemia comprise cancer stem cells as characterised by the expression of OCT4, SOX2, ATIIR2 and RR (FIG. 24), which cancer stem cells also co-express the RR and ATIIR2 (FIGS. 25A and 25B). Accordingly, the therapeutic methods and compositions according to the present invention extend to blood cancers as well.

Accordingly, the present invention provides compositions and methods related to identifying and targeting the growth and proliferation of cancer stem cells as the cause of tumour growth, spread and metastasis. In particular, the compositions and methods are directed to cancer stem cells which display unique tumouriogenic biomarker expression profiles. By specifically targeting cancer stem cells, it is assumed that the tumourigenic and metastatic potential of the (nascent or established) tumour is significantly diminished, thereby leading to enhanced therapeutic outcomes.

The cancer stem cells may be associated with a variety of cancers, including but not limited to, squamous cell carcinoma of the upper aerodigestive tract (including oral cavity), squamous cell carcinoma of the skin, melanoma, lung cancer, breast cancer, kidney cancer, brain cancer, bowel cancer, thyroid cancer, prostate cancer, lymphoma, leukemia and sarcomas.

Squamous cell carcinomas include head and neck squamous cell carcinomas (including squamous cell carcinomas of the upper aerodigestive tract [including oral cavity] and paranasal sinuses and elsewhere), oesophageal squamous cell carcinomas, skin squamous cell carcinomas, lung squamous cell carcinomas, vulval squamous cell carcinomas and cervical squamous cell carcinomas. In one example the upper aerodigestive tract squamous cell carcinoma is squamous cell carcinoma of oral tongue.

The present invention provides methods for preventing, treating, and/or managing cancer, the method comprising administering to a subject in need thereof a course of therapy that stabilises, reduces, or eradicate the cancer stem cell population. In certain examples, the stabilisation, reduction, or elimination of the cancer stem cell population is achieved by administering a therapy that targets the growth and proliferation of the cancer stem cells.

Figure 4A:
FIG. 4 shows Western blot analysis of OTSCC cancer stem cells using antibodies specific for the RR, namely anti-ATP6IP2 primary antibody (ab40790) and Goat anti-rabbit HRP secondary antibody (A16110). The predicted 39 kDa renin receptor protein band was present in both OTSCC samples analysed. No staining was observed for cells associated with human liver tissue or secondary antibody alone (negative controls).
Figure 4B:
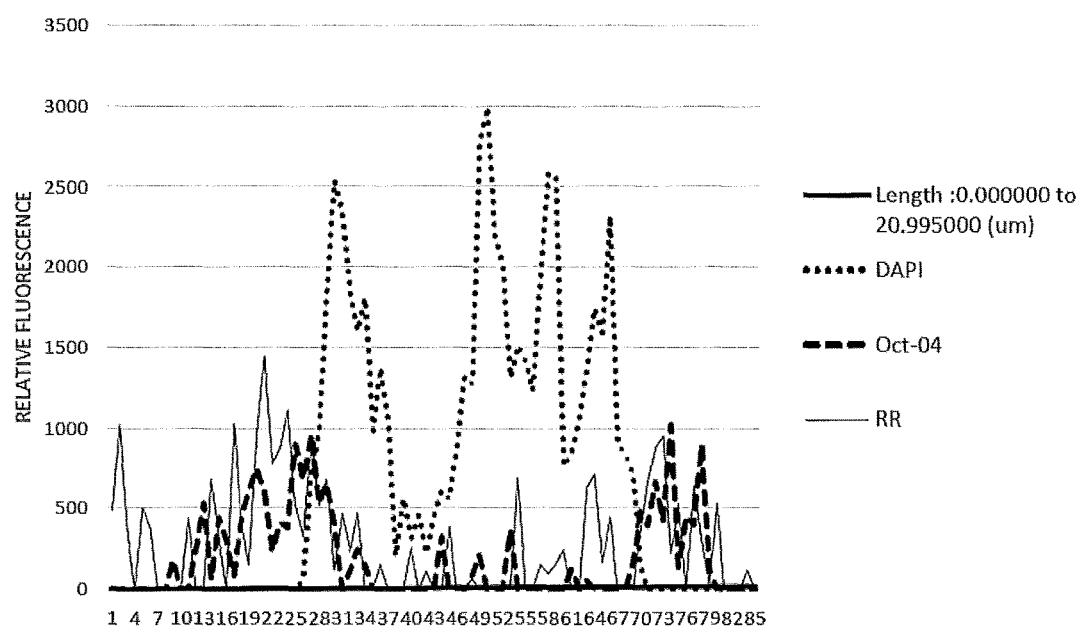
Figure 7A:
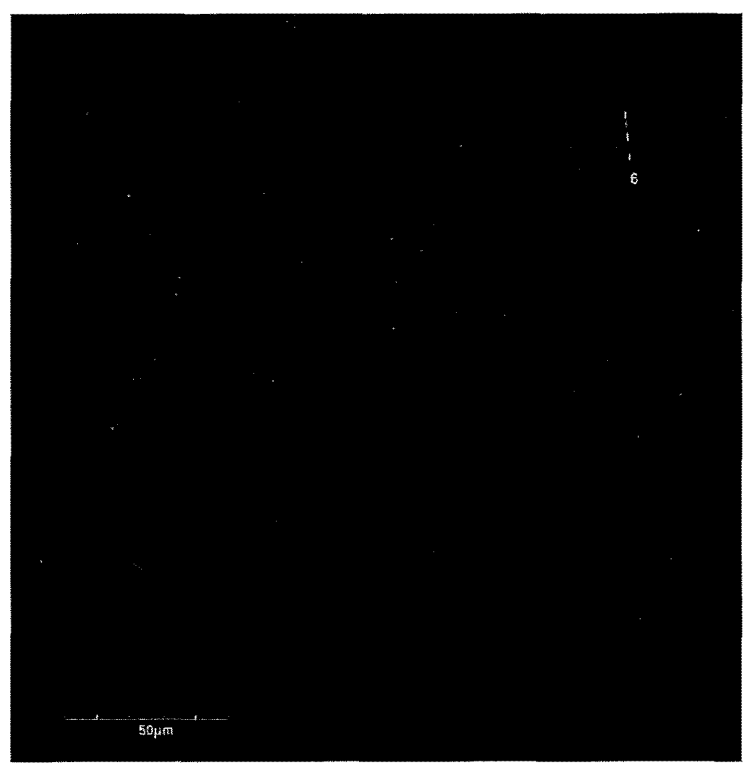
FIGS. 7A and 7B shows co-localisation of OCT4 and RR by the cancer stem cell population associated with melanoma.
Figure 7B:
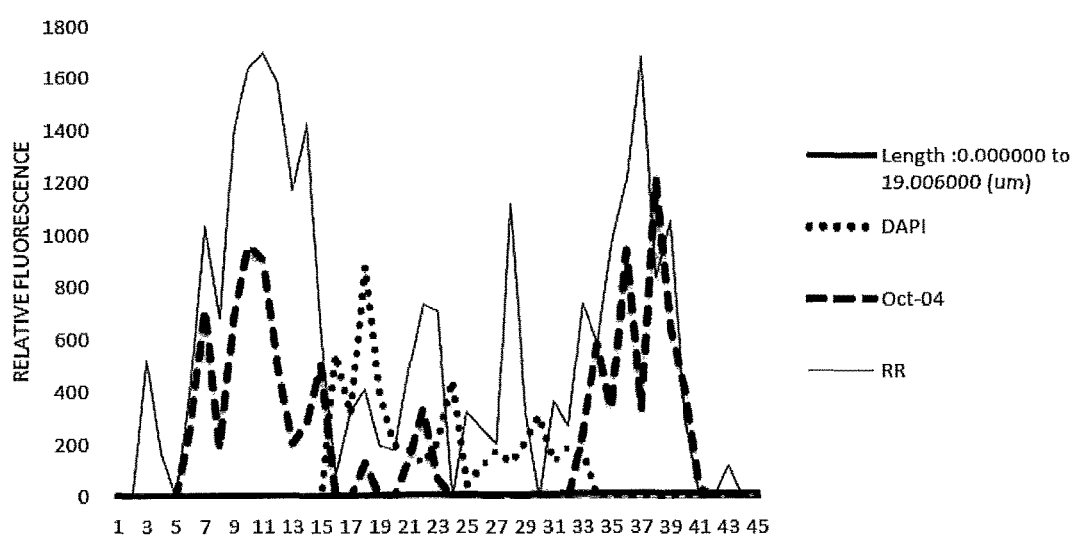
Figure 8:
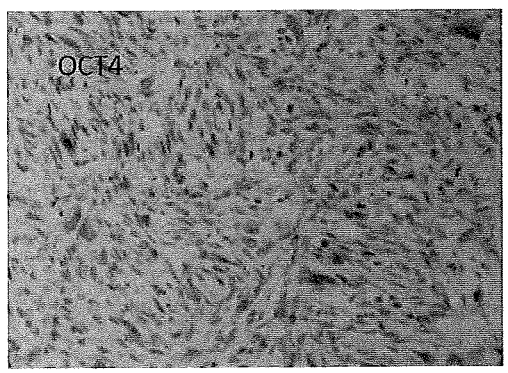
FIG. 8 shows the expression of OCT4, SOX2, ATIIR2 and RR by the cancer stem cell population associated with sarcoma (leiomyosarcoma) as evidenced by the immunohistochemical staining profiles.
Figure 8:
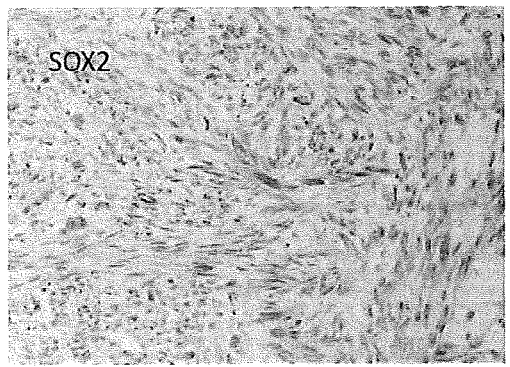
Figure 8:
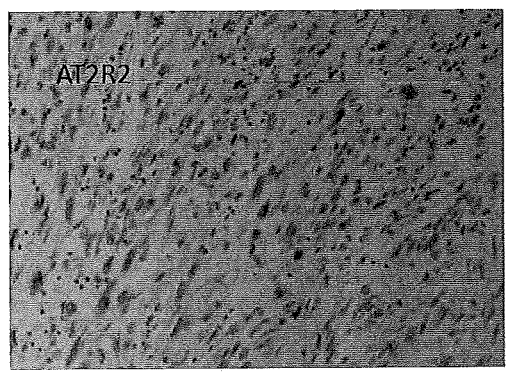
Figure 8:
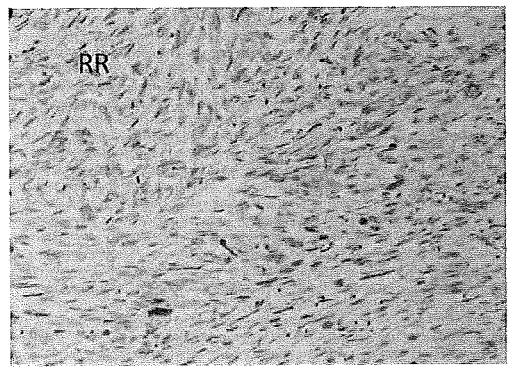
Figure 9A:
FIGS. 9A and 9B shows the co-localisation of OCT4 and RR by cancer stem cell population associated with sarcoma.
Figure 9B:
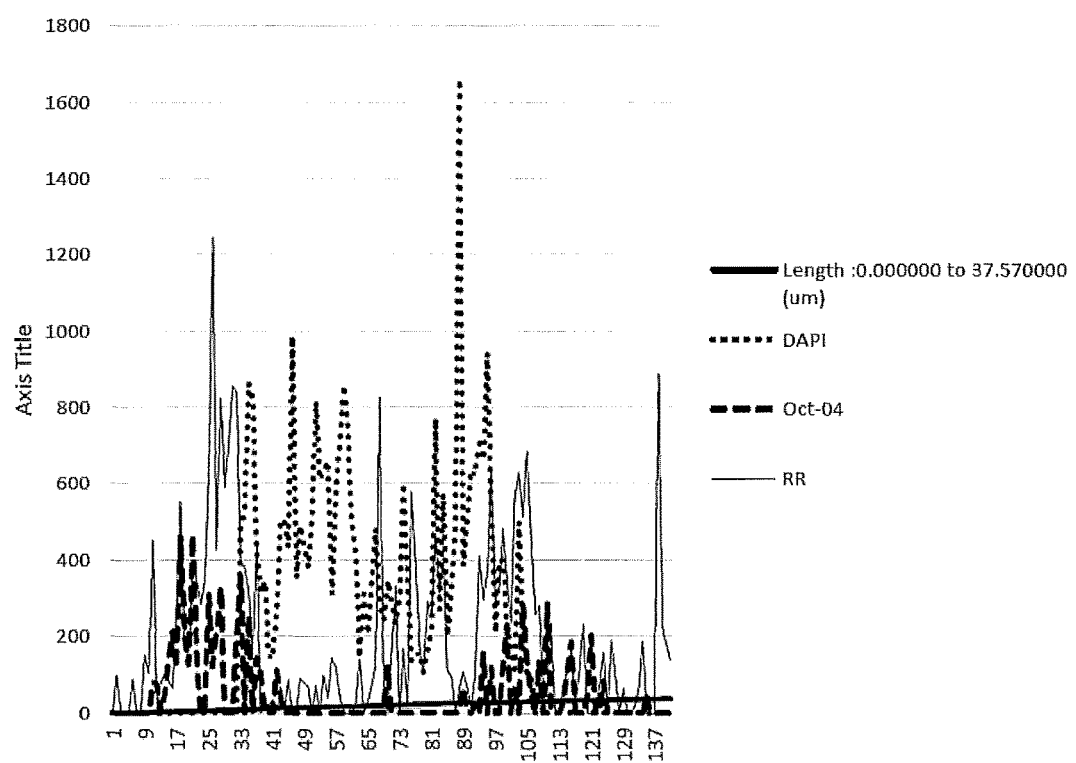
Figure 10:
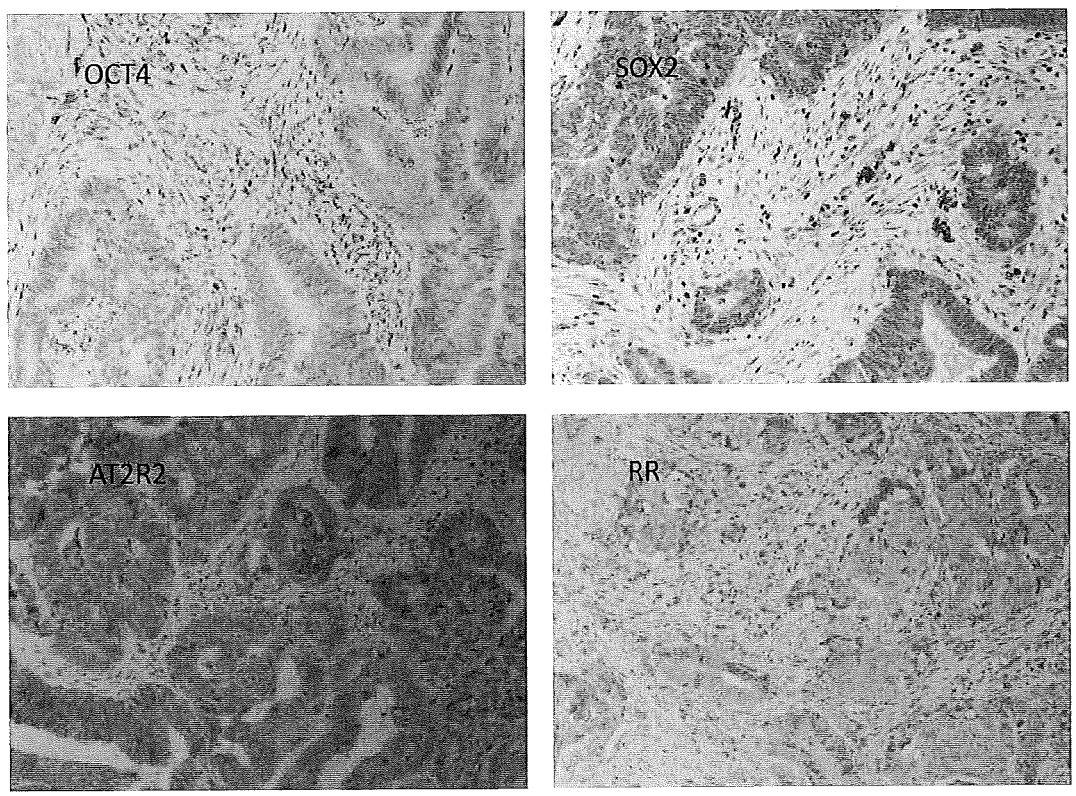
FIG. 10 shows expression of OCT4, SOX2, ATIIR2 and RR by the cancer stem cell population associated with bowel cancer as evidenced by the immunohistochemical staining profiles.
Figure 11A:
FIGS. 11A and 11B shows the co-localisation of OCT4 and RR in the cancer stem cell population associated with bowel cancer.
Figure 11B:
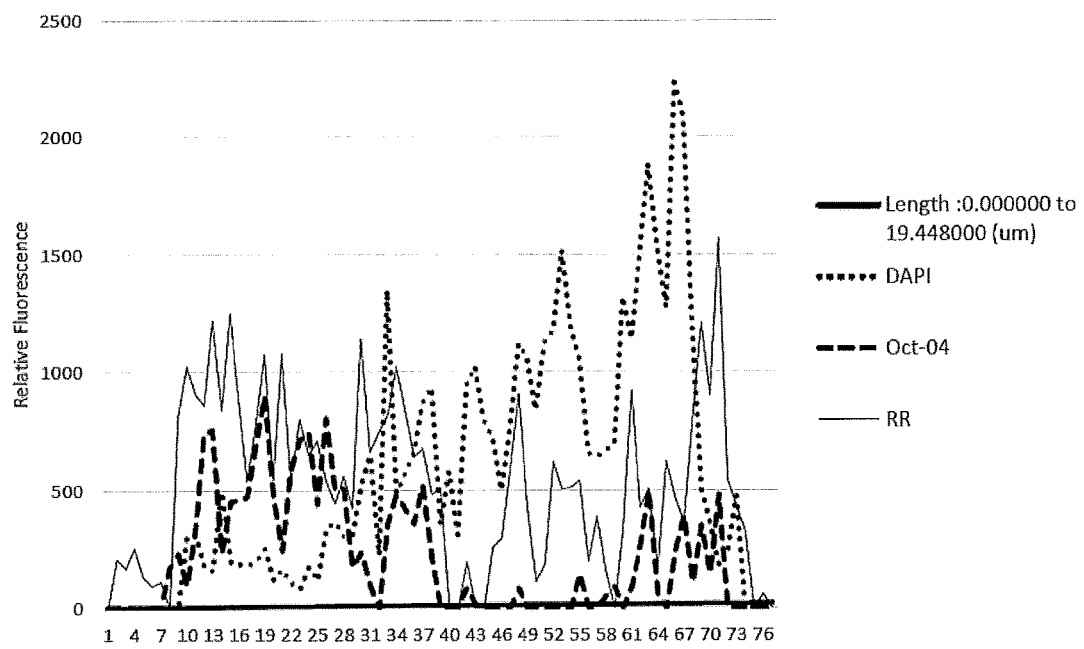
Figure 12:
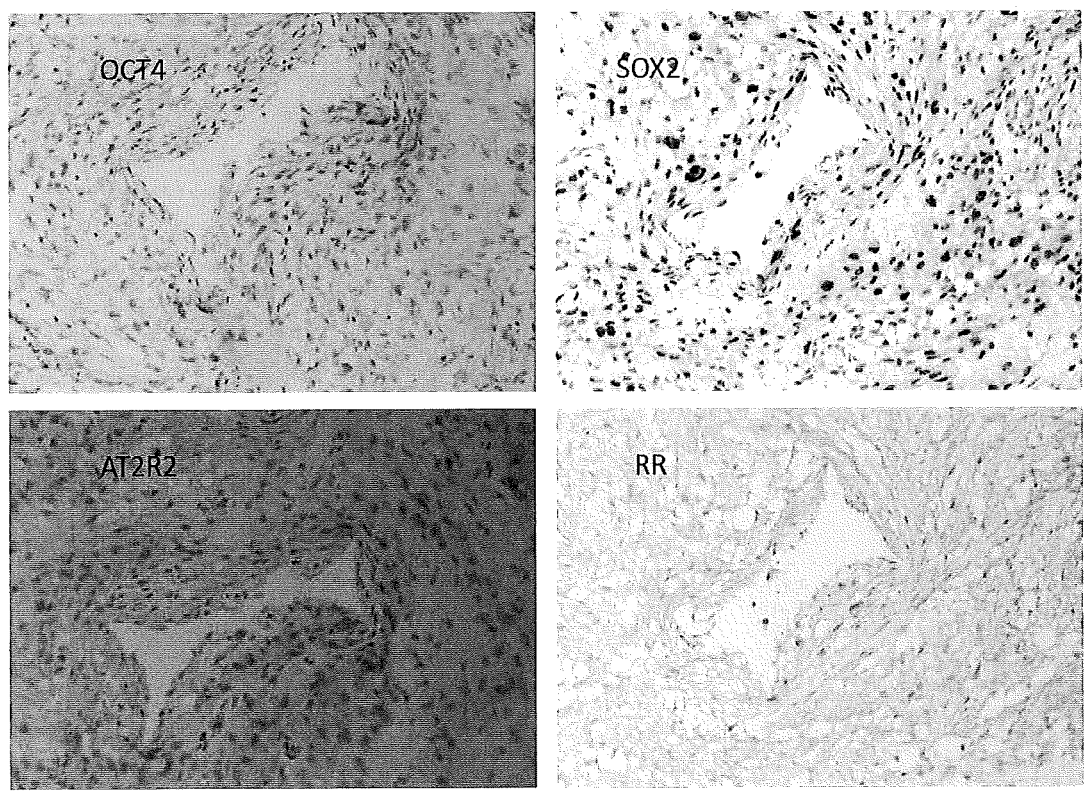
FIG. 12 shows the expression of OCT4, SOX2, ATIIR2 and RR by the cancer stem cell population associated with brain cancer (glioblastoma multiforme) as evidenced by the immunohistochemical staining profiles.
Figure 13A:
FIGS. 13A and 13B shows the co-localisation of OCT4 and RR in the cancer stem cell population associated with brain cancer (glioblastoma multiforme).
Figure 13B:
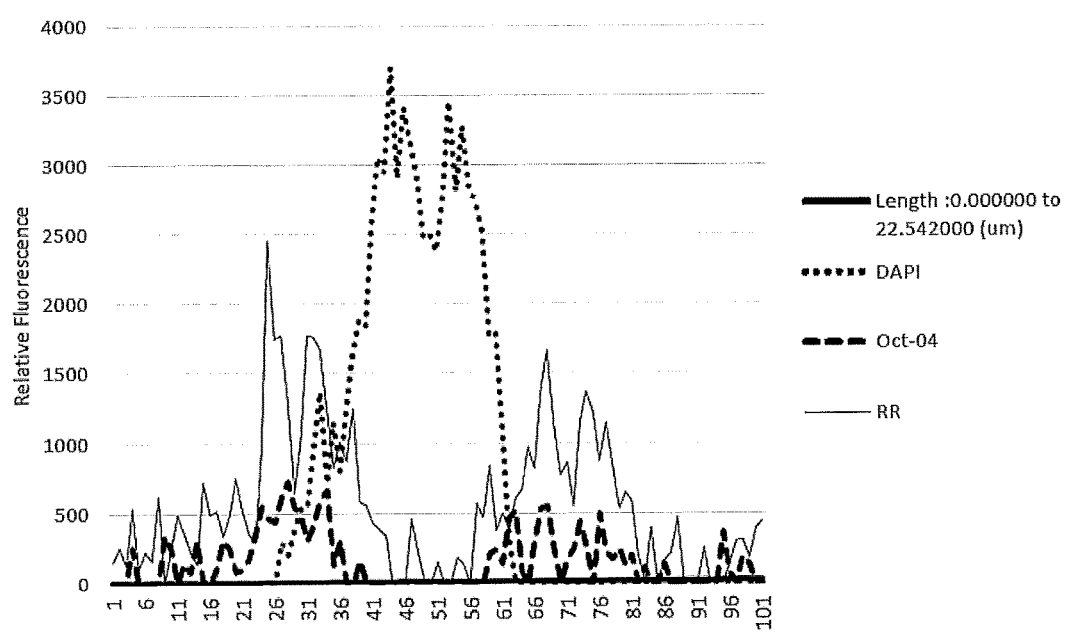
Figure 14:
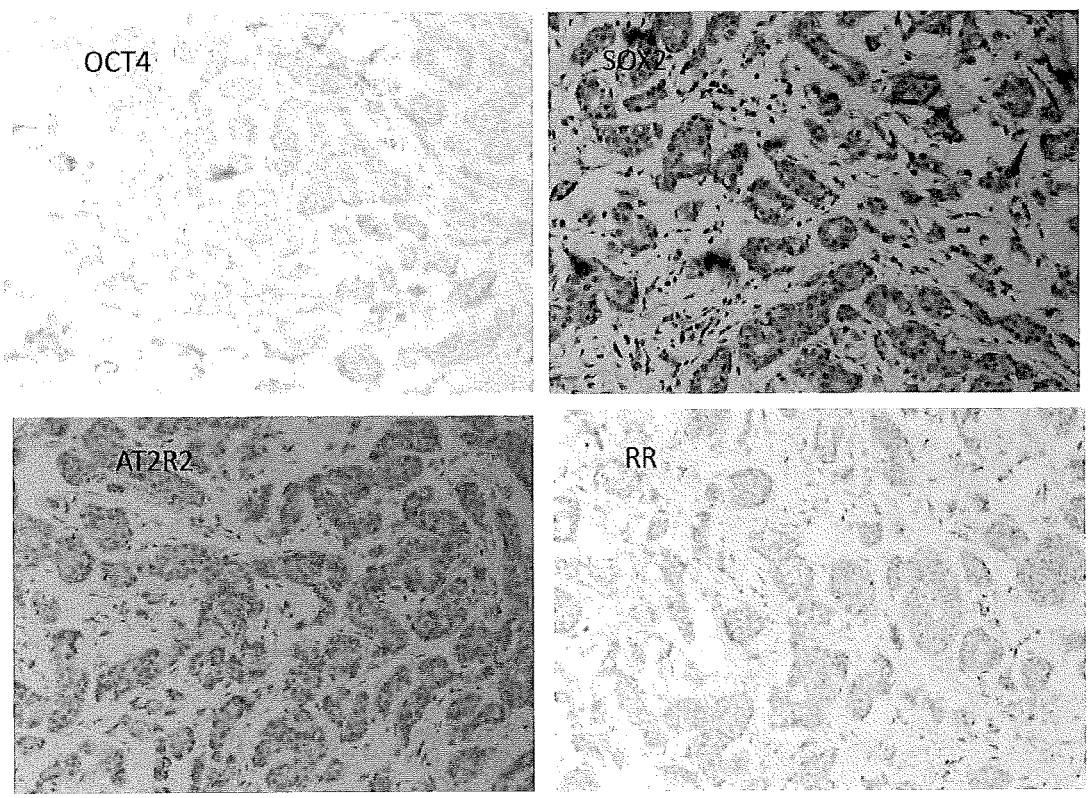
FIG. 14 shows the expression of OCT4, SOX2, ATIIR2 and RR in the cancer stem cell population associated with breast cancer as evidenced by the immunohistochemical staining profiles.
Figure 15A:
FIGS. 15A and 15B shows the co-localisation of OCT4 and RR in the cancer stem cell population associated with breast cancer.
Figure 15B:
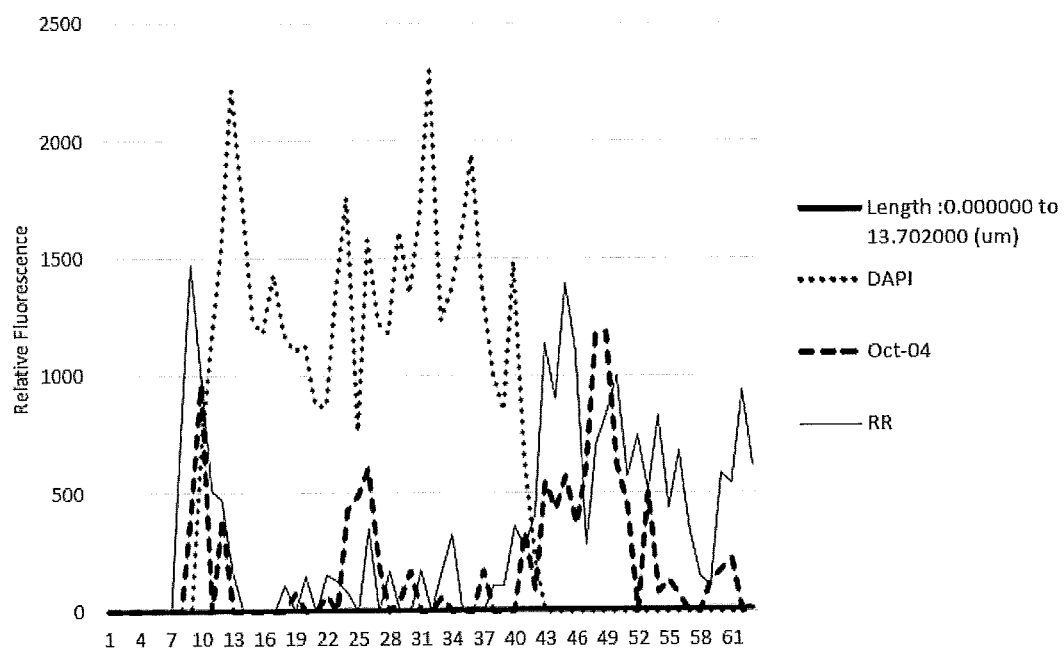
Figure 16:
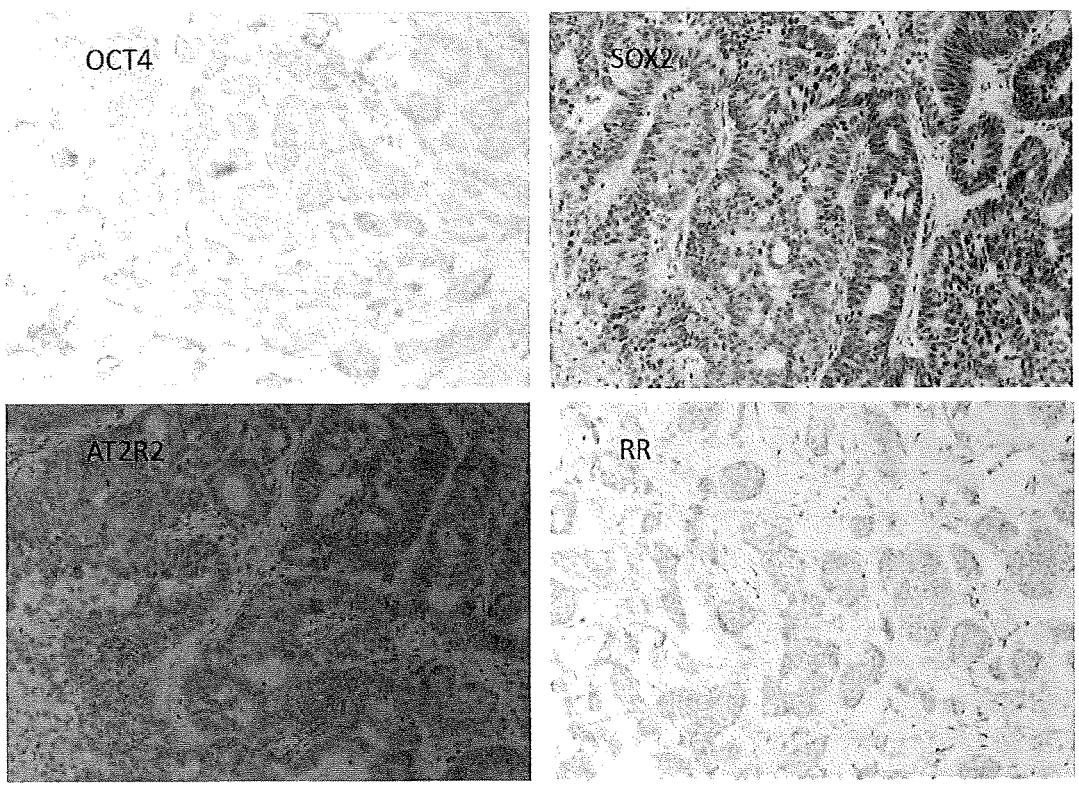
FIG. 16 shows the expression of OCT4, SOX2, ATIIR2 and RR by the cancer stem cell population associated with lung cancer (metastatic lung adenocarcinoma) as evidenced by the immunohistochemical staining profiles.
Figure 17A:
FIGS. 17A and 17B shows the co-localisation of OCT4 and RR in cancer stem cell population associated with lung cancer (metastatic lung adenocarcinoma).
Figure 17B:
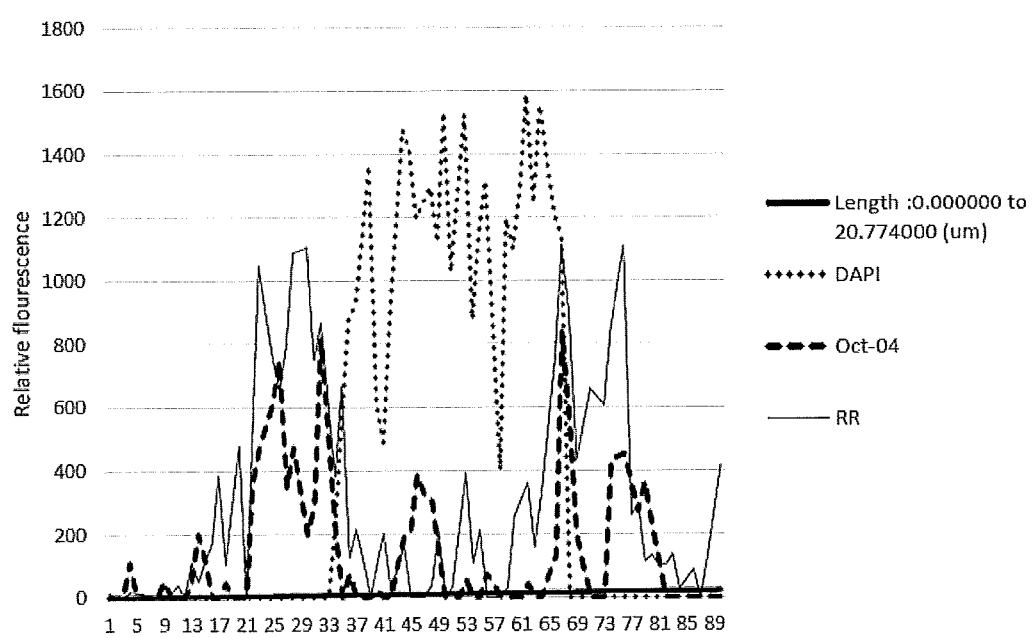
Figure 18:
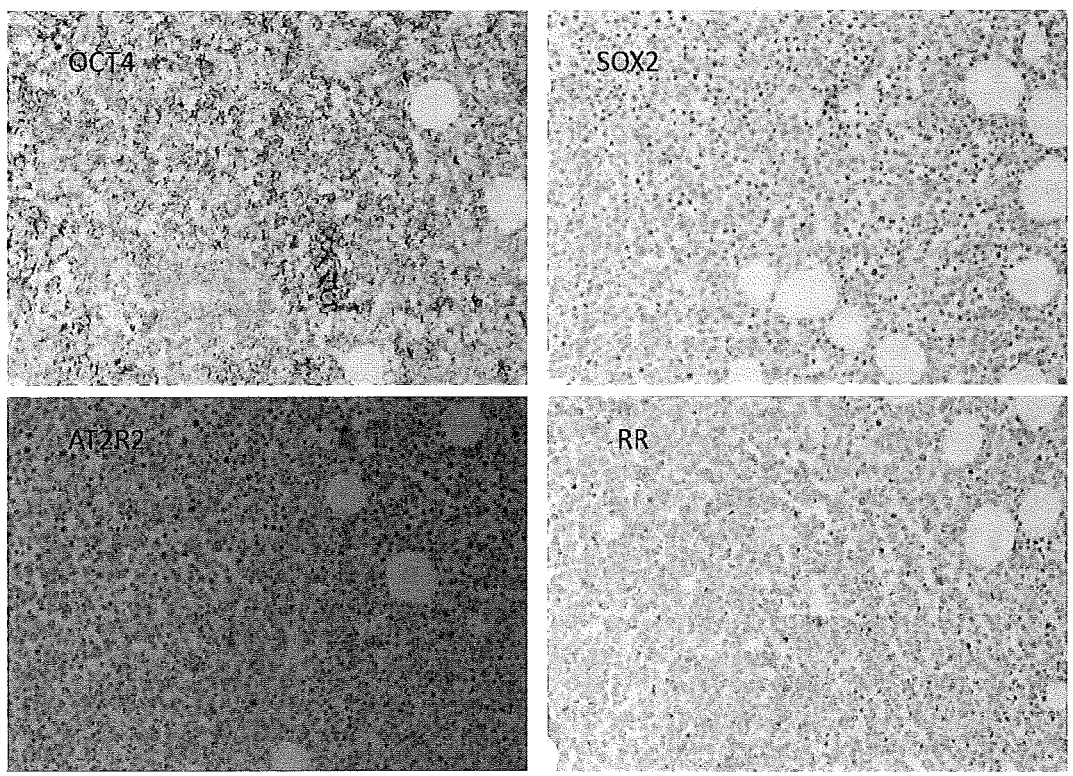
FIG. 18 shows the expression of OCT4, SOX2, ATIIR2 and RR by the cancer stem cell population associated with B cell lymphoma as evidenced by the immunohistochemical staining profiles.
Figure 19A:
FIGS. 19A and 19B shows the co-localisation of OCT4 and RR by the cancer stem cell population associated with B cell lymphoma.
Figure 19B:
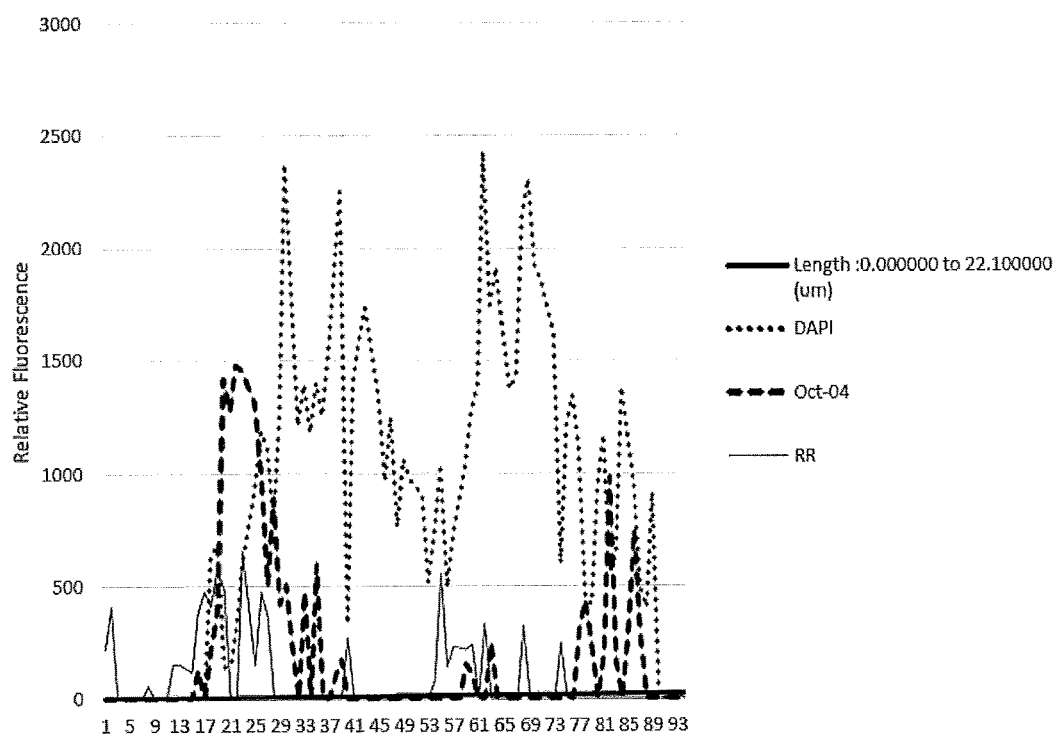
Figure 20:
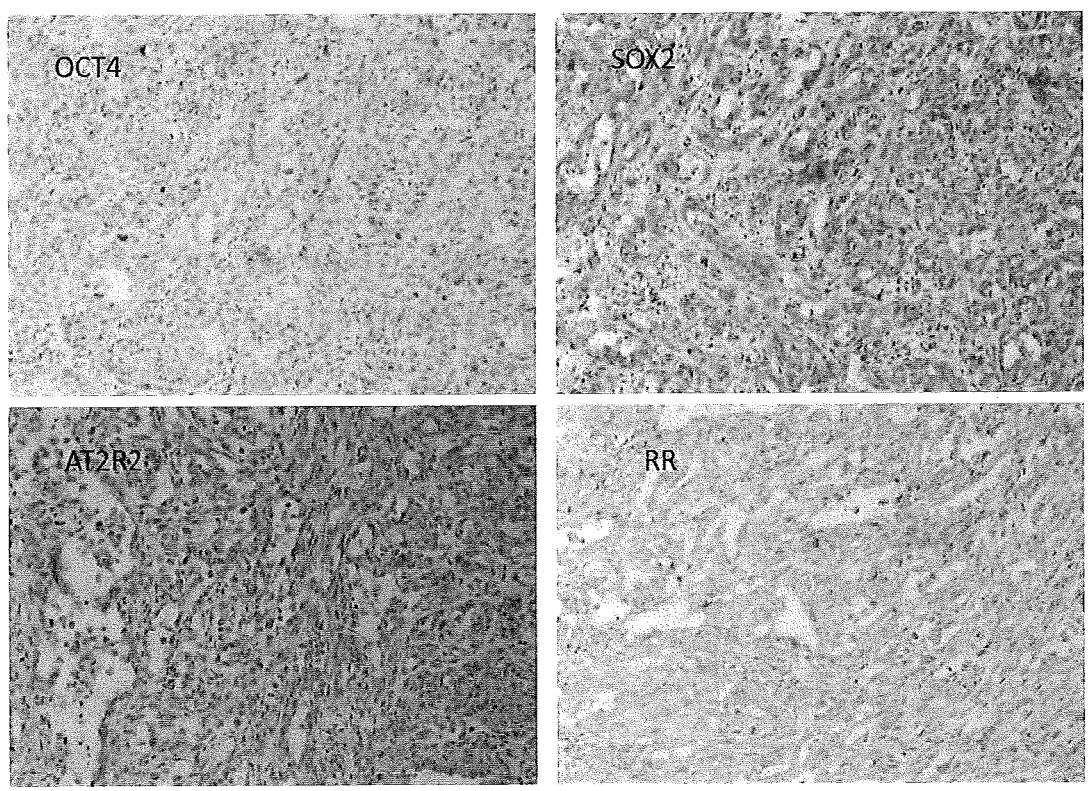
FIG. 20 shows the expression of OCT4, SOX2, ATIIR2 and RR by the cancer stem cell population associated with kidney cancer (metastatic renal cell cancer) as evidenced by the immunohistochemical staining profiles.
Figure 21A:
FIGS. 21A and 21B shows the co-localisation of OCT4 and RR by the cancer stem cell population associated with kidney cancer (metastatic renal cell cancer).
Figure 21B:
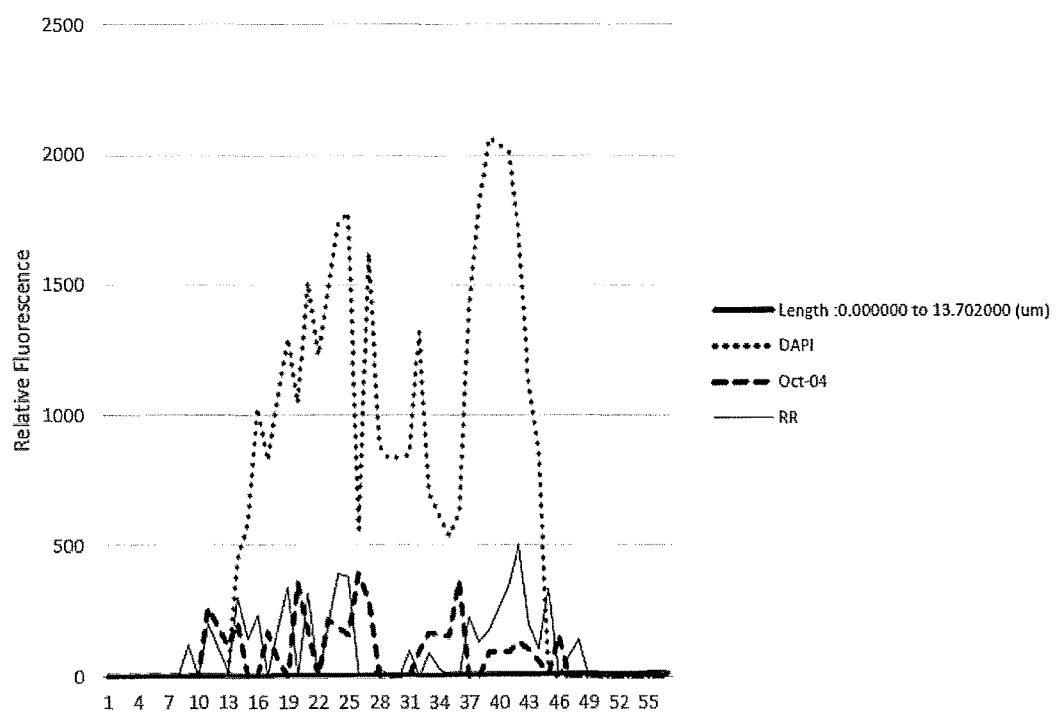
Figure 22:
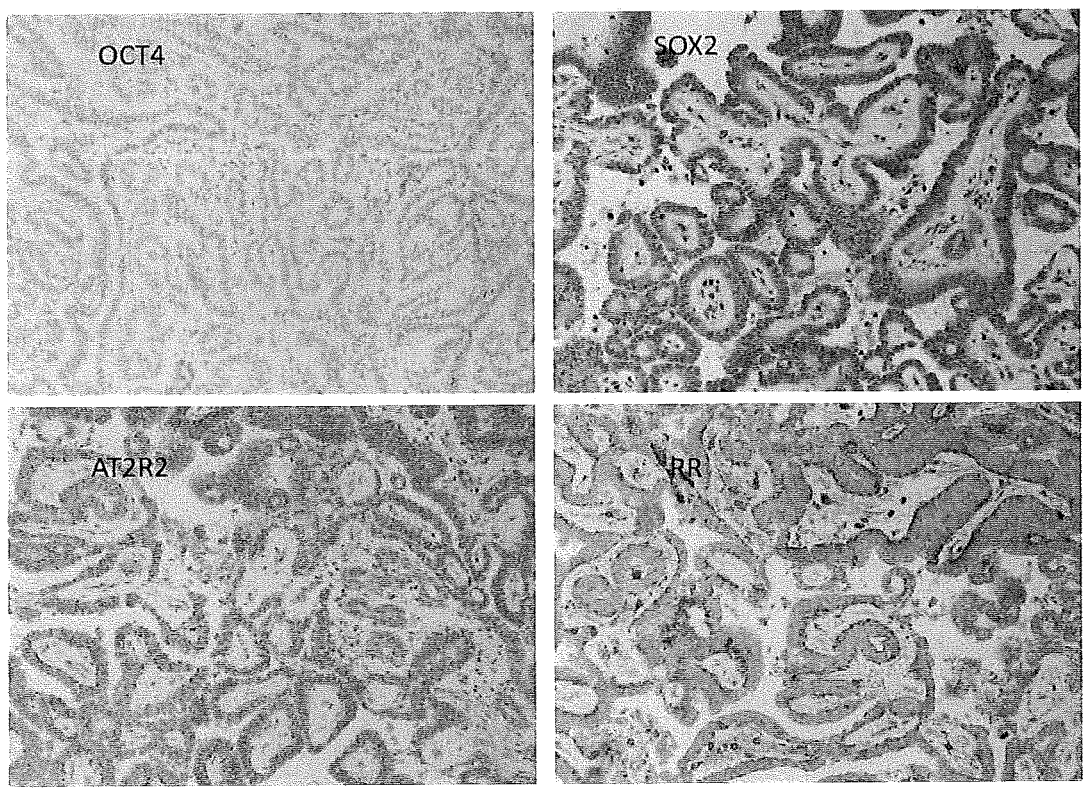
FIG. 22 shows the expression of OCT4, SOX2, ATIIR2 and RR by the cancer stem cell population associated with thyroid cancer as evidenced by the immunohistochemical staining profiles.
Figure 23B:
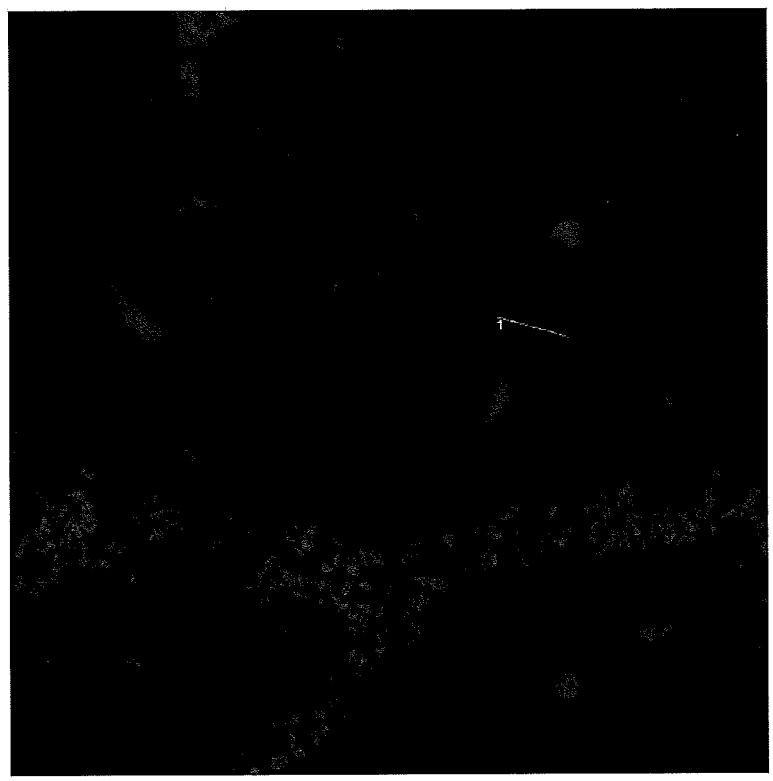
Figure 23B:
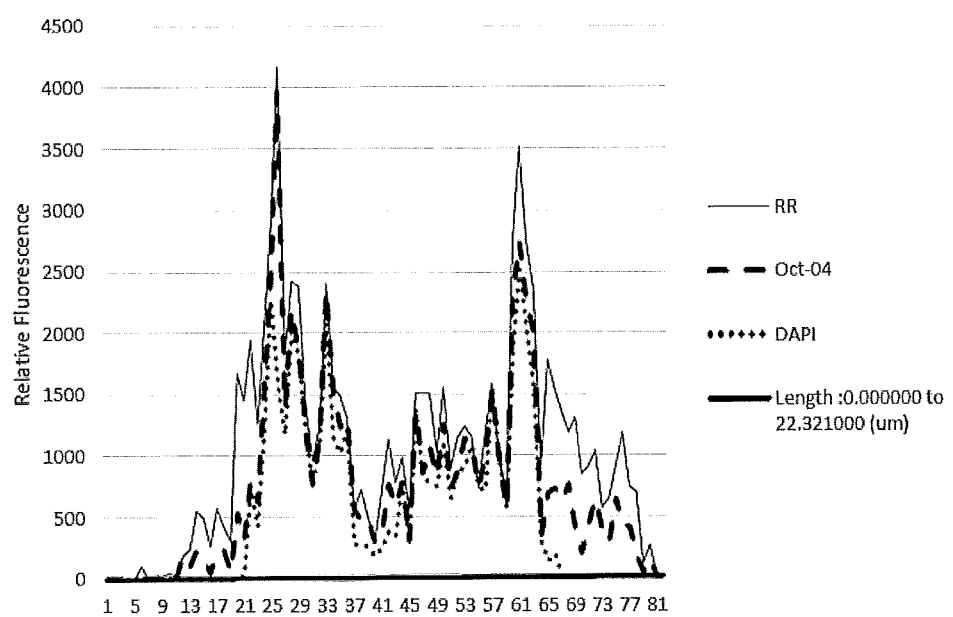
Figure 24:
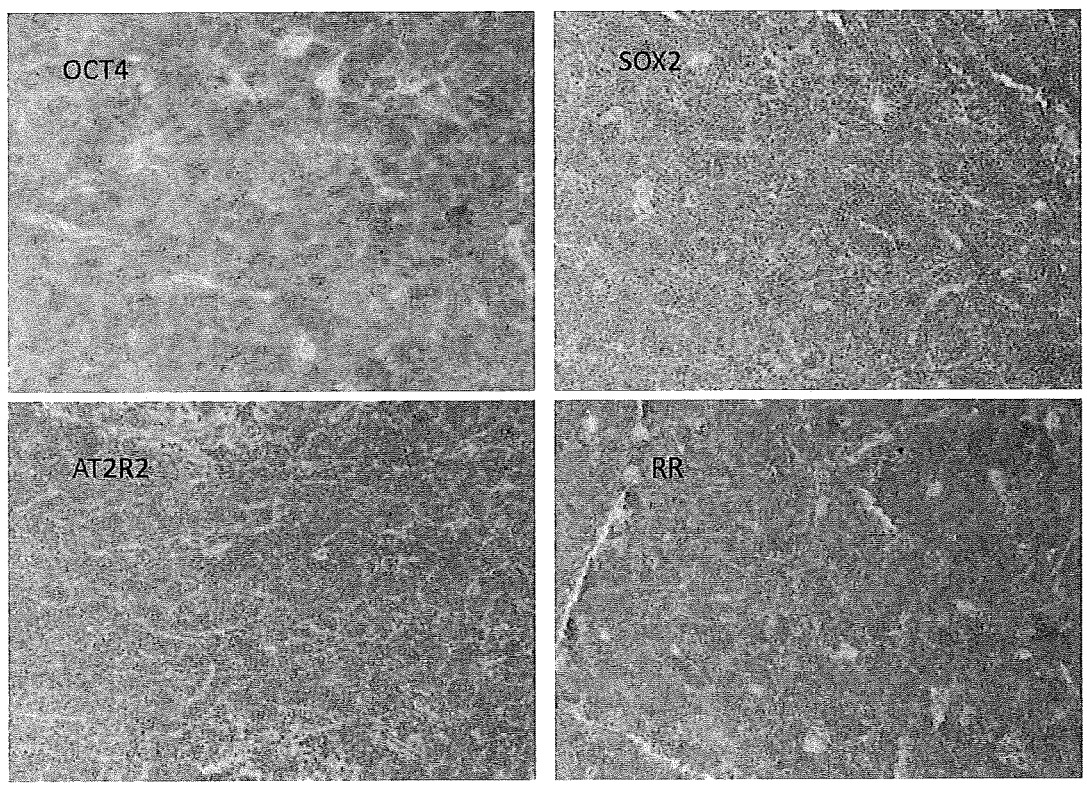
FIG. 24 shows the expression of OCT4, SOX2, ATIIR2 and RR by the cancer stem cell population associated with chronic lymphocytic leukaemia as evidenced by the immunohistochemical staining profiles.

Surprisingly, Applicants demonstrate that the cancer stem cell populations identified in the methods according to the present invention co-express components of RAS, and in cancer stem cell populations associated with multiple different tumour types. By way of illustration only, the Applicants demonstrate co-expression of the RR and ATIIR2 in OTSCC (FIGS. 4A, 4B), melanoma (FIGS. 7A, 7B), sarcoma (FIGS. 9A, 9B), bowel cancer (FIGS. 11A, 11B), brain cancer (FIGS. 13A, 13B), breast cancer (FIGS. 15A, 15B), lung cancer (FIGS. 17A, 17B), B cell lymphoma (FIGS. 19A, 19B), and kidney (FIGS. 21A, 21B), thyroid cancer (23A, 23B), chronic lymphocytic cancer (25A, 25B), skin squamous cell carcinoma (27A, 27B), prostate cancer (29A, 29B).

Figure 2:
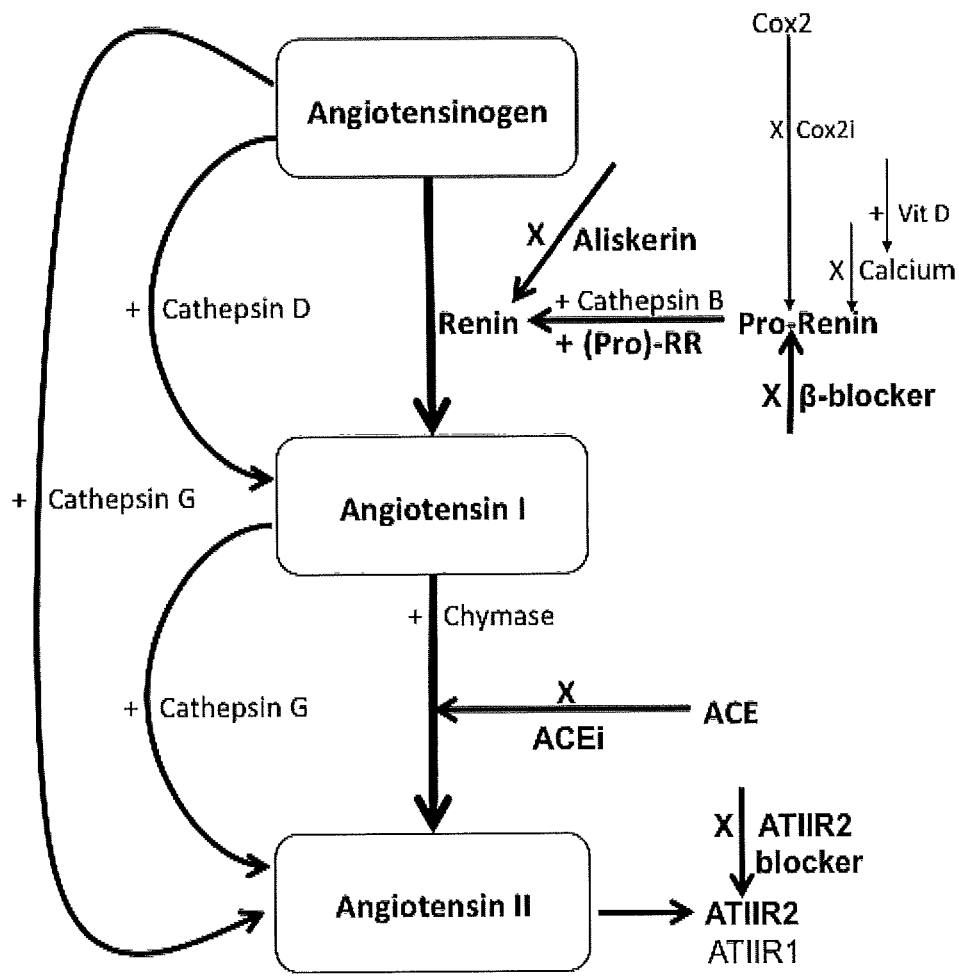
FIG. 2 shows the combined pathways associated with the RAS. ACE: Angiotensin Converting Enzyme; ACEI: Angiotensin Converting Enzyme Inhibitors; Cox2i: Cox2 inhibitors; β-blockers: Beta-Blockers; ATIIR2: Angiotensin II Receptor 2; ATIIR1: Angiotensin II Receptor 1; (Pro)-RR: Pro(Renin) Receptors [also called Renin Receptor (RR)]; Vit D: Vitamin D; XX: major blockades; x: minor blockades; ++: major promoting steps; +: minor blocking steps.
Figure 3:
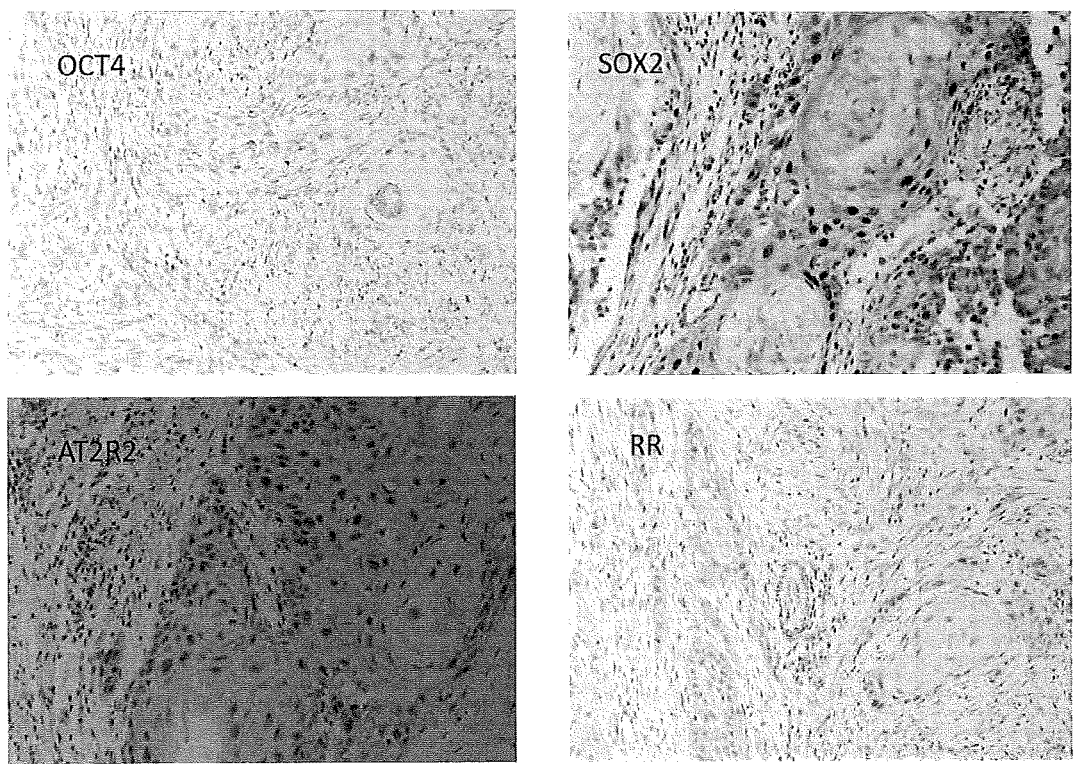
FIG. 3 shows the expression of OCT4, SOX2, ATIIR2 and RR by the cancer stem cell population associated with oral tongue squamous cell carcinoma (OTSCC) as evidenced by individual immunohistochemical staining profiles.

Accordingly, therapy that targets the growth and proliferation of cancer stem cell populations comprises administering a therapeutic agent that selectively targets components of the RAS and/or Pro/Renin Receptor Systems (PRRS) expressed by the cancer stem cells. FIGS. 1 and 2 show the types of inhibitors/drugs that target these systems, useful in accordance with the compositions and methods according to the present invention.

Examples of known therapeutics that target the Renin-Angiotensin System include, but are not limited to, ACEIs, ARBs, DRIs, Beta-Blockers, Cyclo-oxygenase 2 Inhibitors, Inhibitors of Cathepsin B, Cathepsin D and Cathepsin G, Calcium Channel Blockers, Calcium Supplements and Vitamin D.

Examples of ACEIs include, but are not limited to, Benazepril (Lotesin), Captopril (Capoten), Cilazipril, Enalapril (Vasotec, Renitec), Fosinopril (Monopril), Lisinopril (Lisodur, Lopril, Novatec, Prinivil, Zestril), Moexipril, Perindopril (Coversay, Aceon), Quinapril (Accupril), Ramipril (Altace, Tritace, Ramace, Ramiwin), Trandolapril, Delapril, Zofenopril and Imidapril.

Examples of ARBs include, but are not limited to, Losartan, Irbesartan, Candesartan, Eprosartan, Olmesartan, Telmisartan, PD123319 and Valsartan.

Examples of Beta-Blockers include, but are not limited to, Acebutolol (Sectral), Atenolol (Tenormin), Betaxolol (Betoptic), Bisoprolol (Cardicor, Emcor, Zebeta), Carteolol (Teoptic), Carvedilol (Coreg, Eucardic), Celiprolol (Celectol), Labetalol (Trandate), Levobunolol (Betagan), Metipranolol (Metipranolol Minims), Metoprolol (Betaloc, Lopresor, Lopressor, Toprol XL), Nadolol (Corgard), Nebivolol (Bystolic, Nebilet), Oxprenolol (Trasicor), Pindolol (Visken), Propranolol (Inderal LA), Sotalol (Beta-Cardone, Sotacor), and Timolol (Betim, Nyogel, Timoptol).

Examples of Cyclo-oxygenase 2 Inhibitors include, but are not limited to, Celecoxib, Nepafenac, Ibuprofen (Dolgesic), Indomethacin, Sulindac, Xanthohumol, Meclofenamate Sodium, Meloxicam, Rofecoxib, Bromfenac Sodium, Ibuprofen Lysine, Ketorolac (Ketorolac tromethamine), Diclofenac Sodium, Etodolac, Ketoprofen, Naproxen Sodium, Piroxicam, Acemetacin, Phenacetin, Tolfenamic Acid, Nimesulide, Flunixin Meglumin, Aspirin, Bufexamac, Niflumic acid, Licofelone, Oxaprozin, Lornoxicam, Lumiracoxib, Zaltoprofen, Ampiroxicam, Valdecoxib, Nabumetone, Mefenamic Acid, Carprofen, Amfenac Sodium monohydrate, Asaraldehyde and Suprofen.

Examples of Chymase Inhibitors include, but are not limited to, TY-51469 (2-[4-(5-fluoro-3-methylbenzo[b]thiophen-2-yl)sulfonamido-3-methanesulfonyl-phenyl]thiazole-4-carboxylic acid), Eglin C, CI, SUN13834, Chymostatin, TJK002 a benzimidazole inhibitor, ONO-WH-236, *Amblyomma americanum* tick serine protease inhibitor 6 (AamS6), N-tosyl-L-phenylalanyl chloromethyl ketone (TPCK), Alpha-aminoalkylphosphonate diaryl esters, Serine protease inhibitor A3 (serpinA3), Squamous cell carcinoma antigen (SCCA-2), Bortezomib (Velcade), RO5066852 and 17beta-estradiol.

Examples of Cathepsin B Inhibitors include, but are not limited to, Cystatin B, Cystatin C, Cysteine peptidase inhibitor E64, [Pt(dmba)(aza-N1)(dmso)] complex 1 (a potential anti-tumoral drug with lower IC50 than cisplatin in several tumoral cell lines), 2,3,7,8-Tetrachlorodibenzo-p-dioxin (TCDD), CA-074Me, Lipidated CtsB inhibitor incorporated into the envelope of a liposomal nanocarrier (LNC-NS-629), Proanthocyanidin (PA) and ahpatinin Ac (1) and ahpatinin Pr (2).

Examples of Cathepsin D Inhibitors include, but are not limited to, non-peptidic acylguanidine inhibitors of Cathepsin D, Pepstatin A, Bm-Aspin, SIPI, Via, RNAi-Rab27A and *Solanum lycopersicum* aspartic protease inhibitor (SLAPI).

Examples of Cathepsin G Inhibitors include, but are not limited to, WFDC12, Phenylmethylsulfonyl fluoride (PMSF), Ecotin, SerpinB1, SerpinA3, CeEI, or *Caesalpinia echinata* elastase inhibitor, SLPI (secretory leukocyte protease inhibitor), Alpha1-Antitrypsin (AAT), Bauhinia bauhinoides cruzipain inhibitor, Alpha-Aminoalkylphosphonate diaryl esters, Greglin, [2-[3-[[(1-benzoyl-4-piperidinyl) methylamino]carbonyl]-2-naphthalenyl]-1-(1-naphthalenyl)-2-oxoethyl]-phosphonic acid (KPA), Lympho-Epithelial Kazal-Type-related Inhibitor (LEKTI), Trappin-2 A62L, SV-66, SCGI, Bortezomib, Human monocyte/neutrophil elastase inhibitor (MNEI), a 42-kDa serpin protein and Anti-leukoproteinase (ALP).

Examples of Calcium Channel Blockers include, but are not limited to, Dihydropyridine Calcium Channel Blockers, Phenylalkylamine Calcium Channel Blockers, Benzothiazepine Calcium Channel Blockers, Non-Selective Calcium Channel Blockers, as well as "Other" Calcium Channel blockers.

Examples of Dihydropyridine Calcium Channel Blockers include, but are not limited to, Amlodipine (Norvasc), Aranidipine (Sapresta), Azelnidipine (Calblock), Barnidipine (HypoCa), Benidipine (Coniel), Cilnidipine (Atelec, Cinalong, Siscard) Not available in US, Clevidipine (Cleviprex), Isradipine (DynaCirc, Prescal), Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin), Pranidipine (Acalas).

Examples of Phenylalkylamine Calcium Channel Blockers include, but are not limited to, Verapamil (Calan, Isoptin), Gallopamil and Fendiline.

Examples of Benzothiazepine Calcium Channel Blockers include, but are not limited to, Diltiazem (Cardizem) and Fendiline.

Examples of Non-Selective Calcium Channel Blockers include, but are not limited to, Mibefradil, Bepridil, Flunarizine, Fluspirilene and Fendiline.

Examples of other Calcium Channel Blockers include, but are not limited to, Gabapentin, Pregabalin and Ziconotide.

An example of DRIs includes, but is not limited to, Aliskiren.

In certain examples, the cancer stem cells may be partially differentiated and committed toward a specific cell lineage associated with a particular tumour.

In one example, the partially differentiated cancer stem cells are characterised by expression of one or more tumourigenic biomarkers, or co-express with one of more tumourigenic biomarkers, selected from the group consisting of epithelial cancer cell markers, lymphatic cell markers, blood vascular markers, myeloid cell markers, as well as combinations thereof.

Examples of epithelial cancer cell markers include, but are not limited to, p63, epithelial membrane antigen (EMA) and cytokeratins including CYK 5, CYK6, CYK 8 and CYK18.

Examples of cancer stem cell markers include, but are not limited to, CD44, CD133, CD24, and ALDH1.

Examples of lymphatic cell markers include, but are not limited to, LYVE-1 and VEGFR-3.

Examples of blood vascular markers include, but are not limited to, CD34 and ACE.

Examples of haemogenic endothelial markers include, but are not limited to, TAL-1.

Examples of myeloid markers include, but are not limited to, tryptase and CD163.

Examples of epithelial to mesenchymal transition (EMT) markers include, but are not limited to, Twist, Slug, SNAIL, Bmi1 and MMP-9.

Examples of proliferation markers include, but are not limited to, Ki67.

For example, any given tumour may possess different populations of cells, including cancer stem cells, partially differentiated cancer stem cells and mature tumour cells etc.

By way of illustration only, the partially differentiated stem cells associated with a squamous cell carcinoma may express certain markers such as EMA and p63. Similarly, partially differentiated cancer stem cells associated with leukemia may express markers such as TAL-1 and GATA-2.

As such, the present invention also contemplates not only identification of cancer stem cells (expressing e.g., embryonic stem cells markers), but also to the identification of partially differentiated cancer stem cells that are committed to a certain cell lineage associated with a particular tumour/cancer or mature tumour cells. Accordingly, the present invention may be used to provide an initial prognosis or diagnosis as to the existence of progenitor cancer stem cells (and therefore likelihood of possessing, or being predisposed to, cancer), which may be followed up with subsequent interrogations to determine the type of cancer by investigating e.g., the profile of partially differentiated cancer stem cells or mature tumour cells. The latter investigations may be conducted using biomarker expression profiles on cells obtained from a biological sample obtained from, or known to be associated with, a tumour e.g., tissue biopsy or a blood/serum sample through tumour shedding. The specific cell marker signatures associated with partially differentiated cancer stem cells and/or mature tumour cells for any given tumour type would be well known to a person skilled in the art.

Gene expression profiles and signatures associated with cancer stem cells, for example solid tumour stem cells, as well as novel stem cell cancer markers are useful for the diagnosis, characterization, prognosis and treatment of tumours involving cancer stem cells. Biomarker expression analysis can be used to determine the population (or subpopulations) of cancer stem cells responsible for tumourigenesis. These sub/populations of cancer stem cells can then be targeted using effective treatment regimes in order to prevent the growth and spread of a tumour, as well as its potential metastasis.

As such, the present invention is also useful in the prognosis and diagnosis of cancer, in particular by profiling a biological fluid sample for the presence of a cancer stem cell or cancer stem cell population.

Accordingly, in another aspect of the present invention there is provided a method for determining presence or absence of cancer in a subject, the method comprising:

(i) detecting and/or measuring the level of a cancer stem cell population in a biological sample obtained from the subject using biomarker expression analysis;

(ii) comparing the level of the cancer stem cell population obtained from the sample against the cancer stem cell level from a control population, wherein, an increased level in the cancer stem cell population obtained from the biological sample relative to the control population is diagnostic that the subject has, or is predisposed to developing, cancer. In another aspect of the present invention there is provided a method for determining presence or absence of cancer in a subject, the method comprising:

(i) detecting and/or measuring the level of a cancer stem cell population in a biological sample obtained from the subject using biomarker expression analysis;

(ii) comparing the level of the cancer stem cell population obtained from the sample against the cancer stem cell level from a control population, wherein, an increased level in the cancer stem cell population obtained from the biological sample relative to the control population is diagnostic that the subject has, or is predisposed to developing, cancer, and (iii) administering a prophylactic or therapeutic regime to the subject who has, or is predisposed to developing, cancer.

In certain examples according to the prognostic and diagnostic methods of the present invention, the cancer stem cells are characterised by expression of one or more embryonic stem cell biomarkers as well as expression of one or more biomarkers associated with the Renin-Angiotensin System. In one example, the one or more embryonic stem cell markers is selected from the group consisting of OCT4, SOX2, NANOG, CD44, SAL-4, SSEA4, PSTAT3, and H1F1. In another example, the one or more embryonic stem cell biomarkers consists in OCT4, SOX2, NANOG and PSTAT3. In yet another example, the one or more biomarkers associated with the Renin-Angiotensin System is selected from the group consisting of RR, ATIIR2 and sRR.

In other examples according to the prognostic and diagnostic methods of the present invention, the therapeutic agent is selected from the group consisting of ACEIs, ARBs, Direct DRIs, Beta-Blockers, Cyclo-oxygenase 2 Inhibitors, Chymase Inhibitors, Inhibitors of Cathepsin B, Cathepsin D and Cathepsin G, Calcium Channel Blockers, Calcium Supplements and Vitamin D.

In another aspect of the present invention there is provided a method for determining presence or absence of cancer in a subject, the method comprising:

(i) detecting and/or measuring the level of a partially differentiated cancer stem cell population in a biological sample obtained from the subject using biomarker expression analysis;

(ii) comparing the level of the partially differentiated cancer stem cell population obtained from the sample against the partially differentiated cancer stem cell level from a control population, wherein, an increased level in the partially differentiated cancer stem cell population obtained from the biological sample relative to the control population is diagnostic that the subject has, or is predisposed to developing, cancer.

In another aspect of the present invention there is provided a method for determining presence or absence of cancer in a subject, the method comprising:

(i) detecting and/or measuring the level of a partially differentiated cancer stem cell population in a biological sample obtained from the subject using biomarker expression analysis;

(ii) comparing the level of the partially differentiated cancer stem cell population obtained from the sample against the partially differentiated cancer stem cell level from a control population, wherein, an increased level in the partially differentiated cancer stem cell population obtained from the biological sample relative to the control population is diagnostic that the subject has, or is predisposed to developing, cancer, and (iii) administering a prophylactic or therapeutic regime to the subject who has, or is predisposed to developing, cancer.

In an example according to the prognostic and diagnostic methods of the present invention, the biomarker analysis is performed using gene expression and/or protein analysis techniques.

The therapeutic agent(s) comprises any known or as yet unidentified therapeutic which selectively targets the cancer stem cell population. Examples of known therapeutics are listed herein. In an example, the therapeutic agent results in an approximately 25% reduction, an approximately 40% reduction, an approximately 50% reduction or an approximately 75% reduction in cancer cells. This includes both cancer stem cells and mature/bulk tumour cells.

In a related example, reduction in cancer cells is determined by comparing the amount of cells with a cancer cell marker phenotype present in a tissue sample from the human subject to the amount of cells with the same cancer cell marker phenotype present in a tissue sample from the same human subject at an earlier time point.

The growth, proliferation and/or differentiation of cancer stem cells may be selectively eradicated or inhibited using a therapeutic agent. Accordingly, in one example, growth, proliferation and/or differentiation of the cancer stem cells is selectively inhibited using a therapeutic agent that binds to a cell surface antigen and arrests the growth and proliferation of the cancer stem cells.

In another example, growth, proliferation and/or differentiation of the cancer stem cells is selectively inhibited using a therapeutic agent that comprises a differentiation factor capable of differentiating a cancer stem cell to a non-malignant cell lineage or away from a malignant cell lineage potential. The differentiated cells no longer retain the ability to be tumourigenic.

By effectively arresting the growth, proliferation and/or differentiation of the cancer stem cells, their ability to differentiate into tumour/bulk cells is also inhibited, resulting in reduced spread and growth of the tumour.

The inventors of the present application have also surprisingly identified that the cancer stem cells co-express with lymphatic cell lineages (e.g. lymphatic cells which express, for example LYVE-1 and/or VEGFR-3). Accordingly, this would suggest that the spread and metastasis of cancer may be via the lymphatic system rather than the more accepted blood vasculature (i.e., angiogenesis) and provides alternative targets as a means for preventing the spread of cancer to secondary sites (i.e., metastasis).

In certain examples, the therapeutic agent results in the stabilisation of a cancer stem cell population after a period of time (e.g., after 2, 5, 10, 20, 30 or more doses of a therapy, or after 2 weeks, 1 month, 2 months, 1 year, 2 years, 3 years, 4 years or more). In other examples, the therapeutic agent achieves a 5%-40%, 10%-60%, 20% to 99% or higher reduction in the cancer stem cell population. In other examples, a reduction in a cancer stem cell population is achieved after 2 weeks, 1 month, 2 months, 3 months, 4 months, 6 month, 9 months, 1 year, 2 years, 3 years, or 4 years of administration of one or more therapies. In further examples, in accordance with the therapy, the reduction in a cancer stem cell population is monitored periodically (e.g., after 2, 5, 10, 20, 30 or more doses of one or more therapies, or after 2 weeks, 1 month, 2 months, 1 year, 2 years, 3 years, 4 years or more after receiving one or more therapies). The stabilization, reduction or elimination of a cancer stem cell population stabilises, reduces or eliminates the cancer cell population produced by the cancer stem cell population, and thus, stabilises, reduces or eliminates the growth of a tumour, the bulk size of a tumour, the formation of a tumour and/or the formation of metastases. In other words, the stabilization, reduction or elimination of the cancer stem cell population prevents the formation, reformation or growth of a tumour and/or metastases by cancer cells.

Therapeutic agent or agents according to the present invention can inhibit cancer stem cell growth in vitro and in vivo. Examples of different therapeutic agents are listed in further detail below.

Conventional cancer therapies, including chemotherapy, target mature tumour cells in an attempt to control or treat the cancer. For example, conventional chemotherapy agents seek to interrupt normal cell-cycle. As a consequence, standard chemotherapy only effectively targets those cells that are rapid-cycling. Whereas mature tumour cells are rapid-cycling, cancer stem cells are slow-cycling. As such, conventional chemotherapy involves the targeting and killing of mature tumour cells, as well as other non-tumour rapid-cycling cells present, but having an enriching effect on cancer stem cells, as they are not targeted and so continue to proliferate.

This then gives the cancer stem cells an opportunity to either repopulate the tumour bulk cells, resulting in tumour recurrence, or metastasise and form a secondary tumour elsewhere in the body.

Cancer stem cell biology is still poorly understood, with many studies focusing on identifying single markers that can be used as independent prognostic indicators and identifiers of these cells.

The present inventors have investigated the overall protein expression profile of cancer stem cells and ultimately the molecular systems that control tumourigenesis. For example, it is likely that the RAS may play a role in this (supported by the expression of ACE by these cells; refer to Example 2/Table 5), although other important molecular triggers and signalling pathways are also likely to be involved.

By understanding the molecular triggers and signalling pathways involved in tumourigenesis, with an emphasis on the role of cancer stem cell populations, the inventors have identified novel treatment targets that will allow selective targeting of the cancer stem cells, thereby eliminating the driving force behind cancer. In addition, by inducing differentiation of these cells to a mature cell type such as adipose tissue, this would eradicate the malignant potential of these cells.

In addition to the methods described herein, the present invention also provides pharmaceutical compositions useful in the treatment or prevention of cancer. The pharmaceutical compositions of the present invention comprise therapeutic agents sufficient to selectively eradicate, or inhibit the growth, proliferation and/or differentiation of cancer stem cells in a tumour associated with a cancer.

Accordingly in another aspect of the present invention there is provided a pharmaceutical composition for use in a method for treatment of cancer, wherein the pharmaceutical composition comprises a therapeutic agent(s) sufficient to selectively inhibit eradicate, or the growth, proliferation and/or differentiation of cancer stem cells in a tumour associated with a cancer, and wherein the method comprises administering the therapeutic agent to a patient with cancer.

In yet another aspect of the present invention there is provided a kit or article of manufacture for use in the treatment of cancer, the kit comprising a therapeutic agent(s) sufficient to selectively eradicate, or inhibit the growth, proliferation and/or differentiation of cancer stem cells in a tumour associated with a cancer, together with instructions for how to administer a therapeutic dose to the subject.

Since the cancer stem cells according to the present invention have been shown to express key regulatory components of the (e.g.) Renin-Angiotensin System and/or the Pro/Renin System, the cancer stem cell populations associated with certain tumours may be effectively targeted by administering a therapeutic amount of a drug which is known to also target these systems. Examples include, but are not limited to, Angiotensin-Converting Enzyme Inhibitors (ACEIs), Angiotensin Receptor Blockers (ARBs), Direct Renin Inhibitors (DRIs), Beta-Blockers, Cyclo-oxygenase 2 Inhibitors, Chymase Inhibitors, Cathepsin Inhibitors including Cathepsin B Inhibitors, Cathepsin D Inhibitors and Cathepsin G Inhibitors, Calcium Channel Blockers, Calcium Supplements and Vitamin D, as described above.

In certain examples the method for treatment of cancer comprises determining in vitro that the therapeutic agent can decrease the amount of cancer stem cells in a sample comprising cancer stem cells, prior to administration of the therapeutic agent.

Further detail with respect to the present invention is presented under the following sub-headings.

Renin-Angiotensin System

The renin-angiotensin system (RAS) is traditionally known to preserve fluid volume during periods of restricted dietary salt and also prevents ischaemia during acute volume loss. The main effector peptide of the RAS is angiotensin II (ATII). It induces vasoconstriction and sympathetic activation, raises aldosterone levels, and promotes renal salt and water retention via the angiotensin II receptor 1 (ATIIR1). Over the last few decades, the RAS has been a drug target of particular interest because of its involvement in cardiovascular disease (CVD) and renovascular disease. The CVD and renovascular disease can be understood as a continuum of risk factors, target organ damage, events, and mortality. Risk factors (such as hypertension, dyslipidemia, diabetes, and smoking) led to the development of target organ damage including atherosclerosis, left ventricular hypertrophy (LVH), and renal impairment. Target organ damage progressively worsens, leading ultimately to myocardial infarction (MI), heart failure (HF), end-stage renal disease (ESRD), stroke, or death.

ATII the main effector peptide of the RAS, plays an active role during all stages of this continuum. The first step in the RAS cascade is the formation of angiotensin I (ATI) from the precursor angiotensinogen under the action of renin; early evidence for the importance of RAS in CVD came from the consistent finding that renin activity is predictive of the risk of cardiovascular (CV) events. ATI is then converted to ATII, the principal effector peptide of the RAS, by angiotensin-converting enzyme (ACE). In addition, ATII can be produced in tissues by enzymes such as chymase. This locally produced ATII is believed to mediate paracrine and autocrine functions. ATII acts via ATIIR1 and ATIIR2. Activation of ATIIR1 results in vasoconstriction, aldosterone and vasopressin secretion, sodium retention, and decreased renal perfusion. Hence, these receptors mediate the deleterious effects of ATII, including elevated blood pressure (BP) and cardiac and vascular remodelling. The effects of the ATII receptors have been less clearly defined because of the limited expression of these receptors in adults, because of their unconventional signaling pathways, and because many ATII-mediated actions are masked by opposing ATI-mediated effects. However, it is now recognised that ATIIR2 generally oppose the actions of ATIIR1, mediating various antiproliferative and anti-inflammatory effects and promoting tissue differentiation and regeneration and apoptosis.

Additional components of the RAS have been identified in the last decade, including bioactive angiotensin peptides, such as angiotensin III, angiotensin IV, and angiotensin-(1-7), the effects of which have not yet been fully elucidated for the CV and renal system.

The discovery of the renin receptor has shed further light on the biology of the RAS. Renin, simply considered until recently as the rate-limiting enzyme of RAS activation, has also turned out to be the ligand for a protein known as the renin/prorenin receptor that binds renin and prorenin about equally, regardless of their biologic activities. Prorenin, which represents 70% to 90% of total circulating renin, when bound to the receptor induces an increase in the catalytic efficiency of angiotensinogen conversion to ATI, which contributes to local production of ATII and its systemic levels, as well as binding of renin/prorenin to the renin/prorenin receptor, exerting physiologic effects that are independent of ATII, including activation of intracellular signal pathways, enhanced synthesis of DNA, and stimulation of the release of plasminogen activator inhibitor 1, collagen 1, fibronectin, and transforming growth factor β-1.6

There are a number of known drugs which target the RAS. The two major classes of drugs that target the RAS are the angiotensin-converting enzyme (ACE) inhibitors and the selective ATI receptor blockers (ARBs). Although both of these drug classes target ATII, the differences in their mechanisms of action have implications for their effects on other pathways and receptors that may have therapeutic implications. Both ACEIs and ARBs are effective antihypertensive agents that have been shown to reduce the risk of cardiovascular and renal events.

Direct inhibition of renin, the most proximal aspect of the RAS, became clinically feasible from 2007 with the introduction of Aliskiren. This latter drug has been shown to be efficacious for the management of hypertension. Combined therapy of direct renin-inhibitors with ACEIs or ARBs has been tested in some clinical situations as congestive HF and proteinuria with diverse results.

RAS drugs include, but are not limited to, Angiotensin-Converting Enzyme Inhibitors (ACEIs), Angiotensin Receptor Blockers (ARBs), Direct Renin Inhibitors (DRIs), Beta-Blockers, Cyclo-oxygenase 2 Inhibitors, Chymase Inhibitors, Cathepsin Inhibitors including Cathepsin B Inhibitors, Cathepsin D Inhibitors and Cathepsin G Inhibitors, Calcium Channel Blockers, Calcium Supplements and Vitamin D, as described above.

Squamous Cell Carcinomas

Squamous cells are flat cells that form the surface layers of an epithelium. They can be identified histologically by the fact that they look flattened and thin under a microscope. Epithelia lined by squamous cells can be classified as either simple squamous epithelium or stratified squamous epithelium.

Squamous cell carcinomas refers to the epithelial tumours found in many different organs, including the skin, upper aerodigestive tract including the coral cavity, nasal cavity, oesophagus, lungs, cervix and gastrointestinal tract, which show squamous cell differentiation. Included are head and neck squamous cell carcinomas, lung squamous cell carcinomas, skin squamous cell carcinomas, otic squamous cell carcinomas, vulval squamous cell carcinomas, cervical squamous cell carcinomas, oesophageal squamous cell carcinomas, and the like. It is a malignant tumour of the epithelium that shows squamous cell differentiation. Squamous cell carcinoma is usually developed in the epithelial layer of the skin and sometimes in various mucous membranes of the body. This type of cancer can be seen on the skin, lips, inside the mouth, larynx or oesophagus.

The most common non-cutaneous tumour of the head and neck is squamous cell carcinoma of the of the upper aerodigestive tract (including larynx, oropharynx, oral cavity [including oral tongue and floor of the mouth]). Somewhat less common are tumours of the salivary gland, jaw, nose and paranasal sinuses, and ear.

Most head and neck cancers first manifest as an asymptomatic lump, ulceration, or visible mucosal lesion (e.g., leukoplakia, erythroplakia). Subsequent symptoms depend on location and extent of the tumour and include pain, paresthesia, nerve palsies, trismus, and halitosis. Head and neck cancers may remain localised for months to years. Local tissue invasion is eventually followed by metastasis to regional lymph nodes. Distant lymphatic metastases tend to occur late. Haematogenous metastases are usually associated with large or persistent tumours and occur more commonly in immunocompromised patients. Common sites of distant metastases are the lungs, liver, bone, and brain.

Oral cavity and oropharyngeal squamous cell carcinoma affects about 30,000 Americans each year. Oral squamous cell carcinoma is the most common oral cavity and oropharyngeal cancer. The chief risk factors for oral cavity squamous cell carcinoma are smoking and/or alcohol use. Squamous cell carcinoma of the oral tongue may also result, from Plummer-Vinson syndrome, syphilis, or chronic trauma. About 40% of oral cavity squamous cell carcinomas affect the oral tongue and 20% affect the floor of the mouth, with the remainder affecting the lip buccal mucosal, retromolar trigone, alveolus and hard palate. Oropharyngeal squamous cell carcinoma affects the base of the tongue and soft palate and tonsillar area and have been associated human papilloma virus infection with alcohol and smoking playing a lesser role.

Oral lesions are asymptomatic initially. They may appear in areas of erythroplakia or leukoplakia and may be exophytic or ulcerated. Both variants are indurated and firm with a rolled border. Oaropharyngeal cancer usually presents as an asymmetric swelling and sore throat; pain often radiates to the ipsilateral ear. A metastatic mass in the neck may be the first symptom.

If squamous cell carcinoma of the tongue is localised (no lymph node involvement), 5-yr survival is about 50%. For localised squamous cell carcinoma of the floor of the mouth, 5-yr survival is 65% but with lymph node metastasis, the 5-yr survival is 20%. For lower lip lesions, 5-yr survival is 90%, and metastases are rare. Squamous cell carcinoma of the upper lip tends to be more aggressive and metastatic. For oropharyngeal squamous cell carcinoma, 5-yr survival is 68% if patients are treated before lymph node involvement but only 17% after involvement. Metastases reach the regional lymph nodes first and later the lungs. Surgery and radiation therapy are the treatments of choice for oral cavity cancer. Radiotherapy and often chemotherapy are the treatment of choice for oropharyngeal cancer Characterization of Squamous Carcinoma Stem Cells In squamous cell carcinomas, characterisation of cancer stem cells allows for the development of new treatments that are specifically targeted against this critical population of cells, particularly their ability to self-renew, resulting in more effective therapies.

In human squamous cell carcinomas it is shown herein that there is a subpopulation of tumourigenic cancer cells with both self-renewal and differentiation capacity. These tumourigenic cells are responsible for tumour maintenance, and also give rise to large numbers of abnormally differentiating progeny that are not tumourigenic, thus meeting the criteria of cancer stem cells.

Cancer stem cells of squamous carcinoma are identified by their phenotype with respect to particular markers, and/or by their functional phenotype. In some examples, the these cancer stem cells are identified and/or isolated by binding to the cell with reagents specific for the markers of interest. The cells to be analysed may be viable cells, or may be fixed or embedded cells.

In some examples, the reagents specific for the markers of interest are antibodies, which may be directly or indirectly labeled. Such antibodies will usually include antibodies specific for CD44 and antibodies specific for a lineage panel. The lineage panel will usually include reagents specific for markers of normal leukocytes, fibroblasts, endothelial, mesothelial cells, etc. Such markers may include reagents specific for one or more, two or more, three or more of the following markers: CD44, SOX2, OCT4, NANOG, and a lack of expression of p63, CD34 and EMA.

Cancer Therapy—General

Any therapy (e.g., therapeutic or prophylactic agent) which is useful, has been used, or is currently being used for the prevention, treatment, and/or management of cancer can be used in compositions and methods of the present invention. Therapies (e.g., therapeutic or prophylactic agents) include, but are not limited to, peptides, polypeptides, antibodies, conjugates, nucleic acid molecules, small molecules, mimetic agents, synthetic drugs, inorganic molecules, and organic molecules. Non-limiting examples of cancer therapies include chemotherapies, radiation therapies, radioimmunotherapies, hormonal therapies, targeted therapies, epigenetic therapies, differentiation therapies, anti-angiogenic therapies small molecule therapies, epigenetic therapies, toxin therapies, differentiation therapies, prodrug activating enzyme therapies, antibody therapies, protein therapies, and/or biological therapies including immunotherapies, and surgery. In certain examples, a prophylactically and/or therapeutically effective regimen of the invention comprises the administration of a combination of therapies.

Examples of cancer therapies include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; histone deacetylase inhibitors (HDAC-Is); hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-nl; interferon alpha-n3; interferon beta-I a; interferon gamma-I b; iproplatin; irinotecan hydrochloride; lanreotide acetate; lenalidomide (Revlimid); letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safIngol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; /–/; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-D L-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone;

leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metal loproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumour suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocaφine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin 32; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone Bl; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; gamma secretase inhibitors, single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; anti-integrin antibodies (e.g., anti-integrin $\alpha_v\beta_3$ antibodies); vorozole; zanoterone; zeniplatin; zilascorb; and zinostatin stimalamer.

A non-limiting list of compounds that could be used to target cancer stem cells includes: inhibitors of interleukin-3 receptor (IL-3R) and CD123 (including peptides, peptide-conjugates, antibodies, antibody-conjugates, antibody fragments, and antibody fragment-conjugates that target IL-3R or CD123); cantharidin; norcantharidin and analogs and derivatives thereof; Notch pathway inhibitors including gamma secretase inhibitors; sonic hedgehog/smoothened pathway inhibitors including cyclopamine and analogs thereof; antibodies to CD96; certain NF-kB/proteasome inhibitors including parthenolide and analogs thereof; certain triterpenes including celastrol; certain mTOR inhibitors; compounds and antibodies that target the urokinase receptor; sinefungin; certain inosine monophosphate dehydrogenase (IMPDH) inhibitors; PPAR-alpha and PPAR-gamma agonists and antagonists (including pioglitazone, tesaslitazar, muraglitazar, peliglitazar, lobeglitazone, balaglitazone, ragaglitazar, rosiglitazone, farglitazar, sodelglitazar, reglitazar, naveglitazar, oxeglitazar, metaglidasen, netoglitazone, darglitazone, englitazone, thiazolidinediones, aleglitazar, edaglitazone, rivoglitazone, troglitazone, imiglitazar, and sipoglitazar); telomerase inhibitors; antibodies to EpCAM (ESA); GSK-3 beta agonists and antagonists (including Lithium, 6-bromoinirubin-3'-oxime (BIO), TDZD8); Wnt pathway inhibitors including antibodies to frizzled or small molecules that inhibit disheveled/frizzled or beta catenin; anti-CD20 antibodies and conjugates (e.g. Rituxan, Bexxar. Zevalin) for novel use in multiple myeloma or melanoma; anti-CD133 antibody; anti-CD44 antibody; antibodies to IL-4; certain differentiation agents such as versnarinone; compounds that target CD33 such as an antibody or betulinic acid; compounds that target lactadherin such as an antibody; small molecules or antibodies that target CXCR4 or SDF-I; small molecules or antibodies that target multi-drug resistance pumps; inhibitors of survivin; inhibitors of XIAP; small molecules that target Bcl-2; antibodies to CLL-I; and furin inhibitors (such as cucurbitacins). An additional non-limiting list of compounds that could also be used to target cancer stem cells includes i) antibodies, antibody fragments, and proteins that are either naked or conjugated to a therapeutic moiety that target certain cell surface targets on cancer stem cells, or ii) small molecules known in the art including ones that can be further optimized (e.g. via chemistry) or identified via a cancer stem cell-based screen (e.g. such as one that would determine whether a compound impairs proliferation or viability of a cancer stem cell through standard methods, the cell surface and intracellular targets including (not meant to be exhaustive) are: Rexl (Zfp42), CTGF, Activin A, Wnt, FGF-2, HIF-I, AP-2gamma, Bmi-1, nucleostemin, hiwi, Moz-TIF2, Nanog, beta-arrestin-2, OCT4, SOX2, stella, GDF3, RUNX3, EBAF, TDGF-I, nodal, ZFPY, PTNE, EvM$_5$ Pax3, Mcl-I, c-kit, Lex-1, Zfx, lactadherin, aldehyde dehydrogenase, BCRP, telomerase, CD133, Bcl-2, CD26, Gremlin, and FoxC2.

In some examples, the therapy(ies) used is an immunomodulatory agent. Non-limiting examples of immunomodulatory agents include proteinaceous agents such as cytokines, peptide mimetics, and antibodies (e.g., human, humanised, chimeric, monoclonal, polyclonal, Fvs, ScFvs, Fab or F(ab)$_2$ fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, Cytoxan, Immuran. cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamides (e.g., lefiunamide), T cell receptor modulators, cytokine receptor modulators, and mast cell modulators. Other examples of immunomodulatory agents can be found, e.g., in U.S. Publication No. 2005/0002934 A1 at paragraphs 259-275 which is incorporated herein by reference in its entirety. In one example, the immunomodulatory agent is a chemotherapeutic agent. In an alternative example, the immunomodulatory agent is an immunomodulatory agent other than a chemotherapeutic agent. In some examples, the therapy(ies) used in accordance with the invention is not an immunomodulatory agent.

In some examples, the therapy(ies) used is an anti-angiogenic agent. Non-limiting examples of anti-angiogenic agents include proteins, polypeptides, peptides, fusion proteins, antibodies (e.g., human, humanised, chimeric, monoclonal, polyclonal, Fvs, ScFvs, Fab fragments, F(ab)$_2$ fragments, and antigen-binding fragments thereof) such as antibodies that specifically bind to TNF-α, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publication No. 2005/0002934 A1 at paragraphs 277-282, which is incorporated by reference in its entirety. In other examples, the therapy(ies) used in accordance with the invention is not an anti-angiogenic agent.

In certain examples, the therapy used is an alkylating agent, a nitrosourea, an antimetabolite, and anthracyclin, a topoisomerase II inhibitor, or a mitotic inhibitor. Alkylating agents include, but are not limited to, busulfan, cisplatin, carboplatin, cholorambucil, cyclophosphamide, ifosfamide, decarbazine, mechlorethamine, mephalen, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etopiside (VP-16), and teniposide. Mitotic inhibitors include, but are not limited to taxanes (paclitaxel, docetaxel), and the vinca alkaloids (vinblastine, vincristine, and vinorelbine).

The invention includes the use of agents that target cancer stem cells. In certain examples, the agent is a small molecule, biologic, or an agent including a peptide or antibody or antibody fragment that is naked or is attached directly or indirectly to a therapeutic moiety via chemical or recombinant technology. Non-limiting examples of therapeutic moieties include, but are not limited to, therapeutic enzymes, chemotherapeutic agents, cytokines, bacterial toxins, diphtheria toxin, Pseudomonas exotoxin, radionuclides, RNase, and antimetabolites. In some examples, the agent used is an agent that binds to a marker, e.g., an antigen on a cancer stem cell. In a specific example, the agent binds to an antigen that is expressed at a greater level on cancer stem cells than on normal stem cells. In another specific example the agent binds to an antigen that is expressed at the same level on cancer stem cells as on normal stem cells.

In a specific example, the agent binds specifically to a cancer stem cell antigen that is not, or is, on a normal stem cell. In other examples, the therapy(ies) used in accordance with the invention is an agent that binds to a marker on cancer stem cells, In one example, the agent that binds to a marker on cancer stem cells is an antibody or antibody fragment—either of which may be naked or conjugated to a therapeutic moiety such as therapeutic enzymes, chemotherapeutic agents, cytokines, bacterial toxins, diphtheria toxin, Pseudomonas exotoxin, radionuclides, RNase, and antimetabolites.

For example, in a specific example, the agent binds specifically to the IL-3 Receptor (IL-3R) or the α-subunit thereof (i.e., the CD123 antigen). In some examples, the agent that binds to the IL-3R is an antibody that is specific for IL-3R or the α-subunit thereof. The antibody may be conjugated to a therapeutic moiety (e.g., a chemotherapeutic agent, a plant-, fungus- or bacteria-derived toxin, or a radionuclide, RNase) using a linking agent, either chemically or recombinantly, to effect a cell killing response. In certain examples, the antibody or antibody-conjugate binds to the α-subunit of IL-3R (i.e., the CD1 23 antigen). In other words, the antibody or antibody-conjugate binds to the IL-3R α-subunit but not the IL-3R β-subunit. In other examples, the antibody or antibody-conjugate immuospecifically binds to the IL-3R, containing both the α and β subunits. Methods for preparing antibodies to IL-3R and mimetics of antibodies to IL-3R are described, e.g., in U.S. Pat. No. 6,733,743 B2, which is incorporated herein by reference in its entirety.

In other examples, the agent that binds to a marker on cancer stem cells is a ligand. In some examples, the ligand is a cytokine that binds to a cytokine receptor on cancer stem cells. In a particular example, the ligand is interleukin-3 (IL-3) which can be conjugated to a therapeutic moiety including a toxin. The IL-3-toxin conjugate can be in the form of a fusion protein in examples where the toxin is a protein, such as diphtheria toxin. Methods for preparing and isolating an IL-3-diphtheria toxin fusion protein ("IL3DT") are described in Frankel et al., "Diphtheria toxin fused to human interleukin-3 is toxic to blasts from patients with myeloid leukemias," Leukemia 14:576 (2000) and Urieto et al., "Expression and purification of the recombinant diphtheria fusion toxin DT388IL3 for phase I clinical trials," Protein Expression and Purification 33: 123-133 (2004)," the disclosures of which are incorporated by reference in their entireties. In other examples, the therapy is not IL3DT.

In certain examples, antibodies that bind to a marker on cancer stem cells are substantially non-immunogenic in the treated subject. Methods for obtaining non-immunogenic antibodies include, but are not limited to, chimerizing the antibody, humanising the antibody, generating antibody fragments, and generating antibodies from the same species as the subject receiving the therapy. See, for example, paragraphs 539-573 of U.S. Publication No. 2005/0002934 A1, which is incorporated by reference in its entirety. Antibodies that bind to markers in cancer stem cells can be produced using techniques known in the art.

In some examples, the therapy used comprises the use of x-rays, gamma rays and other sources of radiation to destroy cancer stem cells and/or cancer cells. In specific examples, the radiation therapy is administered as external beam radiation or teletherapy, wherein the radiation is directed from a remote source. In other examples, the radiation therapy is administered as internal therapy or brachytherapy wherein a radioactive source is placed inside the body close to cancer stem cells, cancer cells and/or a tumour mass.

In some examples, the therapy used is a proliferation based therapy. Non-limiting examples of such therapies include a chemotherapy and radiation therapy as described supra.

Currently available therapies and their dosages, routes of administration and recommended usage are known in the art and have been described in such literature as the Physician's Desk Reference ($60^{th}$ ed., 2006). Routes of administration known in the art include, without limitation, oral, topical, parenteral, sublingual, rectal, vaginal, ocular, intradermal, intratumoural, intracerebral, intrathecal, and intranasal. In some examples, the therapies are administered as part of a composition comprising a pharmaceutically acceptable carrier or excipient.

In Vitro Assays

The therapies described herein can be tested in vitro and/or in vivo for their ability to reduce the amount of cancer cells and/or cancer cells, or inhibit their proliferation. The ability of a therapy to stabilize or reduce the amount of cancer stem cells, cancer cells and/or immune cells (e.g., lymphocytes) or inhibit their proliferation can be assessed by: detecting the expression of antigens on cancer stem cells, cancer cells, and immune cells; detecting the proliferation cancer stem cells, cancer cells and immune cells; detecting the cancer stem cells and cancer cells using functional assays. Techniques known to those of skilled in the art can be used for measuring these activities. For example, cellular proliferation can be assayed by $^3$H-thymidine incorporation assays and trypan blue cell counts. Antigen expression can be assayed, for example, by immunoassays including, but are not limited to, competitive and non-competitive assay systems using techniques such as Western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, immunofluorescence, flow cytometry, and FACS analysis.

A compound, pharmaceutical composition, therapeutic or prophylactic agent of the present invention may be tested in vitro and then in vivo for the desired therapeutic or prophylactic activity prior to use in humans. For example, assays which can be used to determine whether administration of a specific compound is effective include cell and tissue culture assays in which a patient tissue sample (e.g., a cancer cell or cancer stem cell) is grown in culture and exposed to, or otherwise contacted with, a compound, and the effect of such compound upon the tissue sample is observed. The tissue sample can be obtained by biopsy from the patient. This test allows the identification of the therapeutically most effective therapy (e.g., prophylactic or therapeutic agent) for each individual patient.

A therapy is preferably tested in vitro and then in vivo for the desired therapeutic or prophylactic activity prior to use in humans. For example, assays which can be used to determine whether administration of a specific compound is effective include cell and tissue culture assays in which a patient tissue sample (e.g., a cancer cell or cancer cell) is grown in culture and exposed to, or otherwise contacted with, a prophylactic or therapeutic compound, and the effect of such compound upon the tissue sample is observed. The tissue sample can be obtained by biopsy from the patient. This test allows the identification of the therapeutically most effective therapy (e.g., prophylactic or therapeutic agent) for each individual patient. In certain examples, the effect of a therapy is assessed in a cell viability assay using standard assays known in the art such as, for example, the XTT assay.

Toxicity Assays

The toxicity and/or efficacy of the therapies described herein can be determined by standard pharmaceutical procedures in cell or tissue cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD5_0/ED_{50}$-Regimens that exhibit large therapeutic indices are preferred. While regimens that exhibit toxic side effects may be used, care should be taken to design a delivery system that targets such agents to the site of affected tissue in order to minimise potential damage to uninfected cells and, thereby, reduce side effects.

The data obtained from the cell culture assays and animal studies can be used in formulating a range of dosage of the therapies for use in humans. The dosage of such agents lies preferably within a range of circulating concentrations that include the ED50 with little or no toxicity to normal tissues. The dosage may vary within this range depending upon the dosage form employed and the route of administration utilised. For any therapy used in the method of the invention, the prophylactically and/or therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels of compounds in plasma may be measured, for example, by high performance liquid chromatography.

Articles of Manufacture

The present invention also encompasses a finished packaged and labelled pharmaceutical product(s). This article of manufacture includes the appropriate unit dosage form in an appropriate vessel or container such as a glass vial or other container that is hermetically sealed. The pharmaceutical product may contain, for example, a prophylactic or therapeutic agent in a unit dosage form in a first container, and in a second container, sterile water for injection. Alternatively, the unit dosage form may be a solid suitable for oral, transdermal, intranasal, or topical delivery.

In a specific example, the unit dosage form is suitable for intravenous, intramuscular, intranasal, oral, topical or subcutaneous delivery. Thus, the invention encompasses solutions, preferably sterile, suitable for each delivery route.

In some examples, the pharmaceutical product is a prophylactic and/or therapeutic agent disclosed herein. In some examples, the pharmaceutical product is a composition comprising a prophylactic and/or therapeutic agent and a pharmaceutically acceptable carrier or excipient. In a specific example, the pharmaceutical composition is in a form for an appropriate route of administration. Such routes include, without limitation, oral, topical, parenteral, sublingual, rectal, vaginal, ocular, intradermal, intratumoural, intracerebral, intrathecal, and intranasal routes.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, the frequency of administration, the duration of administration monitoring procedures for cancer cell counts, cancer stem cell counts, lymphocyte counts, neutrophil counts, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises a prophylactic or therapeutic agent, and wherein said packaging material includes instruction means which indicate that said agent can be used to prevent, manage, treat, and/or ameliorate one or more symptoms associated with cancer, or one or more symptoms thereof by administering specific doses and using specific dosing regimens as described herein.

In certain examples, the article of manufacture include labeled antibodies that selectively or specifically bind to cancer stem cells, and that selectively or specifically bind to cancer cells. As such, the article contains a method to adjust the dosages used in the treatment regimens, and to monitor the efficacy of the regimens.

The present invention provides that the adverse effects that may be reduced or avoided by the methods of the invention are indicated in informational material enclosed in an article of manufacture for use in preventing, treating and/or managing cancer. Adverse effects that may be reduced or avoided by the methods of the invention include, but are not limited to, vital sign abnormalities (fever, tachycardia, bardycardia, hypertension, hypotension), haematological events (anemia, lymphopenia, leukopenia, thrombocytopenia), headache, chilis, dizziness, nausea, asthenia, back pain, chest pain (chest pressure), diarrohea, myalgia, pain, pruritus, psoriasis, rhinitis, sweating, injection site reaction, and vasodilation.

Further, the information material enclosed in an article of manufacture for use in preventing, treating and/or managing cancer can indicate that foreign proteins may also result in allergic reactions, including anaphylaxis, or cytosine release syndrome. The information material should indicate that allergic reactions may exhibit only as mild pruritic rashes or they may be severe such as erythroderma, Stevens-Johnson syndrome, vasculitis, or anaphylaxis. The information material should also indicate that anaphylactic reactions (anaphylaxis) are serious and occasionally fatal hypersensitivity reactions. Allergic reactions including anaphylaxis may occur when any foreign protein is injected into the body. They may range from mild manifestations such as urticaria or rash to lethal systemic reactions. Anaphylactic reactions occur soon after exposure, usually within 10 minutes. Patients may experience paresthesia, hypotension, laryngeal oedema, mental status changes, facial or pharyngeal angioedema, airway obstruction, bronchospasm, urticaria and pruritus, serum sickness, arthritis, allergic nephritis, glomerulonephritis, temporal arthritis, or eosinophilia.

Kits

The present invention also provides a pharmaceutical pack or kit comprising one or more containers filled with reagents for detecting, monitoring and/or measuring cancer stem cells. In one example, the pharmaceutical pack or kit optionally comprises instructions for the use of the reagents provided for detecting and/or measuring cancer stem cells. In another example, the pharmaceutical pack or kit optionally comprises a notice in the form prescribed by a governmental agency regulating the manufacture, use or sale of pharmaceuticals or biological products, which notice reflects approval by the agency of manufacture, for use or sale for human administration.

In an example, the pharmaceutical pack or kit comprises in one or more containers a cancer stem cell surface marker-binding agent. In certain examples, the agent is an antibody that selectively or specifically binds to a cancer stem cell surface marker. The agent may be an antibody (including, e.g., human, humanised, chimeric, monoclonal, polyclonal, Fvs, ScFvs, Fab or F(ab)2 fragments or epitope binding fragments), which cross-reacts with any cancer stem cell surface marker. In another example, the antibody reacts with any one of the cancer stem cell surface markers listed in Table 1 of U.S. Pat. No. 6,004,528 or Tables 1, 2, or 3 of U.S. patent application Ser. No. 09/468,286, and U.S. Patent Application Publication Nos. 2006/0083682, 2007/0036800, 2007/0036801, 2007/0036802, 2007/0041984, 2007/0036803, and 2007/0036804, each of which is incorporated by reference herein. In accordance with this example, the pharmaceutical pack or kit comprises one or more antibodies which bind to cancer stem cell surface markers, wherein each antibody binds to a different epitope of the cancer stem cell surface marker and/or binds to the cancer stem cell surface marker with a different affinity.

For antibody based kits, the kit can comprise, for example: (1) a first antibody (which may or may not be attached to a solid support) which binds to a cancer stem cell surface marker protein; and, optionally, (2) a second, different antibody which binds to either the cancer stem cell surface marker protein bound by the first antibody, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analysing the data resulting from the performance of the assay. As an example, a kit may include an anti-CD34 antibody for positive selection, an anti-CD38 antibody for negative selection, and an anti-CD123 antibody for positive selection to isolate and/or quantify and/or assist in the determination of the amount of leukemia cancer stem cells (which are CD34+/CD38−/CD123+).

For nucleic acid micoarray kits, the kits generally comprise (but are not limited to) probes specific for certain genes attached to a solid support surface. In other examples, the probes are soluble. In one such example, probes can be either oligonucleotides or longer length probes including probes ranging from 150 nucleotides in length to 800 nucleotides in length. The probes may be labeled with a detectable label. The microarray kits may comprise instructions for performing the assay and methods for interpreting and analysing the data resulting from the performance of the assay. The kits may also comprise hybridization reagents and/or reagents necessary for detecting a signal produced when a probe hybridizes to a cancer stem cell surface marker nucleic acid sequence. Generally, the materials and reagents for the microarray kits are in one or more containers. Each component of the kit is generally in its own suitable container.

For Quantitative PCR, the kits generally comprise preselected primers specific for certain cancer stem cell surface marker nucleic acid sequences. The Quantitative PCR kits may also comprise enzymes suitable for amplifying nucleic acids (e.g., polymerases such as Taq), and deoxyribonucleotides and buffers needed for the reaction mixture for amplification. The Quantitative PCR kits may also comprise probes specific for the nucleic acid sequences associated with or indicative of a condition. The probes may or may not be labeled with a flourophore. The probes may or may not be labeled with a quencher molecule. In some examples, the Quantitative PCR kits also comprise components suitable for reverse-transcribing RNA including enzymes (e.g., reverse transcriptases such as AMV, MMLV and the like) and primers for reverse transcription along with deoxynucleotides and buffers needed for the reverse transcription reaction. Each component of the quantitative PCR kit is generally in its own suitable container. Thus, these kits generally comprise distinct containers suitable for each individual reagent, enzyme, primer and probe. Further, the quantitative PCR kits may comprise instructions for performing the assay and methods for interpreting and analysing the data resulting from the performance of the assay.

A kit can optionally further comprise a predetermined amount of an isolated cancer stem cell surface marker polypeptide or a nucleic acid encoding a cancer stem cell surface marker, e.g., for use as a standard or control. The diagnostic methods of the present invention can assist in conducting or monitoring a clinical study. In accordance with the present invention, suitable test samples, e.g., of serum or tissue, obtained from a subject can be used for diagnosis.

Based on the results obtained by use of the pharmaceutical pack or kit (i.e. whether the cancer stem cell amount has stabilised or decreased), the medical practitioner administering the cancer therapy or regimen may choose to continue the therapy or regimen. Alternatively, based on the result that the cancer stem cell amount has increased, the medical practitioner may choose to continue, alter or halt the therapy or regimen.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

The invention is further described with reference to the following examples. It will be appreciated that the invention as claimed is not intended to be limited in any way by these examples.

EXAMPLES

Example 1: Materials and Methods

Materials
Antibodies

The antibodies used for immunohistochemistry, their optimised dilutions and sources are listed in alphabetical order in Table 1.

TABLE 1

Antibodies, Dilution and Sources

| Antibody | Species | Source | Optimised Dilution - DAB Autostainer IHC | Optimised Dilution - Fluorescent IHC | Optimised Antibody Dilution - WB | Control tissue |
| --- | --- | --- | --- | --- | --- | --- |
| Santa Cruz Biotechnology Nanog | Rabbit | Newcastle upon Tyne, UK | | 1:300 | 1:200 | Seminoma |
| Abcam Renin Receptor | Rabbit | Billerica, Ma, USA | 1:1000 | 1:1000 | | Placenta |
| Cell Marque Oct-4 | Mouse Monoclonal | Santa Cruz, Ca, USA | | 1:300 | | Seminoma |
| Thermo Fisher Scientific Sox2 | Rabbit polyclonal | Santa Cruz, California, USA | 1:2000 | 1:500 | | Colon Cancer |
| Life Technologies β-actin | Mouse monoclonal | Rockford, Il, USA | | | 1:5000 | Ubiquitously expressed |
| Abcam Secondary antibody | Goat anti-Rabbit | Carlsbad, Ca, USA | | 1:500 | | |
| Abcam Secondary antibody | Sheep anti-Mouse | Carlsbad, Ca, USA | | 1:500 | | |
| Abcam Secondary HRP conjugated antibody | Goat anti-Mouse | Carlsbad, Ca, USA | | | 1:2000 | |
| Abcam Secondary HRP conjugated antibody | Sheep anti-goat | Carlsbad, Ca, USA | | | | |

TABLE 1-continued

Antibodies, Dilution and Sources

| Antibody | Species | Source | Optimised Dilution - DAB Autostainer IHC | Optimised Dilution - Fluorescent IHC | Optimised Antibody Dilution - WB | Control tissue |
|---|---|---|---|---|---|---|
| Abcam Secondary HRP conjugated antibody | Goat anti-Rabbit | Carlsbad, Ca, USA | | | 1:2000 | |
| Life Technologies Alexafluor Fluorophore 488 | Goat anti-Mouse | Cambridge, England | | 1:500 | | |
| Life Technologies, Alexafluor Fluorophore 488 | Donkey anti-sheep | Cambridge, England | | 1:500 | | |
| Life Technologies Alexafluor 555 | Goat Anti-Mouse | Carlsbad, Ca, USA | | | 1:2000 | |
| Life Technologies Alexafluor 594 | Goat anti-Rabbit | Carlsbad, Ca, USA | | 1:500 | | |
| Life Technologies Fluorophore 647 | Chicken anti-Goat | Carlsbad, Ca, USA | | 1:500 | | |
| Life Technologies, Alexafluor 647 | Goat Anti-Rabbit | Carlsbad, Ca, USA | | | 1:2000 | |
| Abcam Fluorophore | Goat Anti-Mouse | Carlsbad, Ca, USA | | | 1:2000 | |
| Abcam Fluorophore | Goat Anti-Rabbit | Carlsbad, Ca, USA | | | 1:2000 | |
| Bio-Rad Prestained SDS-PAGE Standards, Broad Range | — | Cambridge, England | | — | — | |
| Bio-Rad Precision Plus Protein™ Dual Xtra Standards | — | Cambridge, England | | — | — | |

Chemicals and Reagents

The Chemicals and Reagents used in this study and their sources are listed in Table 2.

TABLE 2

| Chemicals and Reagents | |
|---|---|
| Emsure Sodium Chloride | Darmstadt, Germany |
| Emsure Potassium Chloride | Darmstadt, Germany |
| Sigma-Aldrich Sodium Citrate, pH 6 2.491 g Citrate, 1000 mL ddH2O, pH 6 | St Louis, Mo, USA |
| Sigma-Aldrich Tween 20 ™ | St Louis, Mo, USA |
| Sigma-Aldrich Sodium Borohydride | St Louis, Mo, USA |
| Sigma-Aldrich Bovine Serum Albumin (BSA) | St Louis, Mo, USA |
| Merck 1,4 Dithiothrietol (DTT) | Darmstadt, Germany |
| GE Healthcare 2-D Quant Kit BSA Standard Copper Solution Colour Reagent A Colour Reagent B Precipitant Co-Precipitant | Piscataway, NJ, USA |
| Leica Micromount, Invitrogen Gold Antifade containing DAPI | Nussloch, Germany |
| Leica Surgipath$^R$ Micromount$^R$ Mounting Medium | Nussloch, Germany |

Buffers, Solutions and Stains

The buffers, solutions and stains used in this study are listed in Table 3.

TABLE 3

| Buffers, solutions and stains | |
|---|---|
| Sigma Aldrich SAFC$^R$ Tris Hydrochloride | St Louis, Mo, USA |
| Sigma Aldrich Tween20 ™ | St Louis, Mo, USA |
| Tris-Buffered Saline (TBS), pH 7.6 10X: 80 g (Sigma Aldrich) NaCl, 2 g (Sigma Aldrich) KCl, 30 g Tris Base, 1000 mL ddH2O TBS/Tween (TBST, TBS + 1% Tween20) Phosphate-Buffered Saline (PBS), pH 7.4 10X: 80 g (Sigma Aldrich) NaCl, 2 g (Sigma Aldrich) KCl, 14.4 g Na$_2$HPO$_4$, 2.4 g KH$_2$PO$_4$, 1000 mL ddH$_2$0 PBS/Tween (PBST, PBS + 1% Tween20) | |
| Bio-Rad ReadyPrep ™ Bio Protein Extraction kit (Reducing): 5.6 mL ReadyPrep Proteomic grade water One vial containing 5.6 g Buffer Powder 10 uL tributyl phosphine (TBP, reducing agent) | Hercules, Ca, USA |

TABLE 3-continued

Buffers, solutions and stains

| | |
|---|---|
| Transfer contents of 1 mL ampoule to screw cap storage vial provided | |
| Store remaining at −80 C. | |
| Sigma Aldrich Life Science RIPA buffer | St Louis, Mo, USA |
| Thermo Fisher scientific Halt ™ Protease & Phosphatase Inhibitor Cocktail | Rockford, Il, USA |
| Bio-Rad 2x Laemmli Sample Buffer | Hercules, Ca, USA |
| Bio-Rad 2-mercaptoethanol | Hercules, Ca, USA |
| Bio-Rad 10X Tris/Glycine/SDS Buffer SDS-PAGE Running Buffer | Hercules, Ca, USA |
| Life Technologies ™, Molecular Probes$^R$ Qubit$^R$ Protein assay Kit: Qubit$^R$ Protein Buffer Qubit$^R$ Protein reagent | Carlsbad, Ca, USA |
| Life Technologies, Novex, iBind ™ Solution Kit iBind ™ 5x Buffer iBind ™ 100x Additive | Carlsbad, California, USA |
| Life Technologies, Novex, iBind ™ FD Solution Kit iBind ™ 5x Buffer iBind ™ 100x Additive iBind ™ 10% SDS | Carlsbad, California, USA |
| Life Technologies ™ Qubit$^R$ Protein Standards | Eugene, Or, USA |
| Bio-Rad Clarity ™ Western ECL Substrate Kit: Luminol/enhancer solution Peroxide solution | Hercules, Ca, USA |
| Leica Bond ™ Dewax Solution. | Nussloch, Germany |

The kits used for the autostainer immunohistochemistry and their sources are listed in Table 4.

TABLE 4

Immunohistochemistry Autostainer Kits

| Autostainer Kit | Cat# | Source |
|---|---|---|
| | Cat#AR9222 | Nussloch, Germany |
| Leica Bond ™ Primary Antibody Diluent | Cat#AR9352 | Nussloch, Germany |
| Leica Bond ™ Enzyme Pretreatment Kit | Cat#AR9551 | Nussloch, Germany |
| Leica Bond ™ Epitope Retrieval Solution 1 | Cat#AR9961 | Nussloch, Germany |
| Leica Bond ™ Epitope Retrieval Solution 2 | Cat#AR9640 | Nussloch, Germany |
| Leica Bond ™ Intense R Detection | Cat#DS9263 | Nussloch, Germany |
| Leica Polymer Bond ™ Intense Refine Red Detection | Cat#DS9390 | Nussloch, Germany |
| Leica Polymer Bond ™ Intense Refine Detection | Cat#DS9800 | Nussloch, Germany |

Methods
Formalin-Fixed Paraffin-Embedded Section Preparation 4 um sections of formalin fixed and paraffin-embedded SCCOT sections were cut using a microtome, stretched in a water-bath at 40° C., transferred onto glass slides and dried at room temperature overnight.

H&E Staining

H&E staining was performed on one formalin fixed and paraffin embedded slide per patient.

H&E Staining Analysis

H&E stained slides were used for initial grading of lesions into well-differentiated, moderately-differentiated and poorly-differentiated groups by a consultant pathologist. They were subsequently used as a reference for tissue morphology and orientation of IHC staining patterns within the specimens.

Automated Fluorescent Immunohistochemistry Procedure

Automated fluorescent immunostaining with either double stains, triple stains, or quadruple stains was performed according to protocols provided by the manufacturer, using a Leica Bond RX Immunohistochemistry Autostainer, Nussloch, Germany.

Automated DAB Immunohistochemistry Staining Procedure

Automated DAB immunostaining with single stains was performed according to protocols provided by the manufacturer, using a Leica Bond RX Immunohistochemistry Autostainer, Nussloch, Germany.

Visualisation, Photography, and Image Analysis

DAB stained slides were viewed with an Olympus BX53 microscope, and an Olympus SC100 microscope camera.

DAB immunostained slides were viewed and captured using an Olympus BX53 Microscope, and Olympus SC100 Microscope Camera. Qualitative analyses of the images were described as either non-staining, weak-positive staining, strong positive staining. Observations about the location of positive staining within the tissue, morphology of positive cells, and apparent location of staining within positive staining cells were also noted.

Fluorescent immunostained slides were viewed and captured using an Olympus FV1200 biological confocal laser-scanning microscope from Tokyo, Japan.

Qualitative analyses of the images were described as either non-staining, staining or co-staining.

Localisation of marker expression within cells was analysed using FV-10 software, generating the relative intensity of expression of multiple markers across the diameter of single cells. Expression was separated into nuclear, cytoplasmic, and membranous regions. The average staining intensity within each of these portions was calculated in 9 individual cells per patient. This allowed generalisations to be made regarding the precise localisation of staining within the cells of that patient. For example 70% nuclear, 30% cytoplasmic, 0% membranous.

Western Blotting
Sample Handling and Preparation

Surgical specimens were transferred directly from the operating theatre to the GMRI laboratory where they were placed into Cryovials and snap frozen with liquid nitrogen and stored at −80° C.

Snap-frozen tissues were taken from the freezer and dissected to an appropriate size (40-80 mg). The mass of the sample to be used was recorded, and any remaining tissue was immediately returned to the original Cryovial and stored at −80° C. for future research. Samples were kept on ice as much as possible.

Samples were added to individual Eppendorf tubes containing RIPA buffer and a protease inhibitor, 10 mg/500 uL/5 uL, and then transferred to a glass mortar and ground on ice with a pestle, until homogenized. The tissue suspension was then returned to the eppendorf tube, incubated on ice for 5 minutes, then centrifuged for at 13300 rpm 4° C. for 20 minutes. The supernatant was then transferred to a new Eppendorf tube, and stored on ice. The pellet was discarded.

Protein Assay

Qubit™ Working Solution was prepared by diluting 1 ul Qubit™ Reagent with 199 ul Qubit™ Buffer to make 200 uL for each of the standards and samples. Three protein standards were then prepared using 10 ul (protein standards) added to 190-199 ul Qubit™ Working Solution. Standards were then vortexed for 2-3 seconds, and incubated at room temperature for 2 minutes. Each of the standards was then placed into the Qubit™ 2.0 fluorometer sequentially to derive a standard curve.

Experimental protein samples were prepared using 10 uL of lysate added to 190 uL of Qubit™ Working Solution to make up 200 ul. Samples were then read using the Qubit™ 2.0 Fluorometer, and the protein concentration in the original stock sample was calculated using the dilution calculator feature.

If the sample protein concentration could not be read n because there was excess protein in the sample, the lysate was diluted and the process repeated until a satisfactory reading was obtained.

Tissue lysate samples were then aliquoted into eppendorf tubes to reduce contamination risk and damage caused by repeated freeze/thaw cycles and then stored at −80° C. for later use.

Lysate samples were retrieved from the freezer, and kept on ice. The volume of each sample was calculated based on the protein concentrations (to allow loading of equal amounts of protein per well on the gel) and then Extraction buffer was added to these so that each sample was of equal volume (10 uL).

Working solution (9.5 uL of Laemmli buffer and 0.5 uL β-mercaptoethanol) was prepared to make 10 uL per sample. 10 uL sample and 10 uL working solution was then boiled on a heating block for 10 minutes.

Gel Electrophoresis

Laemmli SDS-PAGE running buffer was prepared by adding 100 mL 10× stock to 900 mL ddH20.

The comb and tape were removed from a mini-SDS PAGE gel and the Mini-Protean tetra cell was assembled and the inner and outer chambers were filled with 1× running buffer.

2.5 uL of the protein standard (molecular weight markers) was loaded into gel well 1 and 20 uL of the protein samples were loaded into the remaining wells.

The gel was then run at 110V for 5 minutes until the samples entered the gel and the voltage was then increased to 200V to for 30 minutes. The gel was then removed, and the wells and bottom of the gel (containing loading dye) were cut off with a scalpel.

Semi-Dry Transfer of Gel to Membrane

The transfer sandwich was assembled in the Bio-Rad Trans-Blot Turbo™ Transfer system, in the correct order: filter paper, PVDF membrane, gel, filter paper. A small amount of 1× running buffer was applied to wet the membrane and the roller was used to remove any trapped air bubbles. The chamber was then closed and the transfer initated with the correct settings (TURBO, 1 MINI GEL (1,3A, 25V, 7 min) A: Run) and run for 7 minutes. The blot was then removed from the sandwich and placed briefly in working solution.

Immunodetection

1× iBind™ solution was prepared with 23.7 mL ddH20 and 300 uL Additive and 6 mL iBind™ buffer. The blotted membrane was immersed for 10 minutes in 10 mL of the iBind™ solution on a rocking platform. An iBind™ Card was placed on the stage of the iBind™ Western Device, and 5 mL of 1× iBind™ solution was pipetted evenly across the flow region, with an additional 1 mL of iBind™ solution pooled in the centre of the card. The blotted membrane was then placed on the iBind™ Card with the protein side down and the low molecular weight region closest to the stack. The blotting roller was then used to remove any air bubbles, and the lid was closed. Antibodies and 1× iBind™ solution were then added to the wells in the following sequence. 1: Primary antibody (5× concentration) in 2 mL of working solution, 2: 2 mL iBind™ solution, 3: HRP secondary antibody (5× concentration) in 2 mL of working solution, 4: 6 mL iBind™ solution, and incubated for 2.5 hours or overnight at room temperature.

Imaging and Data Analysis

The blotted membrane was rinsed in tap water for 5 minutes on a rocking platform. The chemiluminescent substrate kit (Clarity™ Western ECL Substrate Kit) was prepared in a 1:1 ratio: 7 mL Luminol enhancer solution and 7 mL peroxide solution and incubated for 15 minutes on a rocking platform. The chemiluminescent signals were then captured using a Bio-Rad ChemiDoc™ MP Imaging System, and Bio-Rad Image Lab™ Software Version 5.0.

Re-Probing

Blotted membranes were stored in TBST at 4 degrees C. When required, blotted membranes were re-probed for an additional marker. The blotted membrane was washed in tap water for 10 minutes on a rocking platform, and then incubated in 10 mL of iBind™ solution for 10 minutes on a rocking platform. iBind™ Card, iBind™ working solution and antibodies were prepared as previously described, with the exception of using fluorescent secondary antibodies rather than HRP secondary antibodies. The membrane was then incubated for 3.5 hours.

Protein Quantification

Protein extracted from an initial sample of poorly differentiated tongue SCC sample. Protein quantification was performed using the 2-D Quant kit. Protein standards were prepared by placing 0 uL, 10 uL, 20 uL, 30 uL, 40 uL, 50 uL of BSA solution into Eppendorf tubes. OTSCC and control tissue (placenta) samples were prepared covering a range of protein lysates (2 uL, 5 uL, 15 uL, 30 uL) in Eppendorf tubes. 500 uL of precipitant solution was added to each, and each tube was vortexed for 5 seconds. 500 uL of co-precipitant was then added to each tube and again vortexed for 5 seconds. All protein standards and solutions were then centrifuged at 13,300 rpm for 15 minutes. The supernatant was poured off and discarded and the tubes were again centrifuged briefly to move all remaining solution from the bottom of the tubes. This solution was then pipetted off, taking care not to disturb the pellet.

500 uL copper solution was prepared for each of the protein standards and samples, 1:5 copper solution:ddH2O. 500 uL copper solution was then added to each of the tubes, and vortexed for 5 seconds, to re-dissolve the precipitated protein.

1000 uL of colour reagent solution was prepared for each of the protein standards and samples, 1:200 colour reagent A:colour reagent B. 1000 uL of colour reagent solution was added to each tube and left to develop for 5 minutes. 200 uL each of ddH20, standard solutions and samples were loaded sequentially to a well plate.

The well plate was placed in a plate-reader. A standard curve was generated from the standard solutions, and the absorbance of samples were read at 480 nm. The standard curve was then generated and the samples read against it, to give a total protein concentration in mg/mL in the stock sample protein lysate.

Example 2: Expression Analysis in Squamous Cell Carcinoma of Oral Cavity

The following markers were analysed in tissue samples obtained from patients having squamous cell carcinoma of oral tongue (SCCOT).

1. Embryonic Stem Cell Markers

OCT4: Embryonic stem cell marker, associated with maintenance of pluripotency and self-renewal, not expressed in normal adult tissues. Transcription factor with expression normally confined to the nucleus although some cytoplasmic expression in cancer cells has been noted in the literature (also noted in our results).

NANOG: Embryonic stem cell marker, associated with maintenance of pluripotency and self-renewal, expression controlled by SOX2 and OCT4. Transcription factor with expression normally confined to nucleus, but again some cytoplasmic expression in cancer cells has been noted in the literature (also noted in our results).

SOX2: Embryonic stem cell marker, associated with maintenance of pluripotency and self-renewal. Transcription factor with expression mainly in the nucleus but again some cytoplasmic expression in cancer cells has been noted in the literature (also noted in our results).

pSTAT3: Activated Signal Transducer and Activator of Transcription. Known stem cell marker associated with maintenance of pluripotency, self-renewal. Constitutive activation of pSTAT3 is recognised in cancer, playing a key role in control of cell-cycle progression and anti-apoptosis and angiogenesis.

The results of the marker expression and marker co-localisation analyses performed on squamous cell carcinoma of oral tongue (SCCOT) samples are summarised in Table 5, below.

TABLE 5

Summary of marker expression within moderately differentiated sections of SCC of the oral tongue (to date). Investigation of co-localisations.

| Auto-stainer | Antibody against protein marker 1 | Antibody against protein marker 2 | Co-expression? | Interpretation |
| --- | --- | --- | --- | --- |
| Auto-stainer | CD44 (Ms)* | NANOG (Rb)* | Yes | Primitive cancer stem cell population |
| Auto-stainer | CD44 (Ms)* | SOX2(Rb)* | Yes | Primitive cancer stem cell population |
| Auto-stainer | EMA (Ms)* | SOX2(Rb)* | No | EMA cells are more differentiated (downstream) of SOX2 positive cells |

*(Rb) primary antibody raised in rabbit
(Ms) primary antibody raised in mouse

8. Positive Controls

Positive control tissues (target protein specific) were identified, tested and then stained simultaneously with experimental tissues on the autostainer.

9. Results

The results of these data show:
1. Definitive co-localisation of cancer stem cell markers within tongue cancer. The proteins that have been co-localised within this cancer stem cell population to date are: NANOG, OCT4, SOX2, CD44, LYVE-1, VEGFR-3 and ACE.
2. Cancer stem cells do not co-express the epithelial cancer markers EMA, p63 or cytokeratins 5, 6, 8, 18. This suggests that these cells are more primitive (upstream) than the bulk cancer cells that do express these markers.
3. For the first time, lymphatic markers (LYVE-1 and VEGFR-3) and cancer stem cell markers (CD44) and embryonic stem cell markers (NANOG, OCT4, SOX2) have been shown to be co-expressed. This has interesting implications for understanding the biology of this cell population, and suggests that these cells may be actively involved in driving metastasis via lymphatic channels as distinct from the blood vessels, and also supports our hypothesis that these cancer stem cells are truly pluripotent and capable of de novo lymphangiogenesis (in addition to self-renewal and formation of the bulk tumour cells).
4. Expression of ACE by the cancer stem cell population is also novel, and supports the hypothesis that the renin-angiotensin system (RAS) is involved in regulation of cancer stem cells in some capacity.

Example 3: Expression Analysis Other Cancers

To perform co-expression studies for the expression of the embryonic stem cell marker, OCT4, and Renin Receptor, paraffin sections were stained sequentially for the presence of the two proteins. The images were captured using the Olympus FV-1200 Confocal Microscope and analysed using the Olympus Fluoview FV1000 software. A representative cancer stem cell from each of the cancer systems examined were selected and a cross-sectional line drawn through the middle of it, with the relative expression levels of OCT4, the Renin Receptor relative to the cell nucleus, shown by the expression of 4',6-diamidino-2-phenylindole (DAPI). This evident from the data in the accompanying figures by cancer type, namely: OTSCC (FIGS. 4A, 4B), melanoma (FIGS. 7A, 7B), sarcoma (FIGS. 9A, 9B), bowel cancer (FIGS. 11A, 11B), brain cancer (FIGS. 13A, 13B), breast cancer (FIGS. 15A, 15B), lung cancer (FIGS. 17A, 17B), B cell lymphoma (FIGS. 19A, 19B), and kidney (FIGS. 21A, 21B), thyroid cancer (23A, 23B), chronic lymphocytic cancer (25A, 25B), skin squamous cell carcinoma (27A, 27B), prostate cancer (29A, 29B).

Figure 5:
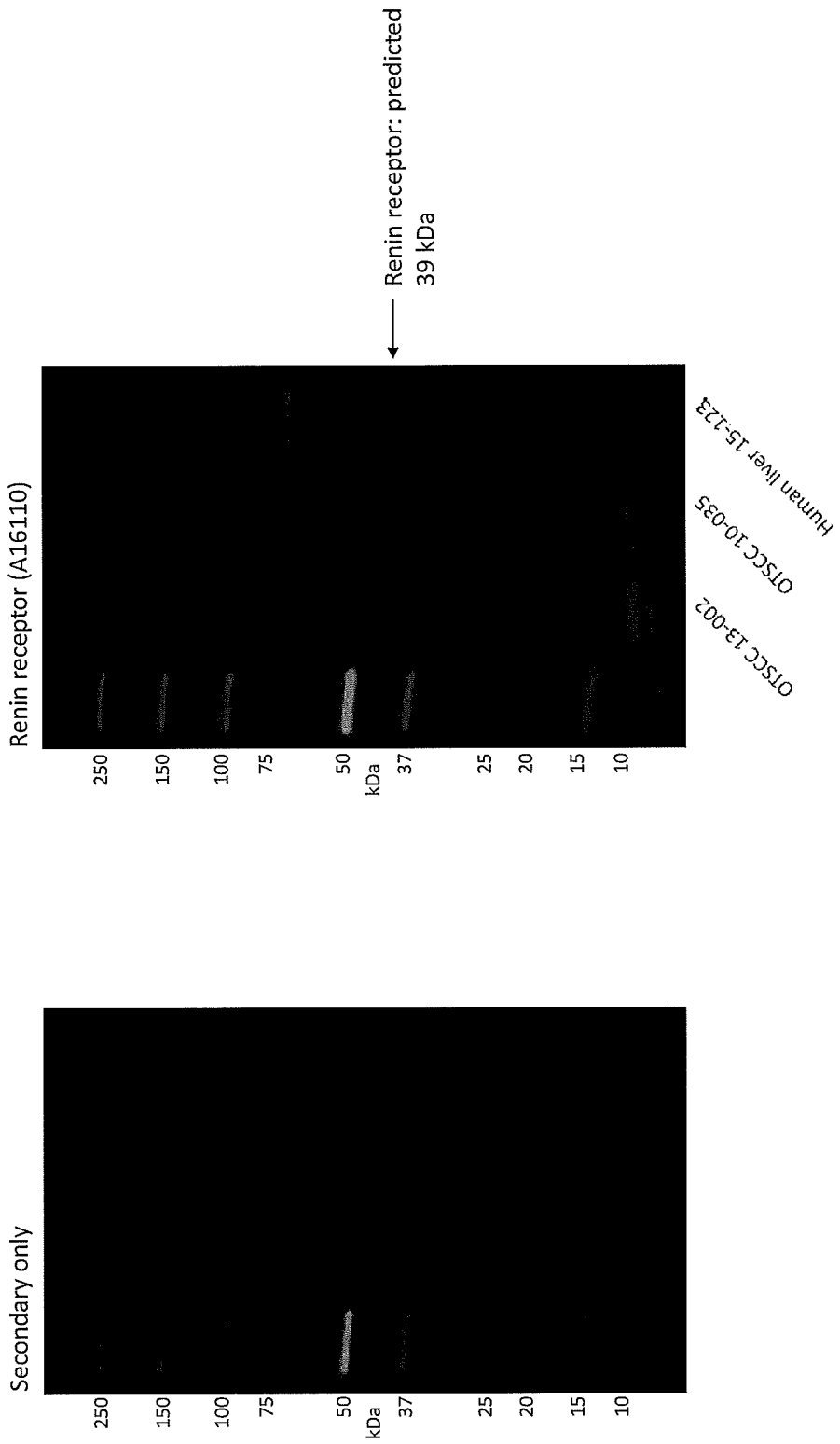
FIGS. 5A and 5B shows the co-localisation of OCT4 and RR by the cancer stem cell population associated with OTSCC.
Figure 6:
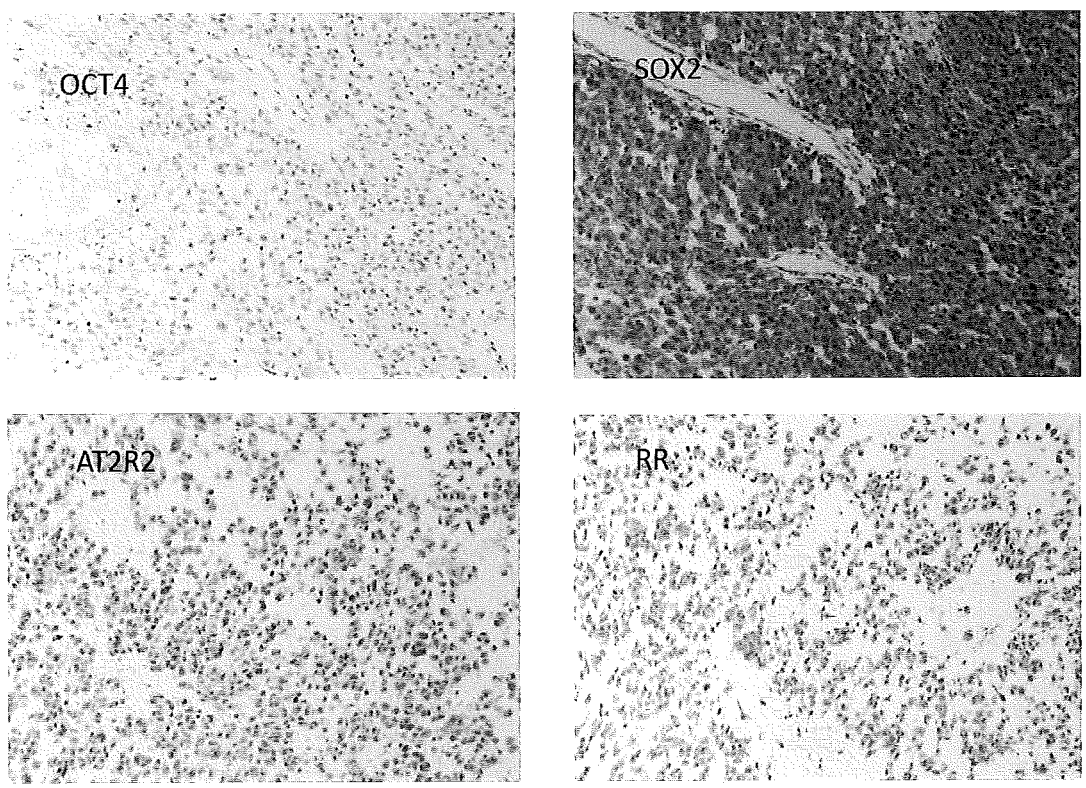
FIG. 6 shows the expression of OCT4, SOX2, ATIIR2 and RR by the cancer stem cell population associated with melanoma as evidenced by the immunohistochemical staining profiles.

The Pro/Renin receptor is a cell surface and cytoplasmic cellular protein detected at about 39 KDa, this protein is then able to be cleaved intracellularly by a number of proteins, such as but not limited to Furin and Cathepsin B (e.g. Wang et al. (1991) *J. Biol. Chem.* 266(19): 12633-12638). The cleaved product is a truncated form of the original protein, which is about 25 KDa in size. Both the full length and the cleaved Pro/Renin forms are shown in FIG. 5. The latter cleaved form is actively secreted into the extracellular fluid, eventually making its way into bodily fluids such as blood, lymph. Accordingly, this marker may be used as a biomarker of cancer, and in particular cancer with an associated cancer stem cell population(s).

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A method for preventing, treating, or managing cancer in a patient in need thereof, the method comprising
   (a) detecting expression of OCT4, SOX2, NANOG, c-Myc, and KLF4 and one or more biomarkers associated with the Renin-Angiotensin System on cancer stem cells from the patient, and
   (b) administering one or more therapeutic agents to the patient in an amount sufficient to selectively eradicate, or inhibit the growth, proliferation and/or differentiation of cancer stem cells in a tumour within the cancer, wherein the therapeutic agent is selected from the group consisting of Direct Renin Inhibitors (DRIs), Angiotensin-Converting Enzyme Inhibitors (ACEIs), Angiotensin Receptor Blockers (ARBs), Beta-Blockers, Cyclo-oxygenase 2 Inhibitors, Chymase Inhibitors, Inhibitors of Cathepsin B, Cathepsin D and Cathepsin G, Calcium, Vitamin D, and Calcium Channel Blockers.

2. A method according to claim 1, wherein step (a) comprises detecting expression of one or more Renin-Angiotensin System biomarkers selected from the group consisting of Renin Receptor, Angiotensin II Receptor 2, and a secreted form of the Renin Receptor.

3. A method according to claim 1, wherein the cancer is selected from the group consisting of squamous cell carcinoma of the head and neck, squamous cell carcinoma of the skin, melanoma, lung cancer, breast cancer, kidney cancer, brain cancer, bowel cancer, thyroid cancer, prostate cancer, lymphoma, leukemia and sarcomas.

4. A method according to claim 3, wherein the cancer is squamous cell carcinoma of the head and neck.

5. The method of claim 3, wherein the squamous cell carcinoma of the head and neck is located in the aerodigestive tract.

6. A method for preventing, treating, or managing cancer in a patient in need thereof, the method comprising (a) detecting expression of SOX2, NANOG, KLF4, and c-Myc and one or more biomarkers associated with the Renin-Angiotensin System on cancer stem cells from the patient, and (b) administering one or more therapeutic agents to the patient in an amount sufficient to selectively eradicate, or inhibit the growth, proliferation and/or differentiation of cancer stem cells in a tumour within the cancer, wherein the therapeutic agent is selected from the group consisting of Direct Renin Inhibitors (DRIs), Angiotensin-Converting Enzyme Inhibitors (ACEIs), Angiotensin Receptor Blockers (ARBs), Beta-Blockers, Cyclo-oxygenase 2 Inhibitors, Chymase Inhibitors, Inhibitors of Cathepsin B, Cathepsin D and Cathepsin G, Calcium, Vitamin D, and Calcium Channel Blockers.

7. The method of claim 6, wherein step (a) comprises detecting lack of expression of OCT4.

8. The method of claim 6, wherein step (a) comprises detecting expression of one or more Renin-Angiotensin System biomarkers selected from the group consisting of Renin Receptor, Angiotensin II Receptor 2, and a secreted form of the Renin Receptor.

* * * * *